(12) United States Patent
Whitty et al.

(10) Patent No.: US 6,800,735 B2
(45) Date of Patent: Oct. 5, 2004

(54) INTERFERON-BETA FUSION PROTEINS AND USES

(75) Inventors: Adrian Whitty, Hopkinton, MA (US); Laura Runkel, Cambridge, MA (US); Margot Brickelmaier, Boxford, MA (US); Paula Hochman, Newton, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/832,659

(22) Filed: Apr. 11, 2001

(65) Prior Publication Data

US 2002/0155547 A1 Oct. 24, 2002

Related U.S. Application Data

(63) Continuation of application No. PCT/US99/24200, filed on Oct. 15, 1999.
(60) Provisional application No. 60/104,491, filed on Oct. 16, 1998, and provisional application No. 60/120,237, filed on Feb. 16, 1999.

(51) Int. Cl.[7] .................. C07K 17/00; C12P 21/08; A61K 38/21; A61K 31/74
(52) U.S. Cl. ................ 530/351; 424/185.1; 424/194.1; 424/85.4; 424/85.6; 424/78.31; 424/192.1; 530/387.3
(58) Field of Search .................. 530/351, 387.3; 424/134.1, 85.4, 85.6, 143.1, 185.1, 192.1, 194.1, 78.31; 514/8

(56) References Cited

U.S. PATENT DOCUMENTS

| | | |
|---|---|---|
| 4,179,337 A | 12/1979 | Davis et al. |
| 4,751,077 A | 6/1988 | Bell et al. |
| 4,766,106 A * | 8/1988 | Katre et al. .......... 514/12 |
| 4,894,226 A | 1/1990 | Aldwin et al. |
| 4,914,033 A * | 4/1990 | Bell et al. .......... 435/252.3 |
| 4,917,888 A | 4/1990 | Katre et al. |
| 5,109,120 A | 4/1992 | Ueno et al. |
| 5,116,964 A * | 5/1992 | Capon et al. ........ 536/23.5 |
| 5,252,714 A | 10/1993 | Harris et al. |
| 5,281,698 A | 1/1994 | Nitecki |
| 5,286,637 A | 2/1994 | Veronese et al. |
| 5,359,030 A | 10/1994 | Ekwuribe |
| 5,382,657 A | 1/1995 | Karasiewicz et al. |
| 5,529,915 A | 6/1996 | Phillips et al. |
| 5,643,575 A | 7/1997 | Martinez et al. |
| 5,681,811 A | 10/1997 | Ekwuribe |
| 5,702,717 A | 12/1997 | Cha et al. |
| 5,711,944 A | 1/1998 | Gilbert et al. |
| 5,738,846 A | 4/1998 | Greenwald et al. |
| 5,783,181 A | 7/1998 | Browne et al. |
| 5,792,834 A | 8/1998 | Hakimi et al. |
| 5,824,784 A | 10/1998 | Kinstler et al. |
| 5,874,075 A | 2/1999 | Collins et al. |
| 5,908,626 A | 6/1999 | Chang et al. |
| 5,965,119 A | 10/1999 | Greenwald et al. |
| 5,985,265 A | 11/1999 | Kinstler et al. |
| 5,990,237 A | 11/1999 | Bentley et al. |
| 6,180,095 B1 | 1/2001 | Greenwald et al. |
| 2001/0011115 A1 | 8/2001 | Harris et al. |

FOREIGN PATENT DOCUMENTS

| | | |
|---|---|---|
| EP | 0 225 579 A | 6/1987 |
| EP | 0 154 316 | 9/1989 |
| EP | 0 229 108 | 12/1990 |
| WO | WO 83/02461 | 7/1983 |
| WO | WO 87/00056 | 1/1987 |
| WO | WO 97/18832 | 11/1995 |
| WO | WO 96/11953 | 4/1996 |
| WO | WO 97/24137 | 7/1997 |
| WO | WO 99/32134 | 12/1997 |
| WO | WO 98/48840 | 11/1998 |
| WO | WO 99/32139 | 7/1999 |
| WO | WO 99/32140 | 7/1999 |
| WO | WO 99/55377 | 11/1999 |
| WO | WO 01/46291 | 6/2001 |

OTHER PUBLICATIONS

Ngo et al., 1994, The Protein Folding Problem and Tertiary Structure Prediction, pp. 492–495.*
Wells, Aditivity of Mutational Effects in Proteins, 1990, Biochemistry, vol. 26, No.: 37, pp. 8509–8517.*
Arduini et al. (1999). *Protein Sci.* 8: 1867–1877.
Genbank Accession No.: E00029 (Sep. 29, 1997).
Karpusas et al. (1997). *Proc. Natl. Acad. Sci. USA* 94: 11813–11818.
Runkel et al. (1998). *Pharm. Res.* 15: 641–649.
Santillan et al. (1992). *Mol. and Cell. Biochem.* 110: 181–191.
International Search Report for PCT/US99/24200 mailed May 22, 2000.

* cited by examiner

Primary Examiner—Gary Kunz
Assistant Examiner—Jegatheesan Seharaseyon
(74) Attorney, Agent, or Firm—Foley Hoag LLP

(57) ABSTRACT

A fusion polypeptide is described having the amino acid sequence X-Y-Z, or portion thereof, comprising the amino acid sequence of a glycosylated interferon-beta (X); Y is an optional linker moiety; and Z is a polypeptide comprising at least a portion of a polypeptide other than glycosylated interferon-beta. It is preferred that X is human interferon-beta-1a. Mutants of interferon-beta-1a are also described.

5 Claims, 17 Drawing Sheets

```
  1 TCCGGGGGCC ATCATCATCA TCATCATAGC TCCGGAGACG ATGATGACAA GATGAGCTAC
  1▸SerGlyGlyH isHisHisHi sHisHisSer SerGlyAspA spAspAspLy sMetSerTyr
 61 AACTTGCTTG GATTCCTACA AAGAAGCAGC AATTTTCAGT GTCAGAAGCT CCTGTGGCAA
 21▸AsnLeuLeuG lyPheLeuGl nArgSerSer AsnPheGlnC ysGlnLysLe uLeuTrpGln
121 TTGAATGGGA GGCTTGAATA CTGCCTCAAG GACAGGATGA ACTTTGACAT CCCTGAGGAG
 41▸LeuAsnGlyA rgLeuGluTy rCysLeuLys AspArgMetA snPheAspIl eProGluGlu
181 ATTAAGCAGC TGCAGCAGTT CCAGAAGGAG GACGCCGCAT TGACCATCTA TGAGATGCTC
 61▸IleLysGlnL euGlnGlnPh eGlnLysGlu AspAlaAlaL euThrIleTy rGluMetLeu
241 CAGAACATCT TTGCTATTTT CAGACAAGAT TCATCTAGCA CTGGCTGGAA TGAGACTATT
 81▸GlnAsnIleP heAlaIlePh eArgGlnAsp SerSerSerT hrGlyTrpAs nGluThrIle
301 GTTGAGAACC TCCTGGCTAA TGTCTATCAT CAGATAAACC ATCTGAAGAC AGTCCTGGAA
101▸ValGluAsnL euLeuAlaAs nValTyrHis GlnIleAsnH isLeuLysTh rValLeuGlu
361 GAAAAACTGG AGAAAGAAGA TTTCACCAGG GGAAAACTCA TGAGCAGTCT GCACCTGAAA
121▸GluLysLeuG luLysGluAs pPheThrArg GlyLysLeuM etSerSerLe uHisLeuLys
421 AGATATTATG GGAGGATTCT GCATTACCTG AAGGCCAAGG AGTACAGTCA CTGTGCCTGG
141▸ArgTyrTyrG lyArgIleLe uHisTyrLeu LysAlaLysG luTyrSerHi sCysAlaTrp
481 ACCATAGTCA GAGTGGAAAT CCTAAGGAAC TTTTACTTCA TTAACAGACT TACAGGTTAC
161▸ThrIleValA rgValGluIl eLeuArgAsn PheTyrPheI leAsnArgLe uThrGlyTyr
541 CTCCGAAAC
181▸LeuArgAsn
```

```
1   ATGAGCTACA ACTTGCTTGG ATTCCTACAA AGAAGCAGCA ATTTTCAGTG TCAGAAGCTC
1  ▶MetSerTyrA snLeuLeuGl yPheLeuGln ArgSerSerA snPheGlnCy sGlnLysLeu

61  CTGTGGCAAT TGAATGGGAG GCTTGAATAC TGCCTCAAGG ACAGGATGAA CTTTGACATC
21 ▶LeuTrpGlnL euAsnGlyAr gLeuGluTyr CysLeuLysA spArgMetAs nPheAspIle

121 CCTGAGGAGA TTAAGCAGCT GCAGCAGTTC CAGAAGGAGG ACGCCGCATT GACCATCTAT
41 ▶ProGluGlul leLysGlnLe uGlnGlnPhe GlnLysGluA spAlaAlaLe uThrIleTyr 181 GAGATGCTCC AGAACATCTT TGCTATTTTC AGACAAGATT CATCTAGCAC TGGCTGGAAT
61 ▶GluMetLeuG lnAsnIlePh eAlaIlePhe ArgGlnAspS erSerSerTh rGlyTrpAsn 241 GAGACTATTG TTGAGAACCT CCTGGCTAAT GTCTATCATC AGATAAACCA TCTGAAGACA
81 ▶GluThrIleV alGluAsnLe uLeuAlaAsn ValTyrHisG lnIleAsnHi sLeuLysThr 301 GTCCTGGAAG AAAAACTGGA GAAAGAAGAT TTCACCAGGG GAAAACTCAT GAGCAGTCTG
101▶ValLeuGluG luLysLeuGl uLysGluAsp PheThrArgG lyLysLeuMe tSerSerLeu 361 CACCTGAAAA GATATTATGG GAGGATTCTG CATTACCTGA AGGCCAAGGA GTACAGTCAC
121▶HisLeuLysA rgTyrTyrGl yArgIleLeu HisTyrLeuL ysAlaLysGl uTyrSerHis 421 TGTGCCTGGA CCATAGTCAG AGTGGAAATC CTAAGGAACT TTTACTTCAT TAACAGACTT
141▶CysAlaTrpT hrIleValAr gValGluIle LeuArgAsnP heTyrPheIl eAsnArgLeu 481 ACAGGTTACC TCCGAAACGA CGATGATGAC AAGGTCGACA AAACTCACAC ATGCCCACCG
161▶ThrGlyTyrL euArgAsnAs pAspAspAsp LysValAspL ysThrHisTh rCysProPro

541 TGCCCAGCAC CTGAACTCCT GGGGGGACCG TCAGTCTTCC TCTTCCCCCC AAAACCCAAG
```

FIG. 2A-2

```
181 ▶CysProAlaP  roGluLeuLe uGlyGlyPro  SerValPheL  euPheProPr oLysProLys

601 GACACCCTCA TGATCTCCCG GACCCCTGAG GTCACATGCG TGGTGGTGGA CGTGAGCCAC

201 ▶AspThrLeuM etIleSerAr gThrProGlu ValThrCysV alValValAs pValSerHis

661 GAAGACCCTG AGGTCAAGTT CAACTGGTAC GTGGACGGCG TGGAGGTGCA TAATGCCAAG

221 ▶GluAspProG luValLysPh eAsnTrpTyr ValAspGlyV alGluValHi sAsnAlaLys
```

FIG. 2B

```
721 ACAAAGCCGC GGGAGGAGCA GTACAACAGC ACGTACCGTG TGGTCAGCGT CCTCACCGTC

1 ▶ThrLysProA rgGluGluGl nTyrAsnSer ThrTyrArgV alValSerVa lLeuThrVal

781 CTGCACCAGG ACTGGCTGAA TGGCAAGGAG TACAAGTGCA AGGTCTCCAA CAAAGCCCTC

21 ▶LeuHisGlnA spTrpLeuAs nGlyLysGlu TyrLysCysL ysValSerAs nLysAlaLeu

841 CCAGCCCCCA TCGAGAAAAC CATCTCCAAA GCCAAAGGGC AGCCCCGAGA ACCACAGGTG

41 ▶ProAlaProI leGluLysTh rIleSerLys AlaLysGlyG lnProArgGl uProGlnVal

901 TACACCCTGC CCCCATCCCG GGATGAGCTG ACCAAGAACC AGGTCAGCCT GACCTGCCTG

61 ▶TyrThrLeuP roProSerAr gAspGluLeu ThrLysAsnG lnValSerLe uThrCysLeu

961 GTCAAAGGCT TCTATCCCAG CGACATCGCC GTGGAGTGGG AGAGCAATGG GCAGCCGGAG

81 ▶ValLysGlyP heTyrProSe rAspIleAla ValGluTrpG luSerAsnGl yGlnProGlu

1021 AACAACTACA AGACCACGCC TCCCGTGTTG GACTCCGACG GCTCCTTCTT CCTCTACAGC

101 ▶AsnAsnTyrL ysThrThrPr oProValLeu AspSerAspG lySerPhePh eLeuTyrSer

1081 AAGCTCACCG TGGACAAGAG CAGGTGGCAG CAGGGGAACG TCTTCTCATG CTCCGTGATG

121 ▶LysLeuThrV alAspLysSe rArgTrpGln GlnGlyAsnV alPheSerCy sSerValMet

1141 CATGAGGCTC TGCACAACCA CTACACGCAG AAGAGCCTCT CCCTGTCTCC CGGGAAA

141 ▶HisGluAlaL euHisAsnHi sTyrThrGln LysSerLeuS erLeuSerPr oGlyLys
```

| FIG. 10A |
| FIG. 10B |
| FIG. 10C |

FIG. 10

IFNβ G162C-Ig direct fusion construct open reading frame

```

```
481  GAGTACAGTCACTGTGCCTGGACCATAGTCAGAGTGGAAATCCTAAGGAACTTTACTTC  540
      E  Y  S  H  C  A  W  T  I  V  R  V  E  I  L  R  N  F  Y  F

541  ATTAACAGACTTACATGTTACCTCCGAAACTGACAAACTCACACATGCCACCGTGC    600
      I  N  R  L  T  C  Y  L  R  N  V  D  K  T  H  T  C  P  P  C

601  CCAGCACCTGAACTCCTGGGGACCGTCAGTCTTCCTCTTCCCCCAAAACCCAAGGAC    660
      P  A  P  E  L  L  G  G  P  S  V  F  L  F  P  P  K  P  K  D

661  ACCCTCATGATCTCCCGGACCCCTGAGGTCACATGCGTGGTGGTGGACGTGAGCCACGAA 720
      T  L  M  I  S  R  T  P  E  V  T  C  V  V  V  D  V  S  H  E

721  GACCCTGAGGTCAAGTTCAACTGGTACGTGGACGGCGTGGAGGTGCATAATGCCAAGACA 780
      D  P  E  V  K  F  N  W  Y  V  D  G  V  E  V  H  N  A  K  T

781  AAGCCGCGGGAGGAGCAGTACAACAGCACGTACCGTGTGGTCAGCGTCCTCACCGTCCTG 840
      K  P  R  E  E  Q  Y  N  S  T  Y  R  V  V  S  V  L  T  V  L

841  CACCAGGACTGGCTGAATGGCAAGGAGTACAAGTGCAAGGTCTCCAACAAAGCCCTCCCA 900
      H  Q  D  W  L  N  G  K  E  Y  K  C  K  V  S  N  K  A  L  P

901  GCCCCCATCGAGAAAACCATCTCCAAAGCCAAAGGGCAGCCCCGAGAACCACAGGTGTAC 960
      A  P  I  E  K  T  I  S  K  A  K  G  Q  P  R  E  P  Q  V  Y
```

FIG. 10B

```
 961  ACCCTGCCCCCATCCCGGGATGAGCTGACCAAGAACCAGGTCAGCCTGACCTGCCTGGTC  1020
       T  L  P  P  S  R  D  E  L  T  K  N  Q  V  S  L  T  C  L  V

1021  AAAGGCTTCTATCCCAGCGACATCGCCGTGGAGTGGGAGAGCAATGGGCAGCCGGAGAAC  1080
       K  G  F  Y  P  S  D  I  A  V  E  W  E  S  N  G  Q  P  E  N

1081  AACTACAAGACCACGCCTCCCGTGTTGGACTCCGACGGCTCCTTCTTCCTCTACAGCAAG  1140
       N  Y  K  T  T  P  P  V  L  D  S  D  G  S  F  F  L  Y  S  K

1141  CTCACCGTGGACAAGAGCAGGTGGCAGCAGGGGAACGTCTTCTCATGCTCCGTGATGCAT  1200
       L  T  V  D  K  S  R  W  Q  Q  G  N  V  F  S  C  S  V  M  H

1201  GAGGCTCTGCACAACCACTACACGCAGAAGAGCCTCTCCCTGTCTCCGGGAAATGA      1257
       E  A  L  H  N  H  Y  T  Q  K  S  L  S  L  S  P  G  K  *
```

FIG. 10C

| FIG. 11A |
| FIG. 11B |
| FIG. 11C |

FIG. 11

IFNβ G162C-Ig fusion G4S linker construct open reading frame

```
  1 ATGCCTGGGAAGATGGTCGTGATCCTTGGAGCCTCAAATATACTTTGGATAATGTTTGCA  60
    M  P  G  K  M  V  V  I  L  G  A  S  N  I  L  W  I  M  F  A

61 GCTTCTCAAGCCATGAGCTACAACTTGCTTGGATTCCTACAAAGAAGCAGCAATTTTCAG 120
    A  S  Q  A  M  S  Y  N  L  L  G  F  L  Q  R  S  S  N  F  Q

121 TGTCAGAAGCTCCTGTGGCAATTGAATGGAGGCTTGAATACTGCCTCAAGGACAGGATG 180
    C  Q  K  L  L  W  Q  L  N  G  R  L  E  Y  C  L  K  D  R  M

181 AACTTTGACATCCCTGAGGAGATTAAGCAGCTGCAGCAGTTCCAGAAGGAGGACGCCGCA 240
    N  F  D  I  P  E  E  I  K  Q  L  Q  Q  F  Q  K  E  D  A  A

241 TTGACCATCTATGAGATGCTCCAGAACATCTTTGCTATTTTCAGACAAGATTCATCTAGC 300
    L  T  I  Y  E  M  L  Q  N  I  F  A  I  F  R  Q  D  S  S  S

301 ACTGGCTGGAATGAGACTATTGTTGAGAACCTCCTGGCTAATGTCTATCATCAGATAAAC 360
    T  G  W  N  E  T  I  V  E  N  L  L  A  N  V  Y  H  Q  I  N

361 CATCTGAAGACAGTCCTGGAAGAAAAACTGGAGAAAGAAGATTTCACCAGGGGAAAACTC 420
    H  L  K  T  V  L  E  E  K  L  E  K  E  D  F  T  R  G  K  L
```

FIG. 11A

```
421 ATGAGCAGTCTGCACCTGAAAAGATATTATGGAGGATTCTGCATTACCTGAAGGCCAAG 480
     M  S  S  L  H  L  K  R  Y  Y  G  R  I  L  H  Y  L  K  A  K

481 GAGTACAGTCACTGTGCCTGGACCATAGTCAGAGTCAGAGTGGAAATCCTAAGGAACTTTACTTC 540
     E  Y  S  H  C  A  W  T  I  V  R  V  E  I  L  R  N  F  Y  F

541 ATTAACAGACTTACATGTTACCTCCGAAACGGCGGTGGTGGCAGCGTCGACAAAACTCAC 600
     I  N  R  L  T  C  Y  L  R  N  G  G  G  G  S  V  D  K  T  H

601 ACATGCCCACCGTGCCCAGCACCTGAACTCCTGGGGACCGTCAGTCTTCCTCTTCCCC 660
     T  C  P  P  C  P  A  P  E  L  L  G  G  P  S  V  F  L  F  P

661 CCAAAACCAAGGACACCCTCATGATCTCCCGGACCCCTGAGGTCACATGCGTGGTGGTG 720
     P  K  P  K  D  T  L  M  I  S  R  T  P  E  V  T  C  V  V  V

721 GACGTGAGCCACGAAGACCCTGAGGTCAAGTTCAACTGGTACGTGGACGGCGTGGAGGTG 780
     D  V  S  H  E  D  P  E  V  K  F  N  W  Y  V  D  G  V  E  V

781 CATAATGCCAAGACAAAGCCGCGGGAGGAGCAGTACAACAGCACGTACCGTGTGGTCAGC 840
     H  N  A  K  T  K  P  R  E  E  Q  Y  N  S  T  Y  R  V  V  S

841 GTCCTCACCGTCCTGCACCAGGACTGGCTGAATGGCAAGGAGTACAAGTGCAAGGTCTCC 900
     V  L  T  V  L  H  Q  D  W  L  N  G  K  E  Y  K  C  K  V  S

901 AACAAAGCCCTCCCAGCCCCCATCGAGAAAACCATCTCCAAAGCCAAAGGGCAGCCCCGA 960
     N  K  A  L  P  A  P  I  E  K  T  I  S  K  A  K  G  Q  P  R
```

FIG. 11B

```
 961 GAACCACAGGTGTACACCCTGCCCCCATCCCGGGATGAGCTGACCAAGAACCAGGTCAGC 1020
     E  P  Q  V  Y  T  L  P  P  S  R  D  E  L  T  K  N  Q  V  S

1021 CTGACCTGCCTGGTCAAAGGCTTCTATCCCAGCGACATCGCCGTGGAGTGGGAGAGCAAT 1080
     L  T  C  L  V  K  G  F  Y  P  S  D  I  A  V  E  W  E  S  N

1081 GGGCAGCCGGAGAACAACTACAAGACCACGCCTCCCGTGTTGGACTCCGACGGCTCCTTC 1140
     G  Q  P  E  N  N  Y  K  T  T  P  P  V  L  D  S  D  G  S  F

1141 TTCCTCTACAGCAAGCTCACCGTGGACAAGAGCAGGTGGCAGCAGGGGAACGTCTTCTCA 1200
     F  L  Y  S  K  L  T  V  D  K  S  R  W  Q  Q  G  N  V  F  S

1201 TGCTCCGTGATGCATGAGGCTCTGCACAACCACTACACGCAGAAGAGCCTCTCCCTGTCT 1260
     C  S  V  M  H  E  A  L  H  N  H  Y  T  Q  K  S  L  S  L  S

1261 CCCGGGAAATGA 1272
     P  G  K  *
```

FIG. 11C

INTERFERON-BETA FUSION PROTEINS AND USES

RELATED APPLICATIONS

This is a continuation of PCT/US99/24200, filed on Oct. 15, 1999 as a continuation-in-part of prior U.S. Provisional S. No. 60/104,491 filed Oct. 16, 1998 and U.S. Provisional S. No. 60/120,237 filed Feb. 16, 1999. The teachings of the earlier-filed patent applications are incorporated herein by reference.

BACKGROUND OF THE INVENTION

Use of polypeptides and proteins for the systemic treatment of specific diseases is now well accepted in medical practice. The role that these substances play in therapy is so important that many research activities are being directed towards the synthesis of large quantities by recombinant DNA technology. Many of these polypeptides are endogenous molecules which are very potent and specific in eliciting their biological actions.

A major factor limiting the usefulness of these proteinaceous substances for their intended application is that, when given parenterally, they are eliminated from the body within a short time. This can occur as a result of metabolism by proteases or by clearance using normal pathways for protein elimination such as by filtration in the kidneys. The problems associated with these routes of administration of proteins are well known in the pharmaceutical industry, and various strategies are being used in attempts to solve them.

A peptide family, which has been the focus of much clinical work, and efforts to improve its administration and bio-assimilation, is the interferons. Interferons have been tested in a variety of clinical disease states. The use of human interferon beta, one member of that family, is best established in the treatment of multiple sclerosis. Two forms of recombinant interferon beta, have recently been licensed in Europe and the U.S. for treatment of this disease. One form is interferon-beta-1a (trademarked, sold as AVONEX®, mfg. Biogen, Inc., Cambridge, Mass.) and hereinafter, "interferon-beta-1a" or "IFN-beta-1a" or "IFN-β-1a" or "interferon-β-1a", used interchangeably. The other form is interferon-beta-1b (trademarked and sold as BETASERON®, Berlex, Richmond Calif.), hereinafter, "interferon-beta-1b". Interferon beta-1a is produced in mammalian cells using the natural human gene sequence and is glycosylated, whereas interferon beta-1b is produced in *E. coli* bacteria using a modified human gene sequence that contains a genetically engineered cysteine-to-serine substitution at amino acid position 17 and is non-glycosylated.

Previously, several of us have directly compared the relative in vitro potencies of interferon-beta-1a and interferon beta 1b in functional assays and showed that the specific activity of interferon-beta-1a is approximately 10-fold greater than the specific activity of interferon-beta-1b (Runkel et al., 1998, Pharm. Res. 15: 641–649). From studies designed to identify the structural basis for these activity differences, we identified glycosylation as the only one of the known structural differences between the products that affected the specific activity. The effect of the carbohydrate was largely manifested through its stabilizing role on structure. The stabilizing effect of the carbohydrate was evident in thermal denaturation experiments and SEC analysis. Lack of glycosylation was also correlated with an increase in aggregation and an increased sensitivity to thermal denaturation. Enzymatic removal of the carbohydrate from interferon-beta-1a with PNGase F caused extensive precipitation of the deglycosylated product.

These studies indicate that, despite the conservation in sequence between interferon-beta-1a and interferon-beta-1b, they are distinct biochemical entities and therefore much of what is known about interferon-beta-1b cannot be applied to interferon-beta-1a, and vice versa.

SUMMARY OF THE INVENTION

We have exploited the advantages of glycosylated interferon-beta relative to non-glycosylated forms. In particular, we have developed an interferon-beta-1a composition with increased activity relative to interferon-beta-1b and that also has the salutary properties of fusion proteins in general with no effective loss in activity as compared to interferon-beta-1a forms that are not fusion proteins. Thus, if modifications are made in such a way that the products (interferon-beta 1a fusion proteins) retain all or most of their biological activities, the following properties may result: altered pharmacokinetics and pharmacodynamics leading to increased half-life and alterations in tissue distribution (e.g, ability to stay in the vasculature for longer periods of time) Such a formulation is a substantial advance in the pharmaceutical and medical arts and would make a significant contribution to the management of various diseases in which interferon has some utility, such as multiple sclerosis, fibrosis, and other inflammatory or autoimmune diseases, cancers, hepatitis and other viral diseases and diseases characterized by neovascularization. In particular, the ability to remain for longer periods of time in the vasculature allows the interferon-beta-1a to be used to inhibit angiogenesis and potentially to cross the blood-brain barrier.

In particular, the invention relates to an isolated polypeptide having the amino acid sequence X-Y-Z, wherein X is a polypeptide having the amino acid sequence, or portion thereof, consisting of the amino acid sequence of interferon beta; Y is an optional linker moiety; and Z is a polypeptide comprising at least a portion of a polypeptide other than interferon beta. Optional moiety Y and required moiety Z may be linked to either the N- or C-terminus of inteferon beta (X). Preferably, X is human interferon-beta-1a. In the preferred embodiments, Z is at least a portion of a constant region of an immunoglobulin and can be derived from an immunoglobulin of the class selected from IgM, IgG, IgD, IgA, and IgE. If the class is IgG, then it is selected from one of IgG1, IgG2, IgG3 and IgG4. The constant region of human IgM and IgE contain 4 constant regions (CH1, (hinge), CH2, CH3 and CH4, whereas the constant region of human IgG, IgA and IgD contain 3 constant regions (CH1, (hinge), CH2 and CH3. In the most preferred fusion proteins of the invention, the constant region contains at least the hinge, CH2 and CH3 domains. In other embodiments, moiety Z is at least a portion of a polypeptide that contains immunoglobulin-like domains. Examples of such other polypeptides include CD1, CD2, CD4, and members of class I and class II major histocompatability antigens.

Another embodiment of the invention is a fusion protein having an amino terminal region consisting of the amino acid sequence of interferon beta or a portion thereof and having a carboxy terminal region comprising at least a portion of a protein other than interferon beta. The carboxy portion is preferably at least a portion of a constant region of an immunoglobulin derived from an immunoglobulin of the class selected from IgM, IgG, IgD, IgA, and IgE. In the most preferred fusion proteins, the constant region contains at least the hinge, CH2 and CH3 domains.

Another embodiment of the invention is a fusion protein whose interferon beta moiety (e.g., X in the formula above) has been mutated to provide for muteins with selectively enhanced antiviral and/or antiproliferative activity or other advantageous properties relative to non-mutated forms of interferon-beta-1a.

Yet another embodiment of the invention is an isolated DNA encoding for the fusion proteins described above. The invention also pertains to a recombinant DNA comprising an isolated DNA encoding the fusion proteins described above and an expression control sequence, wherein the expression control sequence is operatively linked to the DNA. The scope of the invention also includes host cells transformed with the recombinant DNA sequences of the invention.

The invention further pertains to a method of producing a recombinant polypeptide comprising: providing a population of host cells according to the invention; growing the population of cells under conditions whereby the polypeptide encoded by the recombinant DNA is expressed; and isolating the expressed polypeptide.

A further aspect of the invention is a interferon-beta 1a fusion protein comprising interferon-beta-1a and additional polypeptide with which it is not natively associated, in substantially purified form, the fusion having an antiviral activity that is about equal to the anti-viral activity of interferon-beta-1a lacking the additional polypeptide.

Yet another aspect of the invention is a pharmaceutical composition comprising a therapeutically effective amount of an interferon-beta-1a fusion protein.

Yet another aspect of the invention is a method of inhibiting angiogenesis and neovascularization using the polypeptides of the invention.

BRIEF DESCRIPTION OF THE FIGURES

FIG. 1 cDNA and deduced amino acid sequence of a histidine tagged-interferon-beta fusion (also called "his IFN-beta" or "$His_6$-tagged"). The full DNA and protein sequences of the his IFN-beta-1a are shown. The cleaved VCAM-1 signal sequence leaves 3 amino terminal residues (SerGlyGly) upstream of the histidine tag ($His_6$, positions 4–9). The enterokinase linker sequence (AspAspAspAspLys) is separate from the histidine tag by a spacer (positions 10–12, SerSerGly). The natural IFN-beta-1a protein sequence spans positions (Met18–Asn183).

FIG. 2. cDNA and deduced amino acid sequence for an interferon-beta-1a/Fc fusion. The full DNA and protein sequences of the human EFN-beta-1a/mouse Fc are shown in FIGS. 2A-1, 2A-2 and 2B. The human BEN-beta-1a protein sequences span amino acid residues 1–166 (DNA sequences 1–498). The enterokinase linker sequence spans amino acid residues 167–171 (DNA sequences 499–513). The murine IgG2a heavy chain protein sequence spans residues 172–399 (DNA sequences 514–1197).

FIG. 10. Full DNA and protein sequences of the open reading frames of a direct fusion of human IFN beta and human IgG1Fc (ZL5107)

FIG. 11. Full DNA and protein sequences of the open reading frame of a fusion protein consisting of human IFN beta/G4S linker/human IgG1FC (ZL6206).

DETAILED DESCRIPTION

Figure 3:
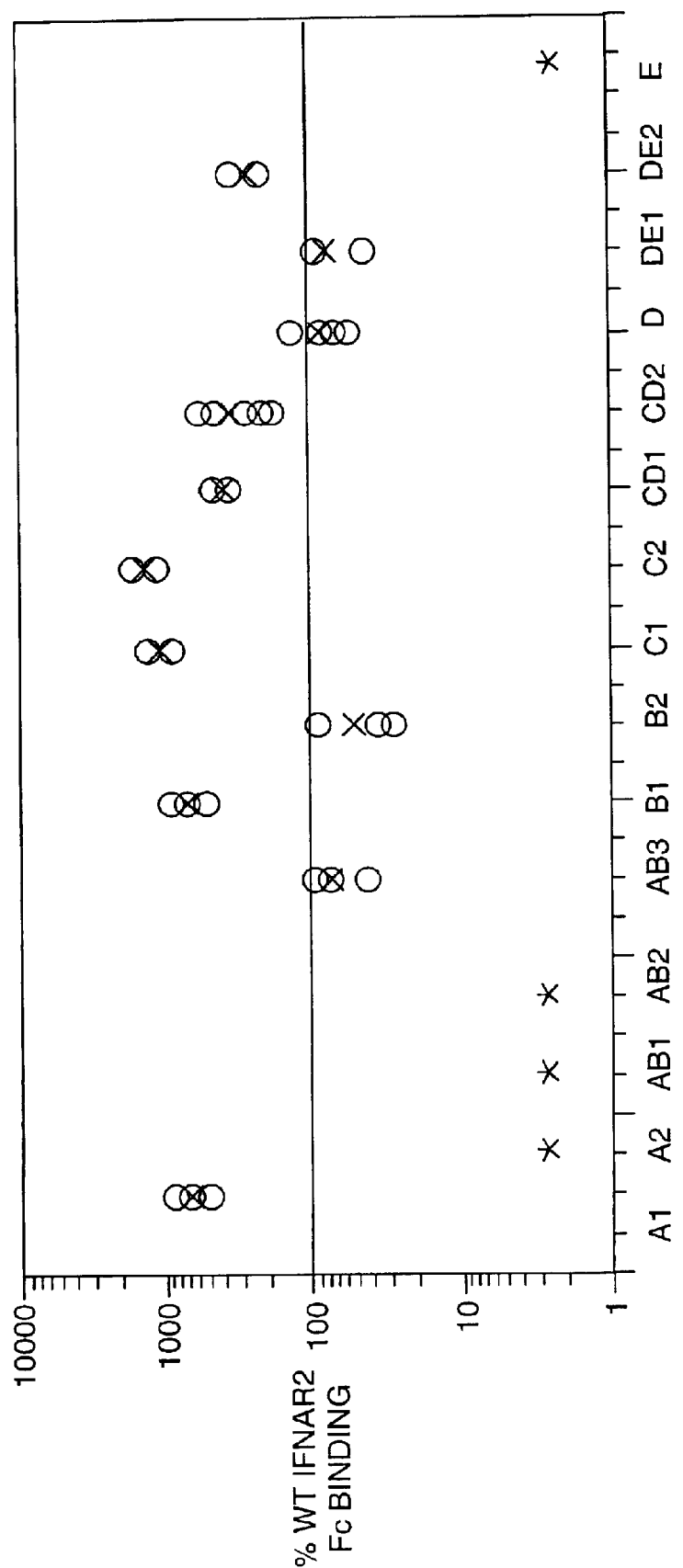
FIG. 3. Binding of alanine substituted interferon-beta mutants to a dimeric fusion protein comprised of the extracellular domain of the type I interferon receptor chain, IFNAR2/Fc. The binding affinities of the alanine substituted IFN mutants (A1–E) for the IFNAR2 receptor chain were determined as described in Example 1 (subsection D). The histogram presents their binding affinities in this assay relative to wild type his-IFN-beta (% w.t.). The % w.t. values were calculated as the (affinity of wild type his-IFN-beta)/(affinity of mutant IFN-beta)×100. The % w.t. (x) for multiple assays (n=3) and an average % w.t. (x) for the experimental set are sh or 50,000 Units of interferon-beta-1a/Fc fusion. Blood from these mice is obtained via retro-orbital bleeds at various times after interferon injection as indicated on the X axis. There are at least 3 mice bled at each time point, and plasma is prepared and frozen until the time interferon-beta activity is evaluated in antiviral assays using human lung carcinoma (A549) cells challenged with encephalomyocarditis virus. Viable cells were stained with a solution of MTT, the plates were read at 450 nm, to determine the absorbance which is reflective of cell viability and interferon-beta activity. Standard curves were generated for each plate using interferon-beta-1a as AVONEX® and used to determine the amount of interferon-beta activity in each sample. Data from the individual animals are shown.
Figure 4:
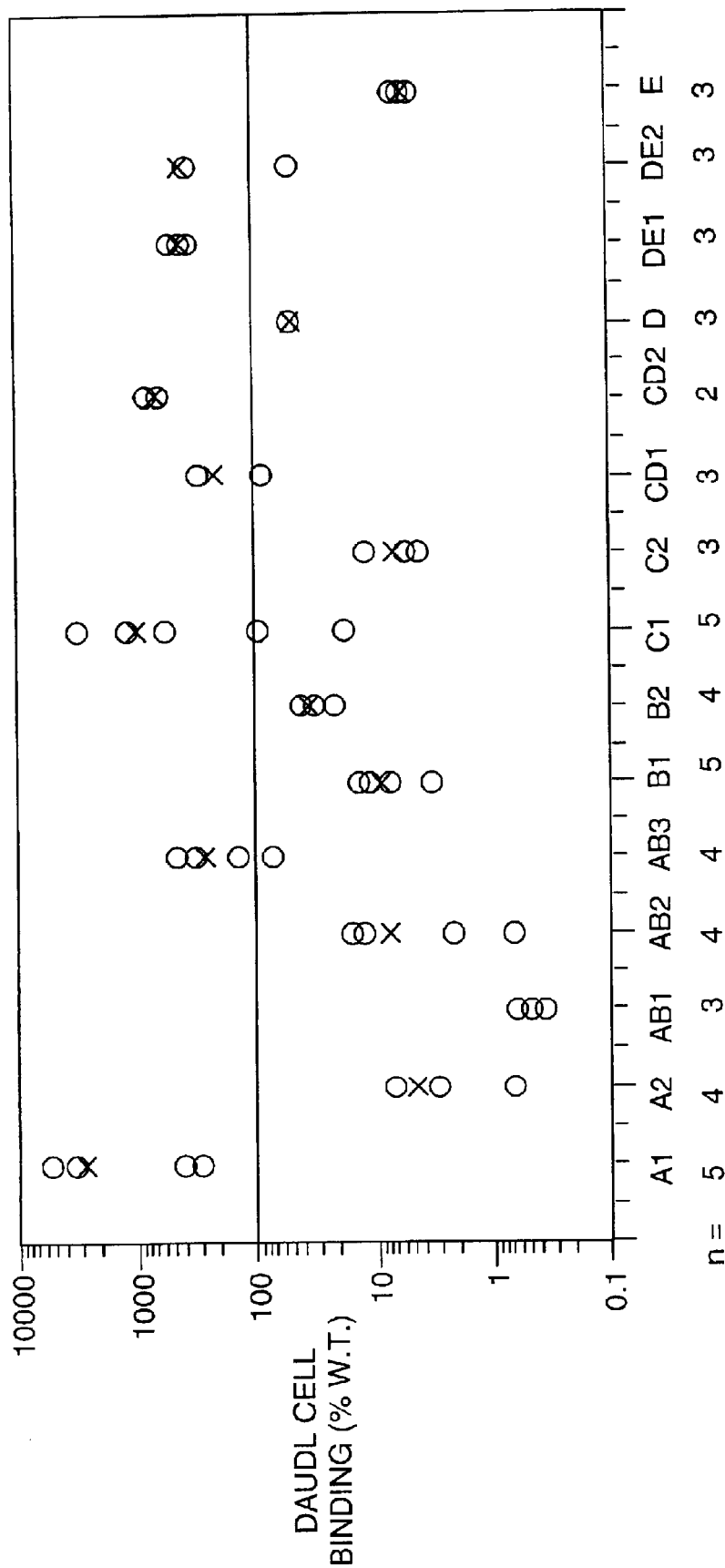

All references cited in the Detailed Description are incorporated herein by references, unless stipulated otherwise. The following terms are used herein:

I. Definitions:

Interferon—An "interferon" (also referred to as "IFN") is a small, species-specific, single chain polypeptide, produced by mammalian cells in response to exposure to a variety of inducers such as viruses, polypeptides, mitogens and the like. The most preferred interferon used in the invention is glycosylated, human, interferon-beta that is glycosylated at residue 80 (Asn 80) and that is preferably derived via recombinant DNA technologies. This preferred glycosylated interferon beta is called "interferon-beta-1a" (or "IFN-beta-1a" or "IFN-ꓱ-1a" or or "interferon beta 1a" or "interferon-beta-1a" or "interferon-ꓱ-1a", all used interchangeably). The term "interferon-beta-1a" is also intended to encompass all mutant forms (i.e., Example 1) provided that the mutants are also glycosylated at the Asn 80 residue.

Recombinant DNA methods for producing proteins, including interferons are known. See for example, U.S. Pat. Nos. 4,399,216, 5,149,636, 5,179,017 (Axel et al) and U.S. Pat. No. 4,470,461 (Kaufman).

Preferred interferon-beta-1a polynucleotides that may be used in the present methods of the invention are derived from the wild-type interferon beta gene sequences of various vertebrates, preferably mammals and are obtained using methods that are well-known to those having ordinary skill in the art such as the methods described in the following U.S. Patents: U.S. Pat. No. 5,641,656 (issued Jun. 24, 1997: DNA encoding avian type I interferon proprotein and mature avian type I interferon), U.S. Pat. No. 5,605,688 (Feb. 25, 1997-recombinant dog and horse type I interferons); U.S. Pat. No. 5,231,176 (Jul. 27, 1993, DNA molecule encoding a human leukocyte interferon);); U.S. Pat. No. 5,071,761 (Dec. 10, 1991, DNA sequence coding for sub-sequences of human lymphoblastoid interferons LyIFN-alpha-2 and LyIFN-alpha-3); U.S. Pat. No. 4,970,161 (Nov. 13, 1990, DNA sequence coding for human interferon-gamma); U.S. Pat. No. 4,738,931 (Apr. 19, 1988, DNA containing a human interferon beta gene); U.S. Pat. No. 4,695,543 (Sep. 22, 1987, human alpha-interferon Gx-1 gene and U.S. Pat. No. 4,456,748 (Jun. 26, 1984, DNA encoding sub-sequences of different, naturally, occurring leukocyte interferons).

Mutants of interferon-beta-1a may be used in accordance with this invention. Mutations are developed using conventional methods of directed mutagenesis, known to those of ordinary skill in the art. Moreover, the invention provides for functionally equivalent interferon-beta-1a polynucleotides that encode for functionally equivalent interferon-beta-1a polypeptides.

A first polynucleotide encoding interferon-beta-1a is "functionally equivalent" compared with a second polynucleotide encoding interferon-beta-1a if it satisfies at least one of the following conditions:

(a): the "functional equivalent" is a first polynucleotide that hybridizes to the second polynucleotide under standard hybridization conditions and/or is degenerate to the first polynucleotide sequence. Most preferably, it encodes a mutant interferon having the [therapeutic] activity of an interferon-beta-1a;

(b) the "functional equivalent" is a first polynucleotide that codes on expression for an amino acid sequence encoded by the second polynucleotide.

In summary, the term "interferon" includes, but is not limited to, the agents listed above as well as their functional equivalents. As used herein, the term "functional equivalent" therefore refers to an interferon-beta-1a protein or a polynucleotide encoding the interferon-beta-1a protein that has the same or an improved beneficial effect on the mammalian recipient as the interferon of which it is deemed a functional equivalent. As will be appreciated by one of ordinary skill in the art, a functionally equivalent protein can be produced by recombinant techniques, e.g., by expressing a "functionally equivalent DNA". Accordingly, the instant invention embraces interferon-beta-1a proteins encoded by naturally-occurring DNAs, as well as by non-naturally-occurring DNAs which encode the same protein as encoded by the naturally-occurring DNA. Due to the degeneracy of the nucleotide coding sequences, other polynucleotides may be used to encode interferon-beta-1a. These include all, or portions of the above sequences which are altered by the substitution of different codons that encode the same amino acid residue within the sequence, thus producing a silent change. Such altered sequences are regarded as equivalents of these sequences. For example, Phe (F) is coded for by two codons, TTC or TTT, Tyr (Y) is coded for by TAC or TAT and His (H) is coded for by CAC or CAT. On the other hand, Trp (W) is coded for by a single codon, TGG. Accordingly, it will be appreciated that for a given DNA sequence encoding a particular interferon there will be many DNA degenerate sequences that will code for it. These degenerate DNA sequences are considered within the scope of this invention.

"fusion"—refers to a co-linear, covalent linkage of two or more proteins or fragments thereof via their individual peptide backbones, most preferably through genetic expression of a polynucleotide molecule encoding those proteins. It is preferred that the proteins or fragments thereof are from different sources. Thus, preferred fusion proteins include an interferon-beta-1a protein or fragment covalently linked to a second moiety that is not an interferon. Specifically, an "interferon-beta/Ig fusion" is a protein comprising an interferon beta molecule of the invention (i.e., interferon-beta-1a), or fragment thereof whose N-terminus or C-terminus is linked to an N-terminus of an immunoglobulin chain wherein a portion of the N-terminus of the immunoglobulin is replaced with the interferon beta. A species of interferon-beta/Ig fusion is an "interferon-beta/Fc fusion" which is a protein comprising an interferon beta molecule of the invention (i.e., interferon-beta-1a) linked to at least a part of the constant domain of an immunoglobulin. A preferred Fc fusion comprises an interferon beta molecule of the invention linked to a fragment of an antibody containing the C terminal domain of the heavy immunoglobulin chains.

Also, the term "fusion protein" means an interferon beta protein chemically linked via a mono- or hetero-functional molecule to a second moiety that is not an interferon beta protein and is made de novo from purified protein as described below.

"Recombinant," as used herein, means that a protein is derived from recombinant, mammalian expression systems. Protein expressed in most bacterial cultures, e.g., E. coli, will be free of glycan so these expression systems are not preferred. Protein expressed in yeast may have oligosaccharide structures that are different from that expressed in mammalian cells.

"Biologically active," as used throughout the specification as a characteristic of interferon-beta 1a, means that a particular molecule shares sufficient amino acid sequence homology with the embodiments of the present invention disclosed herein to be capable of antiviral activity as measured in an in vitro antiviral assay of the type shown in Example 1, as described below.

A "therapeutic composition" as used herein is defined as comprising the proteins of the invention and other physiologically compatible ingredients. The therapeutic composition may contain excipients such as water, minerals and carriers such as protein.

"amino acid"—a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

A "derivatized" amino acid is a natural or nonnatural amino acid in which the normally occurring side chain or end group (or sugar moiety in the case of interferon-beta-1a) is modified by chemical reaction. Such modifications include, for example, gamma-carboxylation, beta-carboxylation, pegylation, sulfation, sulfonation, phosphorylation, amidization, esterification, N-acetylation, carbobenzylation, tosylation, and other modifications known in the art. A "derivatized polypeptide" is a polypeptide containing one or more derivatized amino acids and/or one or more derivatized sugars, if the polypeptide is glycosylated.

"protein"—any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

"functional equivalent" of an amino acid residue is an amino acid having similar physico-chemical properties as the amino acid residue that was replaced by the functional equivalent.

"mutant"—any change in the genetic material of an organism, in particular any change (i.e., deletion, substitution, addition, or alteration) in a wild-type polynucleotide sequence or any change in a wild-type protein. The term "mutein" is used interchangeably with "mutant".

"wild-type"—the naturally-occurring polynucleotide sequence of an exon of a protein, or a portion thereof, or protein sequence, or portion thereof, respectively, as it normally exists in vivo.

"standard hybridization conditions"—salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 µg/ml denatured, sonicated salmon sperm DNA at 65° C. for 12–20 hours, and washing with 75 mM NaCl/7.5 mM sodium citrate (0.5×SSC)/1% SDS at 65° C. Lower stringency conditions may, for example, include hybridizing with plaque screen buffer, 10% dextran sulfate and 110 µg/ml denatured, sonicated salmon sperm DNA at 55° C. for 12–20 hours, and washing with 300 mM NaCl/30 mM sodium citrate (2.0×SSC)/1% SDS at 55° C. See also Current Protocols in Molecular Biology, John Wiley & Sons, Inc. New York, Sections 6.3.1–6.3.6, (1989).

"expression control sequence"—a sequence of polynucleotides that controls and regulates expression of genes when operatively linked to those genes.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the polynucleotide sequence under the control of the expression control sequence and production of the desired polypeptide encoded by the polynucleotide sequence.

"expression vector"—a polynucleotide, such as a DNA plasmid or phage (among other common examples) which allows expression of at least one gene when the expression vector is introduced into a host cell. The vector may, or may not, be able to replicate in a cell.

"Isolated" (used interchangeably with "substantially pure")—when applied to nucleic acid i.e., polynucleotide sequences, that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) chemically synthesized; (iii) recombinantly produced by cloning; or (iv) purified, as by cleavage and gel separation.

Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional sequences.

"Isolated" (used interchangeably with "substantially pure")—when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature. By "isolated" it is further meant a protein that is: (i)

chemically synthesized; or (ii) expressed in a host cell and purified away from associated proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"heterologous promoter"—as used herein is a promoter which is not naturally associated with a gene or a purified nucleic acid.

"Homologous"—as used herein is synonymous with the term "identity" and refers to the sequence similarity between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The percentage homology between two sequences is a function of the number of matching or homologous positions shared by the two sequences divided by the number of positions compared×100. For instance, if 6 of 10 of the positions in two sequences are matched or are homologous, then the two sequences are 60% homologous. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., *J. Mol Biol.* 48: 443–453 (1970), implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354–352, Nat. Biomed. Res. Foundation, Washington, D.C. (1978).

The terms "polynucleotide sequence" and "nucleotide sequence" are also used interchangeably herein.

The terms "neovascularization" and "angiogenesis" mean, in their broadest sense, the recruitment of new blood vessels. In particular, "angiogenesis" also refers to the recruitment of new blood vessels at a tumor site.

"IFNAR2", "IFNAR1", "IFNAR1/2" refer to the proteins knows to compose the cell surface type I interferon receptor. The extracellular portion (ectodomain) portion of the IFNAR2 chain alone can bind interferon alpha or beta.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I–IV (D. M. Weir and C. C. Blackwell, eds.), 1986; Manipulating the Mouse Embryo, Cold Spring Harbor Laboratory Press, 1986.

II. Production and Expression of Fusion Proteins

The present invention relates to a system for the generation of interferon-beta-1a fusion proteins. In particular, the present invention relates to these proteins as well as the recombinant DNA molecules utilized in their production.

The production of the polypeptides of this invention may be achieved by a variety of methods known in the art. For example, full length interferon-beta-1a or truncated forms of interferon-beta-1a may be produced by known recombinant DNA techniques using cDNAs (see below).

A gene which encodes the desired interferon-beta-1a polypeptide may be designed based on the amino acid sequence of the desired polypeptide. Standard methods may then be applied to synthesize the gene. For example, the amino acid sequence may be used to construct a back-translated gene. A DNA oligomer containing a nucleotide sequence capable of coding for interferon-beta-1a may be made in a single step. Alternately, several smaller oligonucleotides coding for portions of the desired interferon-beta-1a may be synthesized and then ligated together. Preferably, the DNA sequence encoding the interferon-beta-1a moiety will be made as several separate oligonucleotides which are subsequently linked together. (See Example 2). The individual oligonucleotides typically contain 5' or 3' overhangs for complementarity assembly.

Once assembled, preferred genes will be characterized by sequences that are recognized by restriction endonucleases (including unique restriction sites for direct assembly into a cloning or expression vector), preferred codons taking into consideration the host expression system to be used (preferably a mammalian cell), and a sequence which, when transcribed, produces a stable, efficiently translated RNA. Proper assembly may be confirmed by nucleotide sequencing, restriction mapping, and expression of a biologically active polypeptide in a suitable host.

Mammalian interferon beta cDNAs may be isolated by using an appropriate human interferon beta DNA sequence as a probe for screening a particular mammalian cDNA library by cross-species hybridization. Mammalian interferon beta used in the present invention includes, by way of example, primate, human, murine, canine, feline, bovine, equine and porcine interferon beta. Mammalian interferon beta can be obtained by cross species hybridization, using a single stranded cDNA derived from the human interferon beta DNA sequence as a hybridization probe to isolate interferon beta cDNAs from mammalian cDNA libraries. Among the methods that can be used for isolating and cloning interferon gene sequences are those methods found in the U.S. Patents summarized above. Of particular relevance, however, are the teachings of U.S. Pat. No. 4,738,931 (Apr. 19, 1988) describing DNA containing a human interferon beta gene.

The present invention also related to recombinant DNA molecules comprising the aforementioned DNA sequences. The recombinant DNA molecules of this invention are capable of directing expression of the polypeptides of the invention in hosts transformed therewith. A DNA sequence encoding a fusion polypeptide of the invention must be operatively linked to an expression control sequence for such expression. To provide for adequate transcription of the recombinant constructs of the invention, a suitable promoter/enhancer sequence may preferably be incorporated into the recombinant vector, provided that the promoter/expression control sequence is capable of driving transcription of a nucleotide sequence encoding a glycosylated interferon beta. Promoters which may be used to control the expression of the immunoglobulin-based fusion protein include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene enhancers or promoters which are active in pancreatic beta cells (Hanahan, 1985, Nature 315:115–122); immunoglobulin gene enhancers or promoters which are active in lymphoid cells (Grosschedl et al., 1984, Cell 38:647–658; Adames et al., 1985, Nature 318:533–538; Alexander et al., 1987, Mol. Cell. Biol. 7:1436–1444); the cytomegalovirus early promoter and enhancer regions (Boshart et al., 1985, Cell 41:521–530); mouse mammary tumor virus control region which is active in testicular, breast, lymphoid and mast cells (Leder et al., 1986, Cell 45:485–495); albumin gene control region which is active in liver (Pinkert et al., 1987, Genes and Devel. 1:268–276); alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171); beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286); and gonadotropic releasing hormone gene control region which is active in the hypothalamus (Mason et al., 1986, Science 234:1372–1378). Prokaryotic expression systems such as the LAC, or beta-lactamase promoter (Villa-Kamaroff, et al., 1978, Proc. Natl. Acad. Sci. U.S.A. 75:3727–3731) are not presently preferred inasmuch as the expressed interferon beta will not be glycosylated. Nevertheless, prokaryotic expression systems that will allow glycosylation of interferon beta in either prokaryotic or eukaryotic hosts are encompassed within the scope of the invention.

The expression vectors which can be used include, but are not limited to, the following vectors or their derivatives: human or animal viruses such as vaccinia virus, adenovirus or retroviral based vectors; insect viruses such as baculovirus; yeast vectors; bacteriophage vectors (e.g., lambda), and plasmid and cosmid DNA vectors, to name but a few. Specifically, useful expression vectors for the preferred eukaryotic hosts include vectors comprising expression control sequences from SV40, bovine papillomavirus, cytomegalovirus. Further, within each specific expression vector, various sites may be selected for insertion of these DNA sequences. These sites are usually designated by the restriction endonuclease which cuts them. They are well-recognized by those of skill in the art. It will be appreciated that a given expression vector useful in this invention need not have a restriction endonuclease site for insertion of the chosen DNA fragment. Instead, the vector may be joined by the fragment by alternate means.

The expression vector, and the site chosen for insertion of a selected DNA fragment and operative linking to an expression control sequence, is determined by a variety of factors such as: the number of sites susceptible to a particular restriction enzyme, the size of the polypeptide, how easily the polypeptide is proteolytically degraded, and the like. The choice of a vector and insertion site for a given DNA is determined by a balance of these factors.

The recombinant constructs of the invention may be introduced into host cells which are capable of expressing the fusion protein using any method known in the art, including transformation (for example, using DEAE-dextran or calcium phosphate techniques), transfection, microinjection, infection, cell gun, and electroporation. Any host cell type may be utilized provided that the fusion protein recombinant nucleic acid sequences would be adequately transcribed into mRNA in that cell type and the cell can glycosylate the protein. In addition, the recombinant nucleic acid constructs of the invention may be used to create non-human transgenic animals capable of producing the immunoglobulin based fusion protein. In preferred embodiments of the invention, the host cell is a mammalian cell, such as a COS or CHO cell.

Successful incorporation of these polynucleotide constructs into a given expression vector may be identified by three general approaches: (a) DNA—DNA hybridization, (b) presence or absence of "marker" gene functions, and (c) expression of inserted sequences. In the first approach, the presence of the interferon-beta-1a gene inserted in an expression vector can be detected by DNA—DNA hybridization using probes comprising sequences that are homologous to the inserted fusion protein gene. In the second approach, the recombinant vector/host system can be identified and selected based upon the presence or absence of certain "marker" gene functions (e.g., thymidine kinase activity, resistance to antibiotics such as G418, transformation phenotype, occlusion body formation in baculovirus, etc.) caused by the insertion of foreign genes in the vector. For example, if the polynucleotide is inserted so as to interrupt a marker gene sequence of the vector, recombinants containing the insert can be identified by the absence of the marker gene function. In the third approach, recombinant expression vectors can be identified by assaying the foreign gene product expressed by the recombinant vector.

Such assays can be based, for example, on the physical or functional properties of the gene product in bioassay systems.

It will be appreciated that not all host/expression vector combinations will function with equal efficiency in expressing DNA sequences encoding the polypeptides of this invention. However, a particular selection of a host-expression vector combination may be made by those of skill in the art after due consideration of the principles set forth herein without departing from the scope of the invention.

The preferred embodiment of the invention contemplates fusion proteins and DNA sequences coding for them. These fusion proteins have an amino-terminal region characterized by the amino acid sequence of interferon-beta-1a and a carboxy-terminal region comprising a domain of a protein other than interferon-beta-1a. A preferred generic formula for such a protein is a protein having a primary amino acid sequence X-Y-Z, wherein X is a polypeptide having the amino acid sequence, or portion thereof, consisting of the amino acid sequence of human interferon beta; Y is an optional linker moiety; and Z is a polypeptide comprising at least a portion of a polypeptide other than human interferon beta. In one embodiment, moiety Z can be a portion of a polypeptide that contains immunoglobulin-like domains. Examples of such other polypeptides include CD1, CD2, CD4, and members of class I and class II major histocompatability antigens. See U.S. Pat. No. 5,565,335 (Capon et al.) for examples of such polypeptides.

Moiety Z can include, for instance, a plurality of histidine residues or, preferably, the Fc region of an immunoglobulin, "Fc" defined herein as a fragment of an antibody containing the C terminal domain of the heavy immunoglobulin chains.

In the most preferred fusion proteins, the interferon-beta-1a polypeptide is fused via its C-terminus to at least a portion of the Fc region of an immunoglobulin. The interferon-beta-1a forms the amino-terminal portion, and the Fc region forms the carboxy terminal portion. In these fusion proteins, the Fc region is preferably limited to the constant domain hinge region and the CH2 and CH3 domains. The Fc region in these fusions can also be limited to a portion of the hinge region, the portion being capable of forming intermolecular disulfide bridges, and the CH2 and CH3 domains, or functional equivalents thereof. These constant regions may be derived from any mammalian source (preferably human) and may be derived from any appropriate class and/or isotype, including IgA, IgD, IgM, IgE and IgG1, IgG2, IgG3 and IgG4.

Recombinant nucleic acid molecules which encode the Ig fusions may be obtained by any method known in the art (Maniatis et al., 1982, Molecular Cloning; A Laboratory Manual, Cold Spring Harbor Laboratory, Cold Spring Harbor, N.Y.) or obtained from publicly available clones. Methods for the preparation of genes which encode the heavy or light chain constant regions of immunoglobulins are taught, for example, by Robinson, R. et al., PCT Application, Publication No. WO87-02671. The cDNA sequence encoding the interferon molecule or fragment may be directly joined to the cDNA encoding the heavy Ig contant regions or may be joined via a linker sequence. In further embodiments of the invention, a recombinant vector system may be created to accommodate sequences encoding interferon beta in the correct reading frame with a synthetic hinge region. Additionally, it may be desirable to include, as part of the recombinant vector system, nucleic acids corresponding to the 3' flanking region of an immunoglobulin gene including RNA cleavage/polyadenylation sites and downstream sequences. Furthermore, it may be desirable to engineer a signal sequence upstream of the immunoglobulin fusion protein-encoding sequences to facilitate the secretion of the fused molecule from a cell transformed with the recombinant vector.

The present invention provides for dimeric fusion molecules as well as monomeric or multimeric molecules comprising fusion proteins. Such multimers may be generated by using those Fc regions, or portions thereof, of Ig molecules which are usually multivalent such as IgM pentamers or IgA dimers. It is understood that a J chain polypeptide may be needed to form and stabilize IgM pentamers and IgA dimers. Alternatively, multimers of interferon-beta-1a fusion proteins may be formed using a protein with an affinity for the Fc region of Ig molecules, such as Protein A. For instance, a plurality of interferon-beta-1a/immunoglobulin fusion proteins may be bound to Protein A-agarose beads.

These polyvalent forms are useful since they possess multiple interferon beta receptor binding sites. For example, a bivalent soluble interferon-beta-1a may consist of two tandem repeats of amino acids 1 to 166 of SEQ ID NO: 2 (or those encoded by nucleic acids numbered 1 to 498 of SEQ. ID. NO:1) (moiety X in the generic formula) separated by a linker region (moiety Y), the repeats bound to at least a portion of an immunoglobulin constant domain (moiety Z). Alternate polyvalent forms may also be constructed, for example, by chemically coupling interferon-beta-1a/Ig fusions to any clinically acceptable carrier molecule, a polymer selected from the group consisting of Ficoll, polyethylene glycol or dextran using conventional coupling techniques. Alternatively, interferon-beta-1a may be chemically coupled to biotin, and the biotin-interferon beta Fc conjugate then allowed to bind to avidin, resulting in tetravalent avidin/biotin/interferon beta molecules. Interferon-beta-1a/Ig fusions may also be covalently coupled to dinitrophenol (DNP) or trinitrophenol (TNP) and the resulting conjugate precipitated with anti-DNP or anti-TNP-IgM, to form decameric conjugates with a valency of 10 for interferon beta receptor binding sites.

The interferon-beta-1a proteins, fragments, and fusion proteins of the invention may be isolated and purified in accordance with conventional conditions, such as extraction, precipitation, chromatography, affinity chromatography, electrophoresis or the like. For example, the interferon proteins and fragments may be purified by passing a solution thereof through a column having an interferon receptor immobilized thereon (see U.S. Pat. No. 4,725,669). The bound interferon molecule may then be eluted by treatment with a chaotropic salt or by elution with aqueous acetic acid. The immunoglobulin fusion proteins may be purified by passing a solution containing the fusion protein through a column which contains immobilized protein A or protein G which selectively binds the Fc portion of the fusion protein. See, for example, Reis, K. J., et al., J. Immunol. 132:3098–3102 (1984); PCT Application, Publication No. WO87/00329. The chimeric antibody may then be eluted by treatment with a chaotropic salt or by elution with aqueous acetic acid.

Alternatively the interferon proteins and immunoglobulin-fusion molecules may be purified on anti-interferon antibody columns, or on anti-immunoglobulin antibody columns to give a substantially pure protein. By the term "substantially pure" is intended that the protein is free of the impurities that are naturally associated therewith. Substantial purity may be evidenced by a single band by electrophoresis.

An example of a useful interferon-beta-1a/Ig fusion protein of this invention is that of SEQ ID NO: 2, which is secreted into the cell culture by eukaryotic cells containing the expression plasmid pCMG261 (See Example 2). This protein consists of the mature human interferon-beta-1a fused to a portion of the hinge region and the CH2 and CH3 constant domains of murine Ig. This contains a sufficient portion of the murine immunoglobulin to be recognized by the Fc binding protein, Protein A.

Other fusion proteins of the invention incorporating human interferon-beta-1a are shown: (a) in SEQ ID NOS: 3 and 4 for the cDNA and deduced amino acids sequences, respectively of a his tagged-interferon-beta-1a fusion (also shown in FIG. 1) and; (b) in SEQ NO: 1 for the cDNA encoding the interferon-beta-1a/Ig fusion protein of SEQ ID NO: 2 (also shown in FIG. 2).

The preferred interferon-beta-1a proteins of the invention include the novel "junction" DNA sequence SEQ ID NO: 5 and amino acid SEQ ID NO: 6. SEQ ID NO: 5 represents the 11 triplet codons on either side of the junction between human interferon beta DNA and the DNA encoding a human immunoglobulin constant region (see Example 5: SEQ ID NOS: 41 and 42). Specifically, in SEQ ID NO: 5, the DNA encoding human interferon-beta-1a ends at nucleotide triplet 568–570 (AAC) and DNA encoding a human IgG1 constant region starts at the triplet (GAC) beginning with nucleotide number 574 of SEQ ID NO: 41. The corresponding deduced amino acid "junction" sequence is represented in SEQ ID NO: 6 and is based on SEQ ID NO: 42. Another unique "junction" sequence is defined that includes a linker sequence in the final DNA construct (See Example 5: SEQ ID NOS: 43 and 44). This "junction" DNA and amino acid sequence are represented in SEQ ID NO: 7 and 8, respectively, which shows the 11 triplet codons on either side of the junction directly between the end of the interferon-beta-1a sequence (nucleotide number 570 in SEQ ID NO: 43) and the linker sequence (nucleotides 571 to 585 in SEQ ID NO:43; GGGGS in SEQ ID NO: 8).

The DNA "junction" sequences can be used as DNA probes and may be the minimum DNA needed for hybridization under standard conditions to any DNA sequence encoding any interferon-beta-1a/Ig fusion protein. Nevertheless, provided that the whole probe hybridizes to both sides of the junction and both sides of the interferon beta/constant region junction participate in the hybridization, smaller sequences may exist. Furthermore, persons having ordinary skill in the art will understand that DNA sequences larger than SEQ ID NO:5 or 7 will be suitable for hybridization as well. One of ordinary skill in the art can test if a particular probe such as SEQ ID NO: 5 or 7 are capable of hybridizing on both sides of the junction by labelling the 5' end of either a single strand sense oligonucleotide or a single strand anti-sense oligonucleotide with an appropriately labelled phosphate of ATP using polynucleotide kinase. A sequence of the invention must hybridize to, and thus be labelled by both oligonucleotide probes. It is further understood that the invention encompasses fully degenerate sequences encoding the junction SEQ ID NO: 5 or 7.

III. Other Variants of Interferon Fusion Polypeptides

Derivatives of proteins of the invention also include various structural forms of the primary protein which retain biological activity. Due to the presence of ionizable amino and carboxyl groups, for example, interferon beta fusion protein may be in the form of acidic or basic salts, or may be in neutral form. Individual amino acid residues may also be modified by oxidation or reduction. Further, the primary amino acid structure (including the N- and/or C-terminal ends) or the glycan of the interferon-beta-1a may be modified ("derivatized") by forming covalent or aggregative conjugates with other chemical moieties, such as glycosyl groups, polyalkylene glycol polymers such as polyethylene glycol (PEG: see co-pending and commonly assigned application Serial Nos. 60/104,491 and 60/720,237), lipids, phosphate, acetyl groups and the like, or by creating amino acid sequence mutants.

Other derivatives of interferon beta/Ig include covalent or aggregative conjugates of interferon beta or its fragments with other proteins or polypeptides, such as by synthesis in recombinant culture as additional N-termini, or C-termini. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast alpha-factor leader). Interferon beta receptor proteins can comprise peptides added to facilitate purification or identification of interferon beta (e.g., histidine/interferon-beta-1a fusions). The amino acid sequence of interferon beta can also be linked to the peptide Asp-Tyr-Lys-Asp-Asp-Asp-Asp-Lys (DYKDDDDK; SEQ ID NO: 61) (Hopp et al., Bio/Technology 6:1204,1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing.

Other analogs include interferon beta fusion Fc protein or its biologically active fragments whose interferon beta sequences differ from those shown in SEQ ID NOS: 2, 4,6 or 8 by one or more conservative amino acid substitutions or by one or more non conservative amino acid substitutions, or by deletions or insertions which do not abolish the isolated protein's biological activity. Conservative substitutions typically include the substitution of one amino acid for another with similar characteristics such as substitutions within the following groups: valine, alanine and glycine; leucine and isoleucine; aspartic acid and glutamic acid; asparagine and glutamine; serine and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Other conservative substitutions can be readily known by workers of ordinary skill. For example, for the amino acid alanine, a conservative substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions that may be expected to induce changes in the functional properties of isolated polypeptides are those in which: (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. Included in the invention are isolated molecules that are: allelic variants, natural mutants, induced mutants, proteins encoded by DNA that hybridize under high or low stringency conditions to a nucleic acid which encodes a polypeptide such as SEQ. ID. NOS.2, 4, 6 or 8.

We developed interferon-beta-1a mutants that are further variants of the interferon-beta-1a moiety of the invention. These interferon-beta-1a moieties may be particularly useful inasmuch as they display novel properties not found in the wild type interferon-beta-1a (See Example 1). Briefly, we undertook a mutational analysis of human interferon-beta-1a with the aim of mapping residues required for activity and receptor binding. The availability of the 3-D crystal structure of human interferon-beta-1a (see Karpusas et al., 1997, Proc. Natl. Acad. Sci. 94: 11813–11818) allows us to identify, for alanine (or serine) substitutions, the solvent-exposed residues available for interferon beta receptor interactions, and to retain amino acids involved in intramolecular bonds. A panel of fifteen alanine scanning mutations were designed that replaced between two and eight residues along distinct regions each of the helices (A, B, C, D, E) and loops (AB1, AB2, AB3, CD1, CD2, DE1, DE2) of interferon-beta-1a. See Example 1.

An amino-terminal histidine tag ("his" tag) was included for affinity purification of mammalian cell expressed mutants (SEQ ID NO: 2: FIG. 1). Functional consequences of these mutations were assessed in antiviral and antiproliferation assays. A non-radioactive binding assay was developed to analyze these mutants for their binding to the interferon beta surface cell receptor (IFNAR1/2 cell surface receptor). In addition, an ELISA-based assay employing an IFNAR2-ectodomain/Fc fusion protein to bind interferon was used to map interactions of surfaces between interferon-beta-1a and IFNAR2 (See Example 1). These mutational analyses demonstrated that N- and C-termini lie in a portion of the interferon-beta molecule not important for receptor binding or biological function.

We have identified three types of effects that were caused by targeted mutagenesis. These effects may be advantageous for interferon drug development under certain circumstances. The three types of effect are as follows: (a) mutants with higher antiviral activity than that of his-wild-type interferon-beta-1a (e.g. mutant C1); (b) mutants which display activity in both antiviral and antiproliferation assays, but for which antiproliferation activity is disproportionately low with respect to antiviral activity, compared to his-wild-type interferon-beta-1a (e.g., mutants C1, D and DE1); and (c) functional antagonists (e.g., A1, B2, CD2 and DE1), which show antiviral and antiproliferative activities that are disproportionately low with respect to receptor binding, compared to his-wild-type interferon-beta-1a.

Moreover, the coupling between the interferon-beta-1a moiety (X) and the second, non-interferon-beta-1a moiety Z (e.g., an Fc region of an immunoglobulin) can also be effected by any chemical reaction that will bind the two molecules together so long as the immunoglobulin and the interferon-beta-1a retain their respective activities. This chemical linkage can include many chemical mechanisms such as covalent binding, affinity binding, intercalation, coordinate binding and complexation. Representative coupling agents (i.e., linkers "Y" in the generic formula) to develop covalent binding between the interferon-beta-1a and immunoglobulin moieties can include organic compounds such as thioesters, carbodiimides, succinimide esters, diisocyanates such as tolylene-2,6-diisocyanate, gluteraldehydes, diazobenzenes and hexamethylene diamines such as bis-(p-diazonium-benzoyl)-ethylenediamine, bifunctional derivatives of imidoesters such as dimethyl adipimidate, and bis-active fluorine compounds such as 1,5-difluoro-2,4-dinitrobenzene. This listing is not intended to be exhaustive of the various classes of chemical coupling agents known in the art. Many of these are commercially available such as N-succinimidyl-3-(2-pyridyldithio) propionate (SPDP), 1-ethyl-3-(3-dimethylamino-propyl) carbodiimide hydrochloride (EDC); 4-succinimidyloxycarbonyl-alpha-methyl-alpha-(2-pyridyl-dithio)-toluene (SMPT: Pierce Chem. Co., Cat. #21558G).

IV. Utility of the Invention

The fusion proteins of this invention can be used in therapeutic compositions whenever interferon beta therapy is called for. These molecules have the normal advantages associated with fusion proteins, particularly Ig fusions; namely an altered pharmacokinetics and pharmacodynamics, leading to increased half life and increased residence time in the vasculature. Moreover, the particularly preferred glycosylated interferon-beta-1a proteins, although similar in structure to interferon beta 1b, are many times more biologically active than the non-glycosylated interferon beta 1b. See Runkel et al., 1998, Pharm. Res. 15: 641–649.

The products of the present invention have been found useful in sustaining the half life of therapeutic interferon-beta 1a, and may for example be prepared for therapeutic administration by dissolving in water or acceptable liquid medium. Administration is by either the parenteral, aerosol, or oral route. Fine colloidal suspensions may be prepared for parenteral administration to produce a depot effect, or by the oral route while aerosol formulation may be liquid or dry powder in nature. In the dry, lyophilized state or in solution formulations, the interferon-beta-1a fusions of the present invention should have good storage stability.

The therapeutic proteins of the present invention may be utilized for the prophylaxis or treatment of any condition or disease state for which the interferon-beta-1a constituent is efficacious. In addition, the fusion proteins of the present invention may be utilized in diagnosis of constituents, conditions, or disease states in biological systems or specimens, as well as for diagnosis purposes in non-physiological systems.

In therapeutic usage, the present invention contemplates a method of treating an animal subject having or latently susceptible to such condition(s) or disease state(s) and in need of such treatment, comprising administering to such animal an effective amount of a fusion protein of the present invention which is therapeutically effective for said condition or disease state. Subjects to be treated by the fusions of the present invention include mammalian subjects and most preferably human subjects. Depending on the specific condition or disease state to be combated, animal subjects may be administered interferon-beta-1a fusion proteins of the invention at any suitable therapeutically effective and safe dosage, as may readily be determined within the skill of the art, and without undue experimentation. Because of the species barriers of Type I interferons, it may be necessary to generate interferon-fusion proteins as described herein with interferons from the appropriate species.

The anti-cell proliferative activity of interferon-beta-1a is well known. In particular, certain of the interferon-beta-1a fusions described herein are useful for treating tumors and cancers such as osteogenic sarcoma, lymphoma, acute lymphocytic leukemia, breast carcinoma, melanoma and nasopharyngeal carcinoma, as well as autoimmune conditions such as fibrosis, lupus and multiple sclerosis. It is further expected that the anti-viral activity exhibited by the fusion proteins, in particular certain of the interferon-beta-1a muteins described herein, may be used in the treatment of viral diseases, such as ECM infection, influenza, and other respiratory tract infections, rabies, and hepatitis. It is also expected that immunomodulatory activities of interferon-beta-1a exhibited by the proteins described herein, may be used in the treatment of autoimmune and inflammatory diseases, such as fibrosis, multiple sclerosis. The ability of interferons to inhibit formation of new blood vessels (angiogenesis or neovascularization) enable proteins of the invention to be used to treat angiogenic diseases such as diabetic retinopathy, retinopathy of prematurity, macular degeneration, corneal graft rejection, neovascular glaucoma, retrolental fibroplasia, rubeosis, and Osler-Webber Syndrome. Moreover, the antiendothelial activity of interferon has been known for some time and one potential mechanism of interferon action may be to interfere with endothelial cell activity by inhibiting the production or efficacy of angiogenic factors produced by tumor cells. Some vascular tumors, such as hemangiomas, are particularly sensitive to treatment with interferon. Treatment with interferon-alpha is the only documented treatment for this disease. It is expected that treatment with the interferon-beta-1a fusion proteins of the invention will offer subtantial pharmaceutical benefits in terms of pharmacokinetics and pharmacodynamics, since the conjugate is expected to remain in the vasculature for a longer period of time than non-conjugated interferons, thus leading to more efficient and effective therapy for use as an anti-angiogenic agent. See Example 9.

The polymer-interferon-beta-1a fusions of the invention may be administered per se as well as in the form of pharmaceutically acceptable esters, salts, and other physiologically functional derivatives thereof. In such pharmaceutical and medicament formulations, the interferon-beta-1a preferably is utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The interferon-beta-1a is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral, nasal, and parenteral administration are preferred.

When the interferon-beta-1a is utilized in a formulation comprising a liquid solution, the formulation advantageously may be administered orally or parenterally. When the interferon-beta-1a is employed in a liquid suspension formulation or as a powder in a biocompatible carrier formulation, the formulation may be advantageously administered orally, rectally, or bronchially.

When the interferon-beta-1a is utilized directly in the form of a powdered solid, the interferon-beta-1a may advantageously be administered orally. Alternatively, it may be administered nasally or bronchially, via nebulization of the powder in a carrier gas, to form a gaseous dispersion of the powder which is inspired by the patient from a breathing circuit comprising a suitable nebulizer device.

The formulations comprising the proteins of the present invention may conveniently be presented in unit dosage forms and may be prepared by any of the methods well known in the art of pharmacy. Such methods generally include the step of bringing the active ingredient(s) into association with a carrier which constitutes one or more accessory ingredients. Typically, the formulations are prepared by uniformly and intimately bringing the active ingredient(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered polymer conjugates with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active conjugate, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of the active conjugate with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Ophthalmic formulations such as eye drops are prepared by a similar method to the nasal spray, except that the pH and isotonic factors are preferably adjusted to match that of the eye.

Topical formulations comprise the conjugates of the invention dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

Accordingly, the present invention contemplates the provision of suitable fusion proteins for in vitro stabilization of interferon-beta 1a in solution, as a preferred illustrative application of non-therapeutic application. The fusion proteins may be employed for example to increase the resistance to enzymatic degradation of the interferon-beta 1a. and provides a means of improving shelf life, room temperature stability, and robustness of research reagents and kits.

The following Examples are provided to illustrate the present invention, and should not be construed as limiting thereof. In particular, it will be understood that the in vivo, animal experiments described herein may be varied, so that other modifications and variations of the basic methodology are possible. For example, in Example 7, one of ordinary skill in the art could use other neopterin assays or could alter the number and kind of primate used. These modifications and variations to the Examples are to be regarded as being within the spirit and scope of the invention.

EXAMPLE 1

Structure/Activity Studies of Human Interferon-beta-1a Using Alanine/Serine Substitution Mutations: Analysis of Receptor Binding Sites and Functional Domains A. Overview An extensive mutational analysis of human interferon-beta-1a (IFN-beta-1a) was undertaken with the aims of mapping residues required for activity and receptor binding. The availability of the 3-D crystal structure of human IFN-beta (Karpusas, M. et al. 1997, Proc. Natl. Acad. Sci. 94: 11813–11818) allowed us to identify for alanine (or serine) substitutions the solvent-exposed residues available for receptor interactions, and to retain amino acids involved in intramolecular bonds. A panel of 15 alanine substitution mutations were designed that replaced between 2 and 8 residues along distinct regions of each of the helices (A, B, C, D, E) and loops (AB, CD, DE). An amino-terminal tag consisting of 6 histidine residues was included for affinity purification, as well as an enterokinase linker sequence site for removal of the amino-terminal extension. The resulting interferons are interchangeably referred to as "his tagged-interferon(IFN)-beta" or $His_6$-interferon-beta" and the like.

Various mutant his tagged-IFN-beta expression plasmids were constructed using a wild type IFN-beta gene construct as a template for mutagenesis. The mutagenesis strategy involved first introducing unique restriction enzyme cleavage sites throughout the wild type his tagged-IFN beta gene, then replacing distinct DNA sequences between the chosen restriction sites with synthetic oligonucleotide duplexes, which encoded the alanine (or serine) substitution mutations. Finally, the mutant IFN genes were subcloned into a plasmid which directed mammalian cell expression in a human 293 kidney cell line.

Functional consequences of these mutations were assessed in antiviral and antiproliferation assays. A non-radioactive IFN binding assay was developed to analyze these mutants in their binding to the surface receptor ("IFNAR1/2 complex") of human Daudi Burkitt's lymphoma cells. In addition, an assay to map interaction surfaces between his-IFN-beta mutants and IFNAR2 was developed that employed a IFNAR2/Fc fusion protein, comprised of the IFN receptor protein IFNAR2 extracellular domain fused to the hinge, CH2 and CH3 domains of human IgG1.

1. Creation of an Interferon Beta Gene as a Template for Mutagenesis

Our strategy to generate IFN-beta alanine (or serine) substituted mutants was to first create a modified IFN-beta gene, which encoded the wild type protein but which carried unique restriction enzyme cleavage sites scattered across the gene. The unique sites were used to exchange wild type sequences for synthetic oligonucleotide duplexes, which encode the mutated codons. In order to obtain an human IFN-beta-1a expression cassette suitable for creation of mutant genes, the IFN-beta cDNA (GenBank accession #E00029) was amplified by PCR. An initial cloning of the IFN-beta gene into plasmid pMJB107, a derivative of pACYC184, see Rose, et. al., 1988, Nucleic Acids Res. 16 (1)355) was necessary in order to perform site-directed mutagenesis of the gene in a plasmid that lacked the specific restriction sites which would be generated through the mutagenesis.

The PCR primers used to subclone the coding sequences of the human IFN-beta gene also allowed us to introduce an enterokinase linker sequence upstream and in frame with the IFN-beta gene (5' PCR primer 5'TTCTCCGGA GACGAT-GATGACAAGATGAGCTACAACTTGCTTGG ATTCCTACAAAGAAGC-3' (SEQ ID NO: 9; "BET-021", and 3' PCR primer 5'-GCCGCTCGAGTTATCAGTTTC GGAGGTAACCTGTAAGTC-3' (SEQ ID NO:10: "BET-022") and flanking restriction enzyme sites (BspEI and Xho I) useful for cloning into plasmid pMJB107 sites. The resulting DNA is refererred to as PCR fragment A.

An efficient signal sequence from the human vascular cell adhesion molecule-I (VCAM-1) signal sequence and a six histidine tag were introduced into the final construct from a second DNA fragment created from pDSW247 (fragment B). Plasmid pDSW247 is a derivative of pCEP4 (Invitrogen, Carlsbad, Calif.) from which the EBNA-1 gene has been deleted, and which carries the VCAM-1 signal sequence (VCAMs) fused upstream and in frame with a six histidine tag. The PCR primers that were used to generate the VCAMss-1/histidine tag cassette moiety were KID-369 (5' PCR primer 5'-AGCTTCCGGGGGCCATCATCATC ATCATCATAGCT-3': SEQ ID NO: 11) and KID-421 (3' PCR primer 5'-CCGGAGCTATGATGATGATGATGATGG CCCCCGGA-3': SEQ ID NO: 12) incorporating flanking restriction enzyme cleavage sites (NotI and BspEI) that allowed excision of the fragment B DNA.

To create a plasmid vector that carried the VCAM-1 signal sequence, his tag and interferon-beta gene we performed a three-way ligation using gel purified DNA fragments from plasmid vector pMJB107 (NotI and XhoI cleaved), PCR fragment A (BspEI and XhoI cleaved) and fragment B (NotI and BspEI cleaved). The ligated plasmid was used to transform either JA221 or XL1-Blue E. coli cells and ampicillin resistant colonies were picked and tested for inserts by restriction map analysis. Maxiprep DNA was made and the sequence of the insert was verified by DNA sequencing. The resulting construct was called pCMG260.

2. Creation of Alanine Substitution Mutants of Human Interferon-beta in pCMG260

The plasmid pCMG260 was used as a template for multiple rounds of mutagenesis (U.S.E. Site Directed Mutagenesis Kit (Boehringer-Mannheim), which introduced unique restriction cleavage sites into positions along the IFN-beta protein coding sequence but did not change the resulting sequence of the protein. The mutagenized plasmids were used to transform either the JA221 or XL1-Blue strains of E. coli and recombinant colonies selected for chloramphenicol resistance. Chloramphenicol resistant colonies were further tested for the presence of the desired unique restriction enzyme site by DNA restriction mapping analysis. The resulting IFN-beta plasmid, pCMG275.8, contained the full set of unique restriction enzyme cleavage sites and the DNA sequence of the gene was verified. The full DNA sequence of the modified, his-tagged interferon beta gene, together with the wild type protein coding sequence, are given in FIG. 1.

The full set of alanine substitution mutations are depicted in Table 1(next page). The names of the mutants specify the structural regions (helices (A (A1 (SEQ ID NO:45), A2 (SEQ ID NO:46)), B (B1 (SEQ ID NO:50), B2 (SEQ ID NO:51), C (C1 (SEQ ID NO:52), C2 (SEQ ID NO:53)), D (SEQ ID NO:56), E (SEQ ID NO:59)) and loops (AB1 (SEQ ID NO:47), E (SEQ ID NO:48), AB3 (SEQ ID NO:49), CD1 (SEQ ID NO:54), CD2 (SEQ ID NO:55), DE1 (SEQ ID NO:57), DE2 (SEQ ID NO:58))) in which the mutations were introduced. The entire panel of alanine (serine) substitutions results in mutation of 65 of the 166 amino acids of human IFN-beta (SEQ ID NO:60).

The panel of mutants was created from pCMG275.8 by replacing segments of DNA between the unique restriction sites with synthetic oligonucleotide duplexes, which carried the genetic coding information depicted in Table 2 (see below). To create the various alanine substitution mutant plasmids, gel purified pCMG275.8 vector (cleaved with the appropriate restriction enzyme, as indicated on the list below for each IFN-beta structural region) and oligonucleotide duplexes (coding strand sequences are shown in Table 2) were ligated together. The ligation mixtures were used to transform the JA221 strain of E. coli and recombinant colonies selected for ampicillin resistance. Ampicillin resistant colonies were tested for the presence of the insertion of the mutations by screening for appropriate restriction enzyme sites. For two mutants (A2 and CD2), the cloning strategy entailed using two duplexes of synthetic oligonucleotides (shown in Table 2), which carry complementary overhanging ends to allow them to ligate to each other and with the vector-IFN-beta backbone in a three-way ligation. The following list illustrates the sites which were used to clone the mutated oligonucleotides from Table 2. The cloning scheme (subsection B) shows the positions of these unique sites on the interferon beta gene.

| A helix  | BspEI to MunI or BgIII to Pst I |
| AB loop  | MunI to PstI or MunI to BsaHI |
| B helix  | BspHI to BsaI or BsaHI to BsaI |
| C helix  | BsaI to XbaI |
| CD loop  | XbaI to BspHI or XbaI to DraIII |
| D helix  | BspHI to DraIII |
| DE loop  | BspHI to PvuI |
| E helix  | PvuI to BstEII |

TABLE 1

Positions of alanine substitution mutations of $^{HU}$IFN-β

```
            1         10        20        30        40        50
            |         |         |         |         |         |
IFN-β  MSYNLLGFLQRSSNFQCQKLLWQLNGRLEYCLKDRMNFDIPEEIKQLQQFQKE
A1     -A-AA--A--A-----------------------------------------
A2     --------------AA-AA--AA-----------------------------
AB1    -------------------------AAA-AA---------------------
AB2    -------------------------------------AA-A--A--------
AB3    ---------------------------------------------AAAAA-AAA
       |_____helix A_____| |_____AB loop_____|

60        70        80        90       100
            |         |         |         |         |
IFN-β  DAALTIYEMLQNIFAIFRQDSSSTGWNETIVENLLANVYHQINHLKTVLEEKLEKE
B1     -----------A--AS----------------------------------
B2     ----------------AAA-------------------------------
C1     -------------------------AS--AA--S----------------
C2     ----------------------------------A---A--AA-------
CD1    ------------------------------------------------AA--AAA
       |_____helix B___| |_____| |_CD loop_

110       120       130       140       150       160
            |         |         |         |         |         |
IFN-β  DFTRGALMSSLHLKRYYGRILHYLKAKEYSHCAWTIVRVEILRNFYRINRLTGYLRN
CD2    AA-A--A--A-----------------------------------------
D      ------------------A-AA--A--------------------------
DE1    -------------------------AA-----------------------
DE2    -------------------------AA-----------------------
E      ----------------------------------A---A--A--A--------
       CD loop_| |____helix D____|  |_____helix E_____|
```

The line designated IFN-β shows the wild type human IFN-β sequence. Alanine or serine substitutions of the IFN-β residues are shown for each of the mutants and dashes, below relevant regions, indicate wild type sequences. The helices and loop structures are indicated as solid lines below the mutants. The DE loop spans the gap between the D and E helices. Two additional alanine substitution mutants (H93A, H97A and H121A) were generated and analyzed in antiviral assays to assess the effects of mutating these histidines, which chelate zinc in the crustal structure dimer. Both of these mutants retained full wild type activity in antiviral assays, suggesting that zinc-mediated dimer formation is not important for IFN-β activity.

TABLE 2

| | | |
|---|---|---|
| A1 | SEQ ID NO: 13 BET-053 | CCGGAGACGATGATGACAAGATGGCTTACGCCGCTCTTGGAGCCCTACAAG CTTCTAGCAATTTTCAGTGTCAGAAGCTCCTGTGGC |
| A2 | SEQ ID NO: 14 BET-039 | GATCTAGCAATGCTGCCTGTGCTGCCCTCCTGGCTGCCTTGAATGGGAGGC TTGAATACT |
| | SEQ ID NO: 15 BET-041 | GCCTCAAGGACAGGATGAACTTTGACATCCCTGAGGAGATTAAGCAGCTGCA |
| AB1 | SEQ ID NO: 16 BET-080 | AATTGAATGGGAGGGCTGCAGCTTGCGCTGCAGACAGGATGAACTTTGACAT CCCTGAGGAGATTAAGCAGCTGCA |
| AB2 | SEQ ID NO: 17 BET-082 | AATTGAATCGGAGGCTTGAATACTGCCTCAAGGACAGGGCTGCATTTGCTAT CCCTGCAGAOATTAAGCAGCTGCA |
| AB3 | SEQ ID NO: 18 BET-084 | AATTGAATGGGAGGCTTGAATACTGCCTCAAGGACAGGATGAACTTTGACA |
| | SEQ ID NO: 19 BET-086 | TCCCTGAGGAGATTGCTCCAGCTOCAGCTTTCGCTGCAGCTGA |
| B1 | SEQ ID NO: 20 BET-110 | CGCCGCGTTGACCATCTATGAGATGCTCGCTAACATCGCTAGCATTTTCAGA CAAGATTCATCTACCACTGGCTGGAA |
| B2 | SEQ ID NO: 21 BET-112 | CGCCGCATTGACCATCTATGAGATGCTCCAGAACATCTTTGCTATTTTCGCT GCAGCTTCATCTAGCACTGGCTGGAA |
| C1 | SEQ ID NO: 22 BET-114 | GGAATGCTTCAATTGTTGCTGCACTCCTGAGCAATGTCTATCATCAGATAAA CCATCTGAAGACAGTTCTAG |
| C2 | SEQ ID NO :23 BET-092 | GGAATGAGACCATTGTTGAGAACCTCCTGGCTAATGTCGCTCATCAGATAGC ACATCTGGCTGCAGTTCTAG |
| CD1 | SEQ ID NO: 24 BET-094 | CTAGCTGCAAAACTGGCTGCAGCTGATTTCACCAGGGGAAAACT |
| CD2 | SEQ ID NO: 25 BET-096 | CTAGAAGAAAAACTGGAGAAACAAGCAGCTACCGCTGCAAAAGCAATGAGCG CGCTGCACCTGAAAAGA |
| | SEQ ID NO: 26 BET-106 | TATTATGGGAGGATTCTCCATTACCTGAAGGCCAAGGAGTACTCACACTGT |
| D1 | SEQ ID NO: 27 BET-108 | CATGAGCAGTCTGCACCTGAAAAGATATTATGGOGCAATTGCTGCATACCT CGCAGCCAAGGAGTACTCACACTGT |
| DE1 | SEQ ID NO: 28 BET-116 | CATGAGCAGTCTGCACCTCAAAAGATATTATGGGAGGATTCTGCATTACCT GAAGGCCGCTGCATACTCACACTGTGCCTGGACGAT |
| DE2 | SEQ ID NO: 29 BET-118 | CATGAGCAGTCTGCACCTGAAAAGATATTATGGGAGGATTCTGCATTACCTG AAGGCAAAGGAGTACGCTGCATCTGCCTGGACGAT |
| E1 | SEQ ID NO: 30 BET-104 | CGTCAGAGCTGAAATCCTAGCAAACTTTGCATTCATTGCAAGACTTACAG |

B. Construction of EBNA 293 expression plasmids

The wild type and mutant IFN-beta genes, fused to the VCAM-1 signal sequence, his tag and enterokinase linker sequence, were gel purified as 761 base pair NotI and BamHI restriction fragments. The purified genes were subcloned into NotI and BamHI cleaved plasmid vector pDSW247, which is a derivative of pCEP4 (Invitrogen, Carlsbad, Calif.). Plasmid pDSW247 is an expression vector for transient expression of protein in human EBNA 293 kidney cells (Invitrogen, Carlsbad, Calif.). It contains the cytomegalovirus early gene promoter and EBV regulatory elements which are required for high level gene expression in that system, as well as selectable markers for *E. coli* (ampicillin resistance) and EBNA 293 cells (hygromycin resistance). The ligated plasmids were used to transform either JA221 or XL1-Blue *E. coli* cells and ampicillin resistant colonies were picked and tested for inserts by restriction map analysis. Maxiprep DNA was made and the sequence of the inserts was verified by DNA sequencing. Positive clones displaying the desired mutagenized sequences were used to transfect human EBNA 293 kidney cells.

Figure 12:
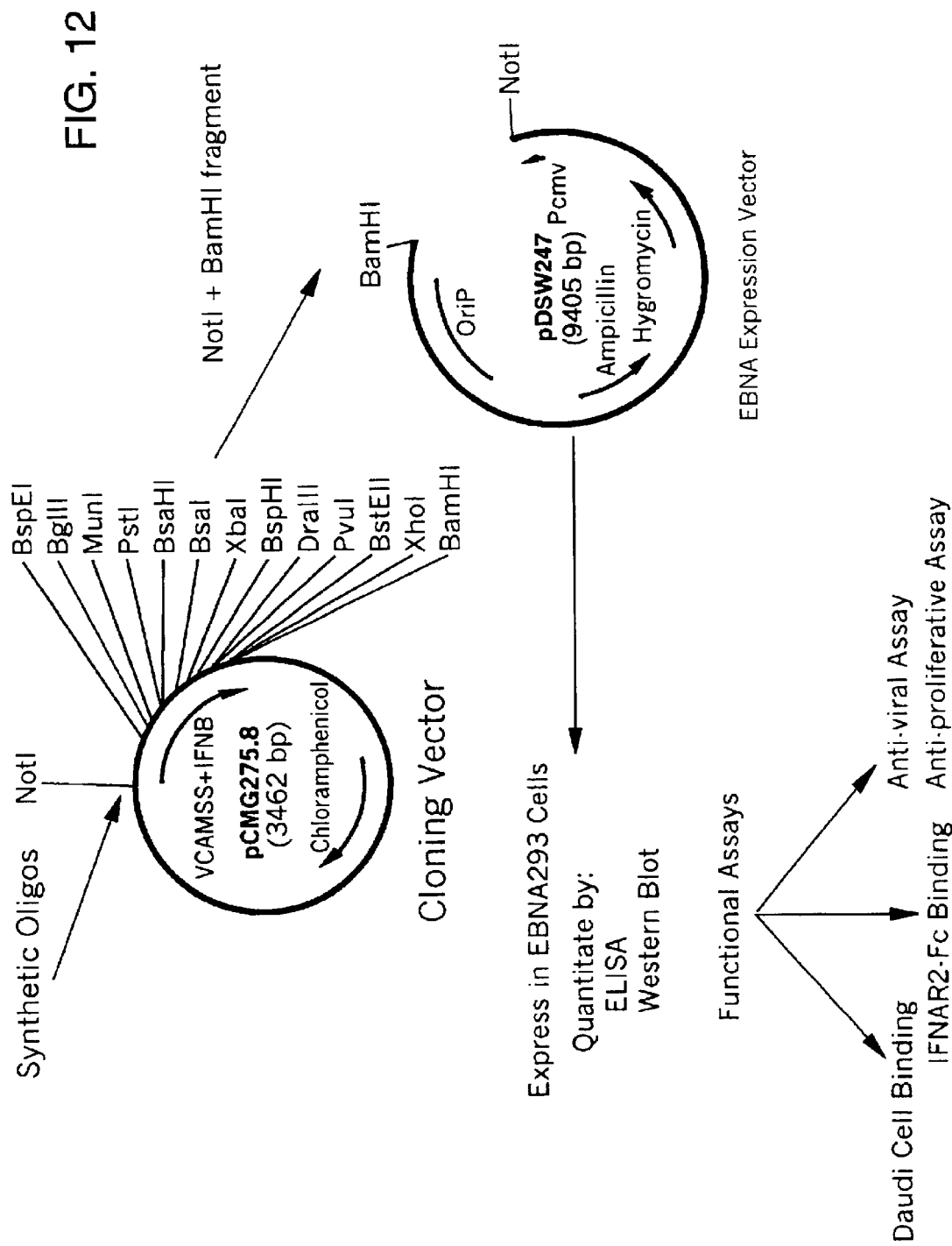
FIG. 12. Schematic representation of overall cloning and expression strategy.

The overall cloning and expression strategy is presented in FIG. 12.

C. Expression and Quantitation of IFN-beta-1a Alanine Substitution Mutants

The human EBNA 293 cells (Invitrogen, Carlsbad, Calif., Chittenden, T. (1989) J. Virol. 63: 3016–3025) were maintained as subconfluent cultures in Dulbecco's Modified Eagle's media supplemented with 10% fetal bovine serum, 2 mM glutamine and 250 $\mu$g/ml Geneticin (Life Technologies, Gaithersburg, Md.). The pDSW247 expression plasmids were transiently transfected into EBNA 293 cells using the lipofectamine protocol (Gibco/BRL, Life Technologies). Conditioned media was harvested 3–4 days posttransfection, cell debris was removed by centrifugation, and the his-IFN-beta concentration was quantitated by ELISA.

The ELISA assay was performed using polyclonal rabbit antibodies (protein A purified IgG, antibodies had been raised to purified human IFN-beta-1a) to coat 96-well ELISA plates and a biotinylated form of the same polyclonal rabbit Ig was used as a secondary reagent to allow interferon detection using streptavidin-linked horseradish peroxidase (HRP: Jackson ImmunoResearch, W. Grove, Pa.). A dilution series of interferon-beta-1a (as AVONEX® sold by Biogen, Inc.) was used to generate standard concentration curves. The his-IFN-beta containing conditioned media from the EBNA transfectants were diluted to obtain samples with concentrations ranging between 10 g/ml and 0.3 ng/ml in the ELISA assay. To confirm the concentrations of the IFN-beta in media determined by ELISA, western blot analysis was performed. Reduced culture supernatants and IFN-beta-1a standards were subjected to SDS-PAGE on 10–20% gradient gels (Novex, San Diego, Calif.) and blotted onto PDVF membranes. Immunoreactive bands were detected with a rabbit polyclonal anti-IFN-beta-1a antiserum (#447, Biogen, Inc., a second antiserum that had been raised against IFN-beta-1a), followed by treatment with HRP-linked donkey anti-rabbit IgG (Jackson ImmunoResearch, W. Grove, Pa.).

D. Assessing the Interferon-Beta Mutants for Receptor Binding

Figure 5:
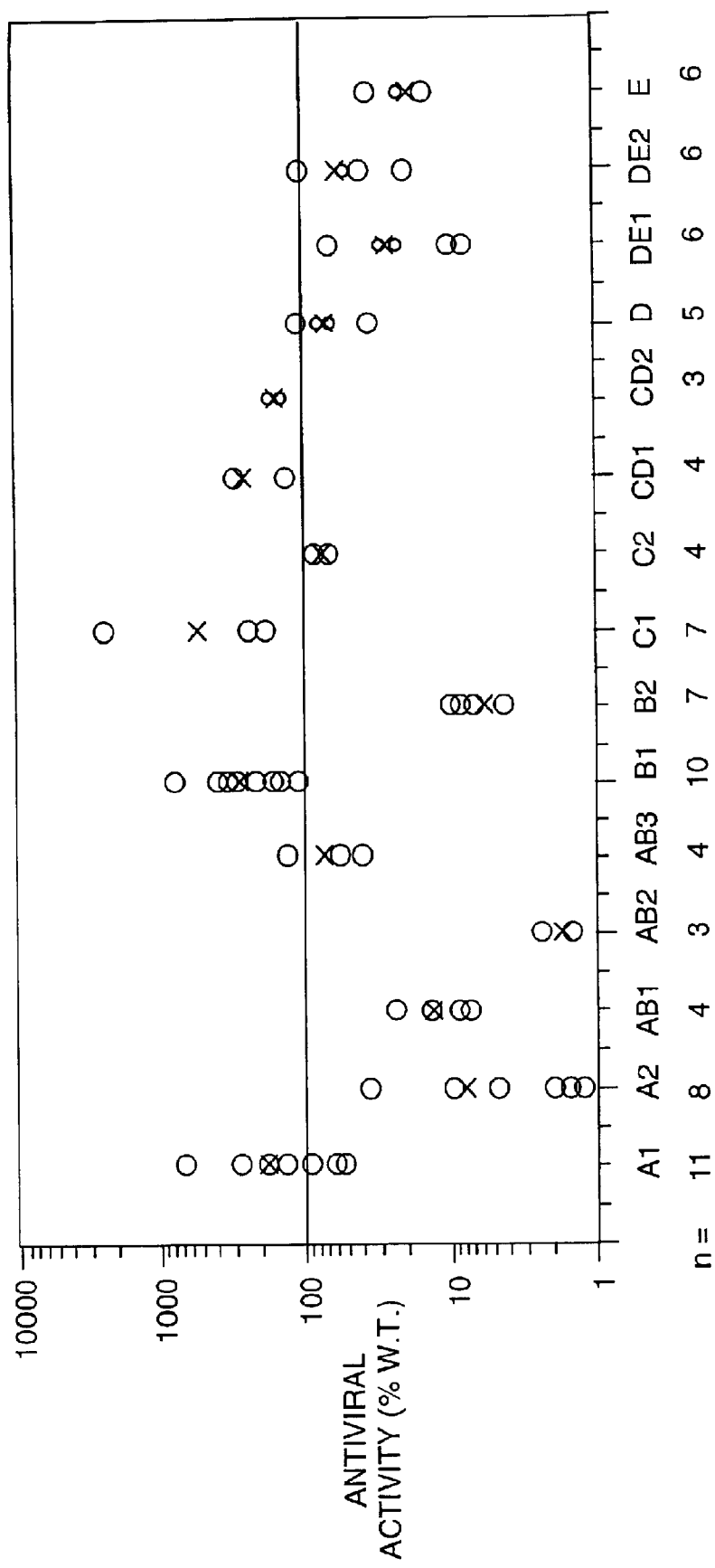

The receptor binding properties of the Interferon-beta mutants described in C were assessed using two different binding assays. One assay measured binding of the interferon-beta mutants to a fusion protein, IFNAR2/Fc, comprising the extracellular domain of the human IFNAR2 receptor chain fused to part of the constant region of a human IgG. IFNAR2-Fc was expressed in chinese hamster ovary (CHO) cells and purified by protein A sepharose affinity chromatography according to the instructions of the manufacturer (Pierce Chem. Co., Rockford, Ill., catalog #20334). The binding of interferon-beta mutants to IFNAR2-Fc was measured in an ELISA format assay. ELISA plates were prepared by coating flat-bottomed 96 well plates overnight at 4° C. with 50 $\mu$l/well of mouse anti-human IgG1 monoclonal antibody (CDG5-AA9, Biogen, Inc.) at 10 $\mu$g/ml in coating buffer (50 mM $NaHCO_3$, 0.2 mM $MgCl_2$, 0.2 mM $CaCl_2$, pH 9.6). Plates were washed twice with PBS containing 0.05% Tween-20, and blocked with 0.5% non-fat dry milk in PBS for 1 hour at room temperature. After two more washes, 50 $\mu$l of 1 $\mu$g/ml IFNAR2-Fc in 0.5% milk in PBS containing 0.05% Tween-20 was added to each well and incubated for 1 hour at room temperature, and the plates were then washed twice more. Binding of the interferon-beta mutants to IFNAR2-Fc was measured by adding 50 $\mu$l/well mutant interferon-beta in conditioned media, serially diluted in Dulbecco's Modified Eagle's Medium (DMEM) supplemented with 10% fetal bovine serum, and incubating for 2 hours at 4° C. Dilutions of interferon-beta mutant typically ranged from approximately 1 $\mu$M down to 10 pM. After washing, interferon-beta bound to the plates was detected by adding 50 $\mu$l/well of a cocktail consisting of a 1:1000 dilution of a rabbit polyclonal anti-interferon antibody (#447, Biogen, Inc.) plus horseradish peroxidase (HRP)-labelled donkey anti-rabbit IgG (Jackson ImmunoResearch), and incubating for 15 minutes at 4° C. After two washes, HRP substrate was added, and the plate was incubated at 4° C. before being read on an ELISA plate reader at an absorbance of 450 nm. Data were plotted as absorbance versus the concentration of mutant interferon-beta, and the affinity for the binding of the mutant interferon-beta to IFNAR2-Fc was determined by fitting the data to a simple hyperbolic binding equation. Results from these analyses are shown in FIG. 3, in which the binding affinity for each mutant, determined in triplicate experiments, is expressed as a percentage of that measured for $His_6$-wild-type interferon-beta-1a.

A second receptor binding assay was used to measure the affinity with which the interferon-beta mutants bound to Daudi cells expressing both receptor chains, IFNAR1 and IFNAR2, which together comprise the receptor for interferon-beta. This FACS-based assay used a blocking monoclonal antibody directed against the extracellular domain of IFNAR1, EA12 (Biogen, Inc.), to distinguish unoccupied (free) receptor from receptor to which interferon-beta was bound. Daudi cells (20 $\mu$l at $2.5\times10^7$ cells/ml) were placed in 96-well V-bottom ELISA plates, and incubated for 1 hour at 4° C. with various concentrations of interferon-beta mutant (20 $\mu$l in FACS buffer; 5% FBS, 0.1% $NaN_3$ in PBS). Desirable serial dilutions of interferon-beta mutants ranged from 0.5 $\mu$M down to 0.5 pM. To each well was added 100 ng of biotinylated murine anti-IFNAR1 monoclonal antibody EA12 (10 $\mu$l), and the plates incubated for an additional 2 minutes at room temperature before being washed twice with FACS buffer (4° C.). The cells were then incubated for 30 minutes at 4° C. with 50 $\mu$l/well of a 1:200 dilution of R-Phycoerythrin-conjugated streptavidin (Jackson ImmunoResearch, West Grove, Pa.), washed twice in FACS buffer, resuspended in 300 $\mu$l FACS buffer containing 0.5% paraformaldehyde, and transferred into 12×75 mm polystyrene tubes (Falcon 2052). The samples were then analyzed by flow cytometry on a FACScan (Becton Dickinson). Data were plotted as mean channel fluorescence intensity (MFCI) versus the concentration of interferon-beta mutant; binding affinities were defined as the concentration of interferon-beta mutant giving 50% inhibition of antibody staining. Each mutant was tested multiple times. FIG. 4 shows the receptor binding affinities for each interferon-beta mutant, determined by this method, expressed as a percentage of the affinity measured for $His_6$-wild-type interferon-beta-1a in each experiment.

E. Assessing the Interferon-Beta Mutants for Function

The interferon-beta mutants were also tested for functional activity using in vitro assays for antiviral activity and for the ability of the interferon-beta to inhibit cell proliferation. A minimum of three antiviral assays, each with triplicate data points, were performed on each mutant. $His_6$-wild-type interferon-beta-1a was included as a reference in every experiment. The antiviral assays were performed by treating A549 human lung carcinoma cells (ATCC CCL 185) overnight with 2-fold serial dilutions of mutant interferon-beta at concentrations that spanned the range between full antiviral protection and no protection from viral cell killing. The following day, the cells were challenged for two days with encephalomyocarditis virus (ECMV) at a dilution that resulted in complete cell killing in the absence of interferon. Plates were then developed with the metabolic dye MTT (2,3-bis[2-Methoxy-4-nitro-5-sulfo-phenyl]-2H-tetrazolium-5-carboxyanilide) (M-5655, Sigma, St. Louis, Mo.). A stock solution of MTT was prepared at 5 mg/ml in PBS and sterile filtered, and 50 μl of this solution was diluted into cell cultures (100 μl per well). Following incubation at room temperature for 30–60 minutes, the MTT/media solution was discarded, cells were washed with 100 μl PBS, and finally the metabolized dye was solubilized in 100 μl 1.2N hydrochloric acid in 90% isopropanol. Viable cells (as evidenced by the presence of the dye) were quantified by absorbance at 450 nm. Data were analyzed by plotting absorbance against the concentration interferon-beta mutant, and the activity of each mutant was defined as the concentration at which 50% of the cells were killed. FIG. 5 shows the activity of each mutant expressed as a percentage of the activity measured for his tagged-wild-type interferon-beta-1a in each experiment.

Figure 6:
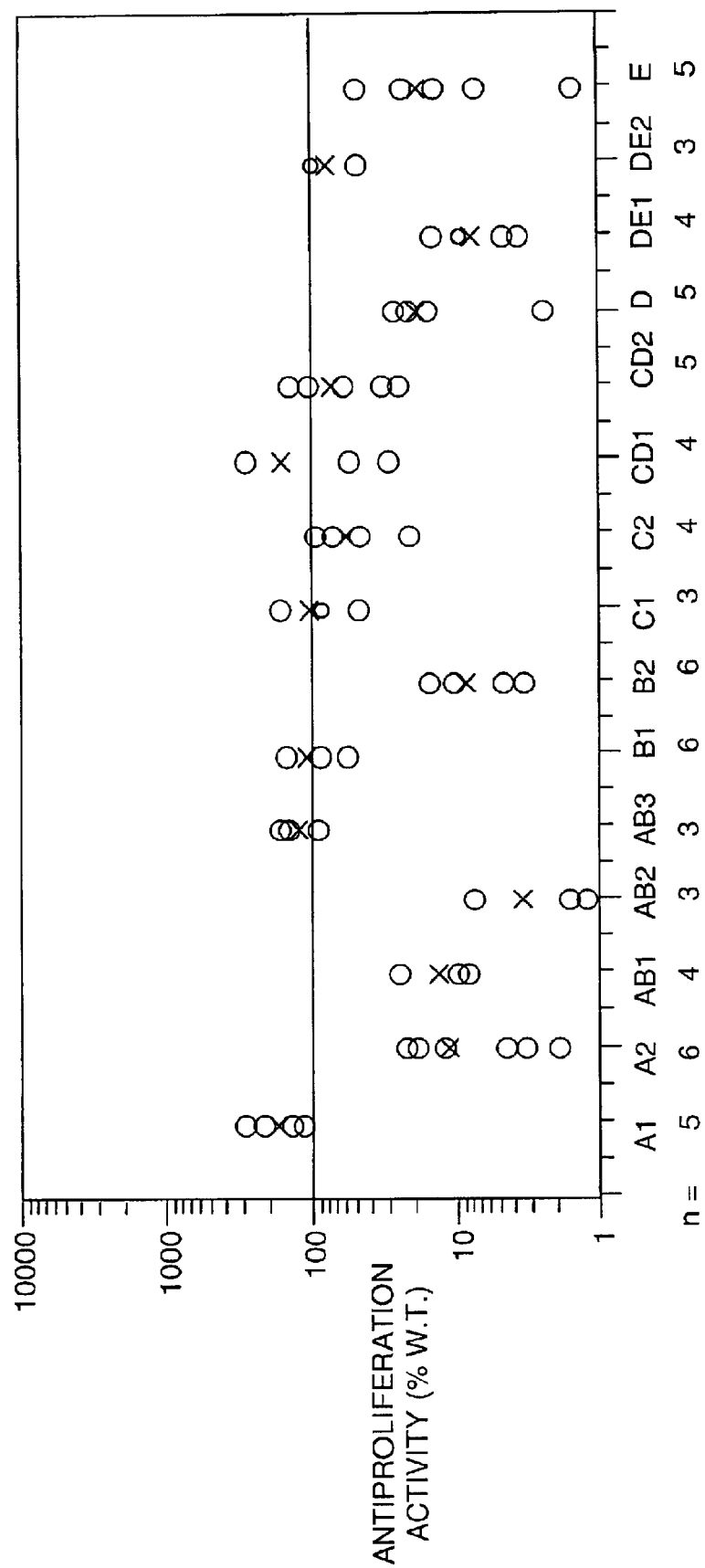
Figure 7:
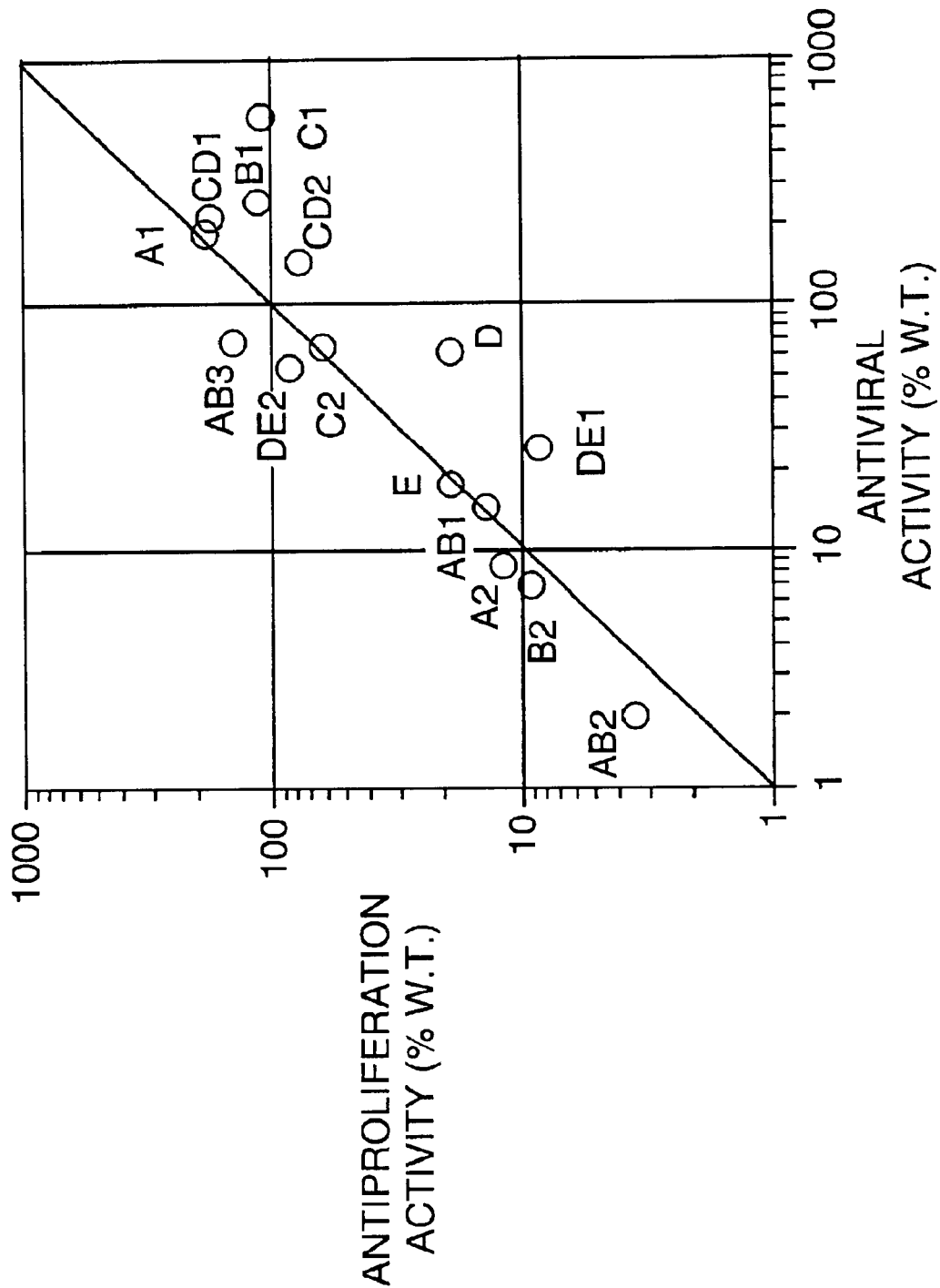

Interferon-beta mutants were also assessed for function in an antiproliferation assay. Human Daudi Burkitt's lymphoma cells (ATCC #CCL 213) were seeded at $2 \times 10^5$ cells/ml in RPMI 1620 supplemented with 10% defined fetal calf serum (Hyclone, Logan Utah), and 2 mM L-glutamine. Each well also contained a given concentration of interferon-beta mutant in a final total volume of 100 μl of medium per well; the interferon-beta concentrations used were chosen to span the range from maximal inhibition of Daudi cell proliferation to no inhibition (i.e. full proliferation). Duplicate experimental points were used for each concentration of interferon-beta mutant tested, and a duplicate set of untreated cells was included in all experiments. Cells were incubated for two days at 37° C. in 5% $CO_2$ incubators, after which 1 μCi per well of tritiated thymidine ((methyl-$^3$H) thymidine, Amersham TRK758) in 50 μl medium was added to each well, and incubated for a further 4 h. Cells were harvested using a LKB plate harvester, and incorporation of tritiated thymidine was measured using a LKB beta plate reader. Duplicate experimental values were averaged and the standard deviations determined. Data were plotted as mean counts per minute versus the concentration of interferon-beta mutant, and the activity of each mutant was defined as the concentration required to give 50% of the maximal observed growth inhibition. Multiple assays for each mutant were performed. FIG. 6 shows the results expressed as a percentage of the activity found for his tagged-wild-type interferon-beta-1a in each experiment.

F. Properties of the Interferon-Beta Mutants

Histidine tagged-wild-type interferon-beta-1a was found to have activities in the antiviral and antiproliferation assays that were each about 3-fold lower than the corresponding activities found for untagged wild-type interferon-beta-1a. Because all of the interferon-beta mutants A1-E contain the identical his tag sequence at their N-termini, the effects of the mutations on the properties of the molecule were determined by comparing the activities of these mutants in the antiviral, antiproliferation and binding assays to the activity observed for his tagged-wild-type interferon-beta-1a. In so doing, we assume that variations in the activities of mutants A1-E, compared to his tagged-wild-type interferon-beta-1a, are qualitatively and quantitatively about the same as the effects that these same mutations would have in the absence of the N-terminal his tag. The equivalent assumption for tagged or fusion constructs of other soluble cytokines is commonly held to be true by practitioners of the technique of alanine scanning mutagenesis, especially when the in vitro functional activity of the tagged or fusion construct is close to that of the wild-type cytokine as is the case here. See, for example, Pearce K. H. Jr, et al., *J. Biol. Chem.* 272:20595–20602 (1997) and Jones J. T., et al., *J. Biol. Chem.* 273:11667–11674 (1998)

The data shown in FIGS. 3–6 suggests three types of effects that were caused by the targeted mutagenesis. These effects may be advantageous for interferon drug development under certain circumstances. The three types of effect are as follows: (a) mutants with higher antiviral activity than that of wild-type interferon-beta-1a (e.g. mutant C1); (b) mutants which display activity in both antiviral and antiproliferation assays, but for which antiproliferation activity is disproportionately low with respect to antiviral activity, compared to wild-type interferon-beta-1a (e.g., mutants C1, D and DE1); and (c) functional antagonists (e.g., A1, B2, CD2 and DE1), which show antiviral and antiproliferative activities that are disproportionately low with respect to receptor binding, compared to wild-type interferon-beta-1a. It can be seen that some mutants fall into more than one class. These classes are reviewed below. While we have characterized these classes of mutants with respect to those examples listed, it should be appreciated that other mutations in these regions may result in similar, or even enhanced effects on activity:

a) Mutant C1 possesses antiviral activity that is approximately 6-fold greater than that of wild-type his-tagged interferon-beta-1a. This mutant and others of this type are predicted to be useful in reducing the amount of interferon-beta that must be administered to achieve a given level of antiviral effect. Lowering the amount of administered protein is expected to reduce the immunogenicity of the protein and may also reduce side-effects from non-mechanism-based toxicities. Mutations in this class are predicted to be advantageous in situations where the therapeutic benefit of interferon-beta administration results from its antiviral effects, and where antiproliferative effects contribute to toxicity or to unwanted side-effects.

(b) The relative activities (% wild type) of the alanine substituted mutants in antiviral and antiproliferation assay are compared in FIG. 7. Coordinately changed activities (i.e. antiviral and antiproliferation activities that differ by the same factor from the activities of the wild-type his tagged-interferon-beta-1a) are seen in most mutants (those lying on the diagonal line). However, several mutants show greater alterations in activity in one assay relative to the other, compared to wild-type his tagged-interferon-beta-1a, as evidenced by displacement from the diagonal. Three such mutants are shown in the Table below. Mutant C1 shows antiviral activity that is ~6-fold higher than that of wild-type his tagged-interferon-beta-1a, but its activity in the antiproliferation assay is similar to that of wild-type. Mutant C1 thus has antiviral activity that is enhanced by a factor of 5.2 over its antiproliferation activity, relative to wild-type his tagged-interferon-beta-1a. Similarly, mutant D displays 65% of wild type activity in the antiviral assay, but only 20% of wild-type activity in the antiproliferation assay, and thus has antiviral activity that is enhanced 3.4-fold over its antiproliferation activity compared to wild type. Mutant DE1 displays 26% of wild type activity in the antiviral assay but only 8.5% in the antiproliferation assay, and thus has antiviral activity that is enhanced 3.0-fold over its antiproliferation activity compared to wild-type his tagged-interferon-beta-1a. When administered at a concentration sufficient to achieve a desired level of antiviral activity, these mutant proteins will show substantially lower levels of antiproliferative activity than the wild-type protein. Mutations in this class, like those in class (a), are predicted to be advantageous in situations where the therapeutic benefit of interferon-beta administration results from its antiviral effects, and where antiproliferative effects contribute to toxicity or to unwanted side-effects.

| Mutant | Antiviral Activity (AV) (% wild type) | Antiproliferative (AP) Activity (% wild type) | AV/AP |
|---|---|---|---|
| C1 | 571 | 109 | 5.2 |
| D | 65 | 19 | 3.4 |
| DE1 | 26 | 8.5 | 3.0 |

(c) Mutants with antiviral and antiproliferative activities that are low with respect to receptor binding, as compared to wild-type his tagged-interferon-beta-1a (see Table below). Mutant A1 displays antiviral and antiproliferative activities that are 2.0-fold and 1.8-fold higher than that observed for wild-type his tagged-interferon-beta-1a, but binds to the cognate receptor on Daudi cells with an affinity that is 29-fold higher than wild-type. The binding of this mutant to the IFN-beta receptor is thus enhanced approximately 15-fold compared to the antiviral and antproliferation activities of the protein. Similarly, mutants B2, CD2 and DE1 show enhancements of binding over antiviral activity of 4.6-, 4.6- and 18-fold, respectively, and over antiproliferation activity of 3.5-, 15- and 54-fold. These proteins are predicted to be useful as functional antagonists of the activity of endogenous IFN-beta, and possibly of other endogenous Type I interferons, because they have the ability to bind to and occupy the receptor, and yet generate only a small fraction of the functional response in the target cells that would be seen with wild type IFN-beta.

| Mutant | Antiviral Activity (AV) (% wt) | Antiproliferative Activity (AP) (% wt) | Cell Binding Activity (% wt) | Binding/AV | Binding /AP |
|---|---|---|---|---|---|
| A1 | 200 | 180 | 2900 | 15 | 16 |
| B2 | 7.1 | 9.2 | 33 | 4.6 | 3.5 |
| CD2 | 150 | 46 | 690 | 4.6 | 15 |
| DE1 | 26 | 8.5 | 460 | 18 | 54 |

G. Mutein Relationship to Three Dimensional Structure of Interferon

While published crystal structures for a non-glycosylated form of murine interferon beta (T. Senda, S. Saitoh and Y. Mitsui. Refined Crystal Structure of Recombinant Murine Interferon-β at 2.15 Å Resolution. *J. Mol. Biol.* 253: 187–207 (1995)) and for human interferon alpha-2b (R. Radhakrishnan, L. J. Walter, A. Hruza, P. Reichert, P. P Trotta, T. L. Nagabhushan and M. R. Walter. Zinc Mediated Dimer of Human Interferon-α2b Revealed by X-ray Crystallography. *Structure.* 4: 1453–1463 (1996)) had provided models for the polypeptide backbone of human interferon beta, we have recently solved the structure for interferon-beta-1a in its glycosylated state (M. Karpusas, M. Nolte, C. B. Benton, W. Meier, W. N. Lipscomb, and S. E Goelz. The Crystal Structure of Human Interferon-β at 2.2 Å resolution. *Proc. Natl. Acad. Sci.* USA 94: 11813–11818 (1997)).

The results of our mutational analyses can be summarized with respect to the 3D-structure of interferon-beta-1a (not presented here). Certain mutatations residues created a reduction in activity (2 to >5 fold reduced). The mutated regions correspond to the substitutions given in Tables 1 and 2.

Mutations that are most significant in their effect on function resulted in a dramatic reduction in both activity and cell surface receptor binding. Mutations in this region (A2 helix, AB& AB2 loop and E helix) correspond to mutations in the IFNAR2 binding site, since none of these mutants bound IFNAR/Fc in our assay.

While those mutations that were important for IFNAR2 binding also affected cell binding, cell surface binding properties are also influenced by residues in other regions of the molecule (B1 helix, C2 helix). It can be seen in the 3-D models (not shown) depicting the effects of the alanine substitution mutants that the N-terminal, C-terminal and the glycosylated C helix regions of the IFN-beta-1a molecule do not lie within the receptor binding site. Mutations in these regions did not reduce biological activity or reduce cell surface receptor binding.

EXAMPLE 2

Construction of Plasmids for Expression of Interferon-beta-1a Fusion (IFN-beta/Fc) Protein PCR technology was employed to create an expression plasmid encoding the human IFN-beta DNA sequence fused to the Fc portion of murine IgG2a heavy chain molecule. The plasmid vector pDSW247 (see Example 1) is a derivative of pCEP4 (Invitrogen, Carlsbad, Calif.), from which the EBNA-1 gene has been deleted. This plasmid was used for the construction of an expression vector useful for transient protein expression in EBNA 293 human kidney cells (Invitrogen, Carlsbad, Calif., Shen. E. S., et. al. 1995, Gene 156, 235–239). It was designed to contain a human vascular cell adhesion molecule-I (VCAM-1) signal sequence in frame and upstream of the interferon beta sequence, and an enterokinase linker sequence at the junction of the interferon beta and Ig sequences.

The fusion protein expression cassette was assembled from several DNA fragments. To obtain a DNA fragment encoding the human IFN-beta gene, the cDNA subclone of human IFN-beta (GenBank accession #E00029) was used as a template for PCR using primers (5'-GGTGGTCTCACATGAGCTACAACTTGCT-TGGATTCCTACAAAGAAGC (SEQ ID NO: 31: "BET-025") and 5'-GCCCTCGAGTCGACCTTGTCATCATCG TCGTTTCGGAGGTAACCTGTAAG (SEQ ID NO: 32: "BET-026") that also incorporated a restriction enzyme cleavage site (BsaI) upstream of the first codon of the IFN-beta. The 3' PCR primer (SEQ ID NO: 32: BET-026) for the IFN-beta gene eliminated the IFN-beta termination codon, and incorporated both an in frame enterokinase linker sequence (DDDDK) and a terminal restriction enzyme site (XhoI), useful for subcloning into the expression vector. The BsaI site introduced upstream of the IFN-beta coding sequence allowed us to ligate the VCAM-1 signal sequence upstream and in frame with the IFN-beta gene coding sequence. This VCAM-1 signal sequence was also generated by PCR using primer pairs 5'-CAAGCTTGCTAGCGGCCGCGG-3' (SEQ ID NO: 33: "BET-023" and 5'-GGTGGTCTCACATGGCTTG AGAAGCTGC-3'(SEQ ID NO: 34: "BET-024") that contained a 5' restriction enzyme cleavage site (NotI, for ligation onto the pDSW247 NotI cloning site) and a 3' restriction enzyme cleavage site (BsaI, for ligation onto the IFN-beta-1a 5' PCR fragment). The template for PCR was the human vascular cell adhesion molecule-1 (VCAM-1) cDNA (GenBank accession number X53051).

To create the IFN-beta-1a/Fc fusion gene the following procedures were performed. The murine IgG2a fragment was removed from pEAG293 by gel purification of a SalI+ BamHI digestion DNA fragment. Plasmsid pEAG293 is a Bluescript IISK+(Stratagene, LaJolla Calif., catalogue #212205) subclone of the hinge, CH2 and CH3 domains of murine IgG2a (GenBank accession number V00798). The PCR primer pairs 5'-AGGTSMARCTGCAGSAGTCW-3' (SEQ ID NO: 35), where S=C or G, M=A or C, R=A or G, W=A or T, and 5'-CTGAGCTCATTTACCCGGAGT CCGGGA GAAGCTCTT-3' (SEQ ID NO: 36) created flanking SalI and NotI sites at the 5' and 3' ends of the cassette, respectively. The murine IgG2a Fc domain cassette differs from the GenBank sequence at a single base (codon V369), creating a silent mutation. Hence, wild type Fc protein is expressed from this IgG2a Fc cassette.

The DNA fragment containing the VCAM-1 signal sequence fused to the huIFN-beta gene with the C-terminal enterokinase linker sequence, was excised from pCMG258 by a NotI to BamHI digestion and gel purified. The SalI site was present on the original pDSW247 plasmid, and is located immediately downstream and in frame with the IFN-beta gene coding sequence. The plasmid vector pDSW247 was prepared as a gel purified NotI+BamHI fragment (see Example 1). A 3-way ligation was performed, using the above mentioned fragments, to assemble the final expression vector encoding the IFN-beta-1a/IgG2a fusion. This expression plasmid was named pCMG261 and contains the VCAM-1 signal sequence in a fusion with the gene for mature human IFN-beta, enterokinase linker sequence and murine IgG2a Fc domain. The full DNA (SEQ ID NO:1) and protein sequence (SEQ ID NO:2) of the fusion protein are shown in FIG. 2.

EXAMPLE 3

Production of Interferon-beta-1a Fusion Protein in Mammalian Cells

The recombinant IFN-beta/Fc expression vector, pCMG261 was transiently tranfected into human EBNA 293 kidney cells to achieve expression of an IFN-beta-1a fusion protein of the invention. This recombinant expression plasmid is transfected by the lipofectamine protocol (catalogue #18324-020, Life Techonologies) in EBNA 283 human kidney cells according to the protocol of the manufacturer (Life Technologies, Gaithersburg, Md., Hawley-Nelson, P., Ciccarone, V., Gebeyehu, G. Jessee, J., Felgner, P. L. (1993) Focus 15.73) using 1–3 micrograms plasmid DNA for a 100 mm culture dish of EBNA 293 cells. On the the day following lipofectamine transfection of cells, the media is replaced with growth media (Dulbecco's modified Eagle's medium, 10% fetal bovine serum, 4 mM glutamine, 250 microgram Gentecin/ml (Life Technologies, Gaithersburg, Md.). The conditioned media is harvested 3–4 days later and the concentration of IFN-beta-1a-Fc was determined as described below.

Production of a IFN-beta/Fc fusion protein in other mammalian cell and prokaryotic cell expression systems could also be performed upon transfer of the protein coding region for the fusion protein into appropriate expression vectors for those systems. Alternative expression systems would include mammalian cell expression systems such as chinese hamster ovary (CHO) cells (Barsoum, J. (1995, Methods in Mol. Biol. 48, chapter 18, 225–237) and NS-0 murine cells (Rossman, C. et al. 1996, Protein Expression and Pur. 7, 335–342), and COS7 green monkey kidney cells (Ettinger, R. et. al. 1996, Proc. Natil. Acad. Sci. USA, 93:23, 13102–13107). Other eukaryotic expression systems that would be applicable would be the yeast *Pichia pastoris* (Eldin, P. E. et al. 1997, J. Immun. Methods, 201, 67–75) and *Saccharomyces cerevisiae* (Horwitz, A. H., 1988, Proc. Natil. Acad. Sci. USA, 85, 8678–8682).

Quantitation of the IFN-beta-1a-Fc protein expression levels in the culture supernatants from transfected EBNA 293 cells was performed by ELISA using a protein A purified IgG fraction of rabbit anti-IFN-beta-1a polyclonal antibodies (the antigen was purified IFN-beta-1a, Biogen, Inc.) to coat 96-well plates. The antibody detects IFN-beta-1a standards and culture supernatants in an interferon concentration range between 10 ng/mL and 0.3 ng/mL. Biotinylated rabbit polyclonal anti-IFN-beta-1a (same antibodies as above) and streptavidin-linked horseradish peroxidase were used to detect bound interferons. To confirm ELISA values, western blot analysis was performed in which reduced culture supernatants and IFN-beta-1a standards were run on 5–20% Tris-glycine gels (Novex, San Diego, Calif.), transferred to PVDF membrane (Amersham Life Science, Inc., Cleveland, Ohio) and detected with a different rabbit polyclonal serum (raised against IFN-beta-1a), followed by horseradish peroxidase linked-donkey anti-rabbit IgG (Jackson ImmunoResearch, West Grove, Pa.) antibodies.

EXAMPLE 4

Antiviral Activity of IFN-beta-1a/Murine IgG2a Fusion Protein

Human lung carcinoma cells (A549) were pretreated for 24 hours with IFN-beta-1a or IFN-beta-murine IgG2a (61, 41, 27, 18, 12, 8.2, 5.5, 3.7, 2.5, 1.6 pg/mL) prior to challenge with encephalomyocarditis virus (EMCV). Following a two-day incubation with the virus, viable cells were stained with a solution of XTT:PMS (2,3-bis(2-Methoxy-4-nitro-5-sulfophenyl)-2H-tetrazolium-5-carboxanilide inner salt:Phenazine methosulfate, at 333 μg/mL and 2 ng/mL, respectively, in phosphate buffered saline) and detected by spectroscopy at 450 nM. The assay was performed using triplicate data points for each IFN concentration.

Figure 8:
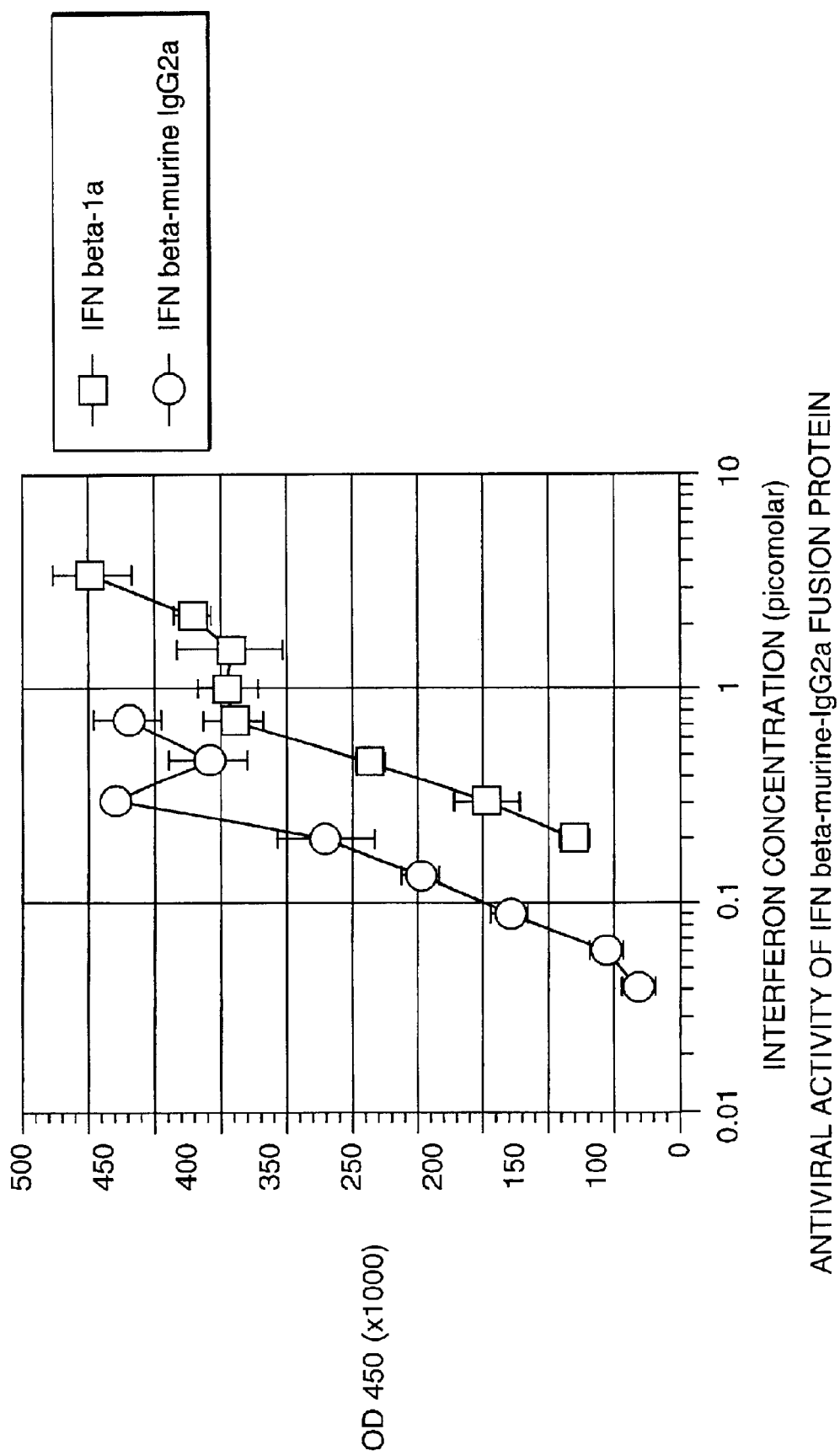

In FIG. 8 the standard deviations are shown as error bars. The 50% cytopathic effect for IFN-beta-1a was determined to be approximately 0.4 pM. The 50% cytopathic effect for IFN-beta-murine IgG2a was found to be 0.15 pM.

EXAMPLE 5

Construction and Production of a Human Interferon Beta-1a/Human IgG1 Fc Fusion Protein A. Construction of Human Interferon Beta-1a/Human IgG1 Fc Fusion Protein PCR technology was employed to create an expression plasmid encoding the human IFN beta DNA sequence fused to the Fc portion (hinge, CH2 and CH3 domains) of the human IgG1 heavy chain molecule.

EBNA construct: The plasmid vector pCH269 is a derivative of pCEP4 (Invitrogen, Carlsbad, Calif.) from which the EBNA-1 gene has been deleted. The plasmid was used for the construction of an expression vector useful for transient protein expression in EBNA 293 human kidney cells (Invitrogen, Carlsbad, Calif.; Shen E. S., et. al 1995, Gene 156, 235–239).

The fusion protein expression cassette was assembled from three DNA fragments: a Not I/Sal I fragment encoding the VCAM-1 signal sequence in frame and fused to the sequence encoding human IFN beta, a Sal I/Not I fragment encoding the hinge, CH2 and CH3 domains of human IgG1, and a Not I fragment of EBNA expression vector pCH269.

Two distinct Not I/Sal I fragments encoding the mature VCAM-1 signal sequence in frame and fused to the human IFN beta gene were made by PCR technology. The PCR template was plasmid pCMG258 (see Example 2 above) which encodes the mature VCAM-1 signal sequence in frame and fused to the human IFN beta gene, which itself is in frame and fused to the enterokinase linker sequence. Two sets of PCR primers were used. One set of primers (5'-AGCTTGCTAGCGGCCGCGGCCTCACTGGCTTCA-3' (SEQ ID NO: 37), and 5'-ATACGCGTCGACGTT TCGGAGGTAACATGTAAGTCTG-3': (SEQ ID NO: 38)) introduced an amino acid change from G to C at position 162. This fragment is called human IFN beta-C162.

The second primer set (5'-AGCTTGCTAGCGGCC GCGGCCTCACTGGCTTCA-3'(SEQ ID NO: 39), and 5'-TACACGTCGACGCTGCCACCACCGCCGTTTCGG AGGTAACATGTAAGTCTG-3': SEQ ID NO: 40)) also introduced the G162 to C162 amino acid substitution and changed the enterokinase linker sequence (DDDDK) to a GGGGS linker sequence in frame and fused 3' to the human IFN beta gene. This fragment is called human IFN beta-C162/G4S. Both sets of primers contain a 5' Not I site to enable ligation into pCH269, and a 3' Sal I cleavage site to enable ligation with the Sal I/Not I fragment of human IgG1.

The human IgG1 fragment which encodes the hinge, CH2 and CH3 domains of human IgG1 was prepared by restriction enzyme (Sal I/Not I) digestion of plasmid pEAG409, a derivative of plasmid SAB 144 (described in U.S. Pat. No. 5,547,853). The fragment was excised and gel purified. The EBNA expression vector plasmid pCH269 was digested with Not I and gel purified.

Two human IFN beta-human IgG1 Fc fusion constructs were generated by two three-way ligations. One construct, called ZL6206 contains the G4S linker; the other construct, called ZL5107, is a direct fusion. The full DNA and protein sequences of the open reading frames of the direct fusion (see FIG. 10) are shown in SEQ ID NO: 41 and SEQ ID NO: 42, respectively. The full DNA and protein sequences of the open reading frames of the linker fusion (see FIG. 11) are shown in SEQ ID NO: 43 and SEQ ID NO: 44, respectively.

CHO Construct:

A human IFN beta-human IgG1 Fc fusion CHO stable expression construct was made which was comprised of the human IFN beta directly linked to human IgG1 Fc. The human IFN beta-human IgG1 Fc fragment was cut from plasmid ZL5107 with Not I and gel purified; it was ligated into the Not I site of pEAG347 (an expression vector containing tandem SV40 early and Adenovirus major late promoters [derived from pAD2beta plasmid], a unique NotI cloning site, followed by SV40 late transcription termination and polyA signals [derived from pCMVbeta plasmid]. pEAG347 contains a pUC19-derived plasmid backbone and a pSV2dhfr-derived dhfr for MTX selection and amplification in transfected CHO cells.).

B. Production of Human Interferon-Beta-1a/Human IgG1 Fc Fusion Protein in Mammalian Cells Transient Transfection of Human IFN Beta Fusion Constructs into EBNA293 Cells:

The recombinant IFN-beta/human IgG1 Fc expression vectors described above were transiently transfected into human EBNA 293 kidney cells to achieve expression of an IFN-beta-1a fusion protein of the invention. These recombinant expression plasmids were transfected by the lipofectamine protocol (catalogue#18324–020, Life Technologies) in EBNA 293 human kidney cells according to the protocol described in Example 3 above.

Stable Transfection of Human IFN Beta-1a/Human IgG1 Fc Fusion Construct (No Linker) into dhfr-CHO Cells:

The recombinant IFN-beta/human IgG1 Fc (with no linker) dhfr containing expression vector described above was stably transfected into dhfr-CHO cells to achieve expression of an IFN-beta-1a fusion protein of the invention. This recombinant expression plasmid was transfected by electroporation and selection of positive clones was accomplished according the following protocol:

Plasmid DNA (20 mcg) digested with Bgl II was precipitated, resuspended in 800 mcl of HEPES buffer and added to $10 \times 10^7$ CHO cells/ml. Following electroporation, cells were cultured in DMEM complete media for 2 days. Cells were then split into 20–40 10 cm dishes with complete DMEM/dialyzed 10% FBS and cultured for 5 days before moving the cells into selection media with escalating (50–200 ng/ml) concentrations of MTX in DMEM for two weeks. At the end of two weeks, single colonies of cells were selected and expanded. Supernatants derived from 22 CHO clones were tested in antiviral assays.

Activity:

The anti-viral activity of the fusion proteins was determined in CPE assays as described in Example 4. Based on the 60 MU/mg specific activity of the interferon-beta-1a standard used in the assay, the activity of the transiently (EBNA) expressed human interferon-beta-1a/human IgG1 Fc fusion protein with the linker was 900 U/ml and the activity without a linker was 440 U/ml. The activity of CHO expressed human interferon-beta-1a/human IgG1 Fc fusion protein was 50 U/ml.

EXAMPLE 6

Measurement of Interferon-beta-1a Antiviral Activity in the Plasma of Mice Treated with Interferon-beta-1a and Interferon-beta-1a/Murine IgG2a Fusion Protein Mice (C57/B16) are injected i.v. through the tail vein with 50,000 Units of interferon-beta-1a (bulk) or 5,000 Units of interferon-beta-1a-murine IgG2a fusion protein. An equal volume of phosphate buffer is given as a control.

Blood is sampled through retro-orbital bleeds at different time points (immediately, 0.25, 1, 4, 24 and 48 hours) after interferon beta injection. There are at least 3 mice per time point. Whole blood is collected into tubes containing anticoagulant, cells are removed and the resulting plasma frozen until time of assay. The plasma samples are diluted 1:10 into serum free assay media and passed through a 0.2 um syringe filter.

The diluted samples are then titrated into designated wells of a 96 well tissue culture plate containing A549 cells. A standard Interferon-beta-1a (10, 6.7, 4.4, 2.9, 1.3, 0.9 and 0.6

Figure 9:
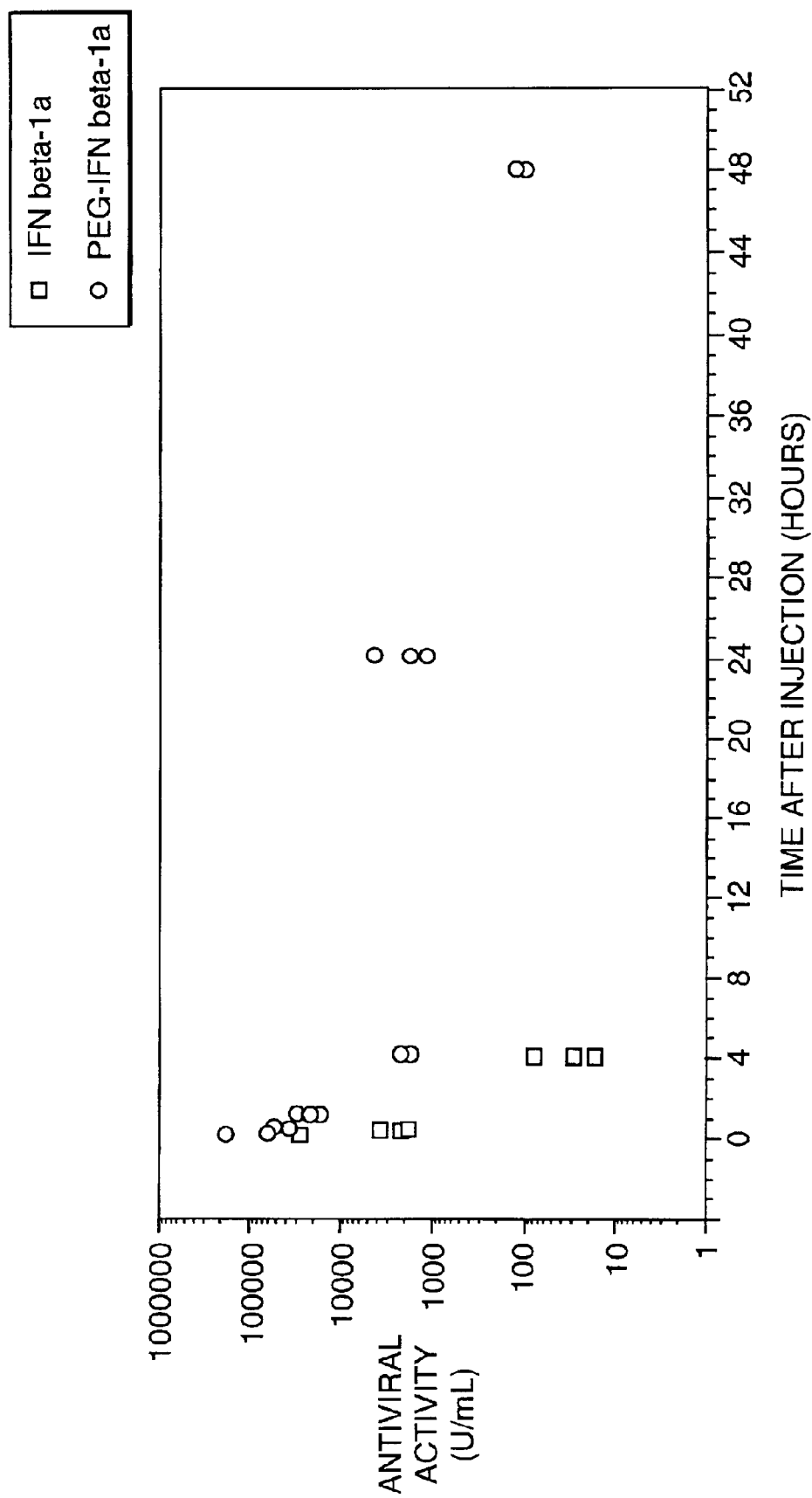

U/ml AVONEX) and 4 samples were run on every plate. The cells are pretreated with samples for 24 hours prior to challenge with EMC virus. Following a two-day incubation with virus, viable cells are stained with a solution of MTT (at 5 mg/ml in phosphate buffer) for 1 hour, washed with phosphate buffer, and solubilized with 1.2 N HCl in isopropanol. The wells were read at 450 nm. Standard curves are generated for each plate and used to determine the amount of interferon-beta-1a activity in each sample. The activity in the samples from the different mice are graphed against the time points in FIG. 9.

The slower loss of interferon-beta-1a fusion from circulation as a function of time indicates that the half life of the fusion protein sample is much longer than that of the unmodified interferon-beta-1a control. A second highly significant finding from the study was that very little of the fusion protein was lost during the distribution phase, as evidenced by the similar high levels of activity at the 15 and 60 minutes timepoints. The data indicate that, unlike the control interferon-beta-1a, the distribution of the interferon-beta-1a fusion protein is largely limited to the vasculature.

EXAMPLE 7

Comparative Pharmacokinetics and Pharmacodynamics in Primates

Comparative studies are conducted with interferon-beta 1a fusion and native interferon-beta 1a (as non formulated bulk intermediate AVONEX® interferon-beta-1a in 100 mM sodium phosphate, 200 mM NaCl, pH 7.2) to determine their relative stability and activity in primates. In these studies, the pharmacokinetics and pharmacodynamics of the interferon-beta-1a fusion in primates is compared to that of native interferon-beta 1a and reasonable inferences can be extended to humans.

Animals and Methods
Study Design

This is a parallel group, repeat dose study to evaluate the comparative pharmacokinetics and pharmacodynamics of interferon-beta-1a fusion protein and nonfusion interferon-beta-1a.

Healthy primates (preferably rhesus monkeys) are used for this study. Prior to dosing, all animals will be evaluated for signs of ill health by a Lab Animal Veterinary on two occasions within 14 days prior to test article administration; one evaluation must be within 24 hours prior to the first test article administration. Only healthy animals will receive the test article. Evaluations will include a general physical examination and pre-dose blood draws for baseline clinical pathology and baseline antibody level to interferon-beta-1a. All animals will be weighed and body temperatures will be recorded within 24 hours prior to test article administrations.

Twelve subjects are enrolled and assigned to groups of three to receive 1 MU/kg of interferon-beta-1a as either a fused or a non-fused, but otherwise identical interferon-beta-1a. Administration is by either the subcutaneous (SC) or intravenous (IV) routes. Six male animals will receive test article by the IV route (3/treatment) and another 6 male animals will receive test article by the SC route (3/treatment). All animals must be naive to interferon-beta treatment. Each animal will be dosed on two occasions; doses will be separated by four weeks. The dose volume will be 1.0 mL/kg.

Blood is drawn for pharmacokinetic testing at 0, 0.083, 0.25, 0.5, 1, 1.5, 2, 4, 6, 8, 12, 24, 48, 72, and 96 hours following each injection. Blood samples for measurements of the interferon induced biological response marker, serum neopterin, are drawn at 0, 24, 48, 72, 96, 168, 336, 504 hours following administration of study drug.

Evaluations during the study period include clinical observations performed 30 minutes and 1 hour post-dose for signs of toxicitiy. Daily cageside observations will be performed and general appearance, signs of toxicity, discomfort, and changes in behavior will be recorded. Body weights and body temperatures will be recorded at regular intervals through 21 days post-dose.

Assay Methods

Levels of interferon beta in serum are quantitated using a cytopathic effect (CPE) bioassay. The CPE assay measures levels of interferon-mediated antiviral activity. The level of antiviral activity in a sample reflects the number of molecules of active interferon contained in that sample at the time the blood is drawn. This approach has been the standard method to assess the pharmacokinetics of interferon beta. The CPE assay used in the current study detects the ability of interferon beta to protect human lung carcinoma cells (A549, #CCL-185, ATCC, Rockville, Md.) from cytotoxicity due to encephalomyocarditis (EMC) virus. The cells are preincubated for 15 to 20 hours with serum samples to allow the induction and synthesis of interferon inducible proteins that then mount an antiviral response. Afterwards EMC virus is added and incubated for a further 30 hours before assessment of cytotoxicity is made using a crystal violet stain. An internal interferon beta standard as well as an interferon-beta-Ig internal standard is tested concurrently with samples on each assay plate. This standard is calibrated against a natural human fibroblast interferon reference standard (WHO Second International Standard for Interferon, Human Fibroblast, Gb-23-902-53). Each assay plate also includes cell growth control wells containing neither interferon beta of any kind nor EMC, and virus control wells contain cells and EMC but no interferon beta. Control plates containing the standard and samples are also prepared to determine the effect, if any, of the samples on cell growth. These plates are stained without the addition of virus.

Samples and standards are tested in duplicate on each of two replicate assay plates, yielding four data points per sample. The geometric mean concentration of the four replicates is reported. The limit of detection in this assay is 10 units (U)/ml.

Serum concentrations of neopterin are determined at the clinical pharmacology unit using commercially available assays.

Pharmacokinetic and Statistical Methods

Rstrip™ software (MicroMath, Inc., Salt Lake City, Utah) is used to fit data to pharmacokinetic models. Geometric mean concentrations are plotted by time for each group. Since assay results are expressed in dilutions, geometric means are considered more appropriate than arithmetic means. Serum interferon levels are adjusted for baseline values and non-detectable serum concentrations are set to 5 U/ml, which represents one-half the lower limit of detection.

For IV infusion data, a two compartment IV infusion model is fit to the detectable serum concentrations for each subject, and the SC data are fit to a two compartment injection model.

The following pharmacokinetic parameters are calculated:
(i) observed peak concentration, $C_{max}$ (U/ml);
(ii) area under the curve from 0 to 48 hours, AUC using the trapezoidal rule;
(iii) elimination half-life;
and, from IV infusion data (if IV is employed):
(iv) distribution half-life (h);
(v) clearance (ml/h)
(vi) apparent volume of distribution, Vd (L).

WinNonlin (Version 1.0, Scientific Consulting Inc., Apex, N.C.) software is used to calculate the elimination half-lives after SC and IM injection.

For neopterin, arithmetic means by time are presented for each group. $E_{max}$, the maximum change from baseline, is calculated. $C_{max}$, AUC and $E_{max}$ are submitted to a one-way analysis of variance to compare dosing groups. $C_{max}$ and AUC are logarithmically transformed prior to analysis; geometric means are reported.

EXAMPLE 8

Anti-Angiogenic Effects of Interferon Beta-1a Fusion

Assessment of the Ability of an Interferon-beta-1a Fusion to Inhibit Endothelial Cell Proliferation in Vitro Human venous endothelial cells (Cell Systems, Cat. #2V0-P75) and human dermal microvascular endothelial cells (Cell Systems, Cat. #2M1-C25) are maintained in culture with CS-C Medium Kit (Cell Systems, Cat. #4Z0-500). Twenty-four hours prior to the experiment, cells are trypsinized, and resuspended in assay medium, 90% M199 and 10% fetal bovine serum (FBS), and are adjusted to desired cell density. Cells are then plated onto gelatin-coated 24 or 96 well plates, either at 12,500 cells/well or 2,000 cells/well, respectively.

After overnight incubation, the assay medium is replaced with fresh medium containing 20 ng/ml of human recombinant basic Fibroblast Growth Factor (Becton Dickinson, Cat. #40060) and various concentrations of fusion and non-fusion interferon-beta-1a proteins or positive control (endostatin can be used as a positive control, as could an antibody to bFGF). The final volume is adjusted to 0.5 ml in the 24 well plate or 0.2 ml in the 96 well plate.

After seventy-two hours, cells are trypsinized for Coulter counting, frozen for CyQuant fluorescense reading, or labeled with [3H] thymidine.

This in vitro assay tests the human interferon-beta molecules of the invention for effects on endothelial cell proliferation which may be indicative of anti-angiogenic effects in vivo. See O'Reilly, M. S., T. Boehm, Y. Shing, N. Fukal, G. Vasios, W. Lane, E. Flynn, J. Birkhead, B. Olsen, and J. Folkman. (1997). Endostatin: An Endogenous Inhibitor of Angiogensis and Tumor Growth. *Cell* 88, 277–285.

EXAMPLE 9

In Vivo Model to Test Anti-Angiogenic and Neovascularization Effects of Interferon-beta-1a/Ig Fusion A variety of models have been developed to test for the anti-angiogenic and anti-neovascularization effects of the molecules described herein. Some of these models have been described in U.S. Pat. No. 5,733,876 (Mar. 31, 1998: "Method of inhibiting angiogenesis) and U.S. Pat. No. 5,135,919 (Aug. 4, 1992:" Method and a pharmaceutical composition for the inhibition of angiogenesis "). Other assays include the shell-less chorioallantoic membrane (CAM) assay of S. Taylor and J. Folkman; Nature, 297, 307 (1982) and R. Crum. S. Szabo and J. Folkman; Science. 230. 1375 (1985); the mouse dorsal air sac method antigiogenesis model of Folkman, J. et al.; J. Exp. Med., 133, 275 (1971) and the rat corneal micropocket assay of Gimbrone, M. A. Jr. et al., J. Natl. Cancer Inst. 52, 413(1974) in which corneal vascularization is induced in adult male rats of the Sprague-Dawley strain (Charles River, Japan) by implanting 500 ng of basic FGF (bovine, R & D Systems, Inc.) impregnated in EVA (ethylene-vinyl acetate copolymer) pellets in each cornea.

Other methods for testing interferon-beta/Ig fusions for anti-angiogenic effects in an animal model include (but are not limited to) protocols for screening new potential anti-cancer agents as described in the original Cancer Chemotherapy Reports, Part 3, Vol. 3, No.2, September 1972 and the supplement In Vivo Cancer Models, 1976–1982, NIH Publication No. 84–2635, February 1984. Because of the species barriers of Type I interferons, to assess the anti-angiogenic activity of interferon-beta fusions in rodent models, rodent interferon-beta/:Ig fusion preparations are generated. Such screening methods are exemplified by a protocol to test for the anti-angiogenic effects of murine interferon-beta/Ig fusions on subcutaneously-implanted Lewis Lung Carcinoma.

Origin of Tumor Line:

Arose spontaneously in 1951 as a carcinoma of the lung in a C57BL/6 mouse. Summary of Test Procedures: A tumor fragment is implanted subcutaneously in the axillary region of a B6D2F1 mouse. The test agent (i.e, a fusion protein of the invention) is administered at various doses, subcutaneously (SC) or intraperitoneally (IP) on multiple days following tumor implantation. The parameter measured is median survival time. Results are expressed as a percentage of control survival time.

Animals:

Propagation: C57BL/6 mice.

Testing: B6D2F1 mice.

Weight: Mice should be within a 3 gm weight range with a minimum weight of 18 gm for males and 17 gm for females.

Sex: One sex is used for all test and control animals in one experiment.

Source: One source, if feasible, for all animals in one experiment.

Experiment Size:

Ten animals per test group.

Tumor Transfer:

Propagation:

Fragment: Prepare a 2–4 mm fragment of a s.c. donor tumor

Time: Day 13–15

Site: Implant the fragment s.c. in the axillary region with a puncture in the inguinal region.

Testing:

Fragment: Prepare a 2–4 mm fragment of s.c. donor tumor.

Time: Day 13–15.

Site: Implant the fragment s.c. in the axillary region with a puncture in the inguinal region.

Testing Schedule:

Day 0: Implant tumor. Run bacterial cultures. Test positive control compound in every odd-numbered experiment. Prepare materials. Record deaths daily.

Day 1: Check cultures. Discard experiment if contaminated. Randomize animals. Treat as instructed (on day 1 and on following days).

Day 2: Recheck cultures. Discard experiment if contaminated.

Day 5: Weigh Day 2 and day of initial test agent toxicity evaluation.

Day 14: Control early-death day.

Day 48: Control no-take day.

Day 60: End and evaluate experiment. Examine lungs grossly for tumor.

Quality Control:

Schedule the positive control compound (NSC 26271 (Cytoxan at a dose of 100 mg/kg/injection)) in every odd-numbered experiment, the regimen for which is intraperitoneal on Day 1 only. The lower Test/Control limit for the positive control is 140%. The acceptable untreated control median survival time is 19–35.6 days.

Evaluation:

The parameter measured is median survival time Compute mean animal body weights for Day 1 and Day 5, compute Test/Control ratio for all test groups with. The mean animal body weights for staging day and final evaluation day are computed. The Test/Control ratio is computed for all test groups with >65% survivors on Day 5. A Test/Control ratio value <86% indicates toxicity. An excessive body weight change difference (test minus control) may also be used in evaluating toxicity.

Criteria for Activity:

An initial Test/Control ratio greater than or equal to 140% is considered necessary to demonstrate moderate activity. A reproducible Test/Control ratio value of greater than or equal to 150% is considered significant activity.

SEQUENCE LISTING

<160> NUMBER OF SEQ ID NOS: 61

<210> SEQ ID NO 1
<211> LENGTH: 1197
<212> TYPE: DNA
<213> ORGANISM: Mus sp.

<400> SEQUENCE: 1

```
atgagctaca acttgcttgg attcctacaa agaagcagca attttcagtg tcagaagctc      60
ctgtggcaat tgaatgggag gcttgaatac tgcctcaagg acaggatgaa ctttgacatc     120
cctgaggaga ttaagcagct gcagcagttc cagaaggagg acgccgcatt gaccatctat     180
gagatgctcc agaacatctt tgctattttc agacaagatt catctagcac tggctggaat     240
gagactattg ttgagaacct cctggctaat gtctatcatc agataaacca tctgaagaca     300
gtcctggaag aaaaactgga gaagaagat ttcaccaggg gaaaactcat gagcagtctg     360
cacctgaaaa gatattatgg gaggattctg cattacctga aggccaagga gtacagtcac     420
tgtgcctgga ccatagtcag agtggaaatc ctaaggaact tttacttcat taacagactt     480
acaggttacc tccgaaacga cgatgatgac aaggtcgaca aaactcacac atgcccaccg     540
tgcccagcac ctgaactcct gggggaccg tcagtcttcc tcttcccccc aaaacccaag     600
gacaccctca tgatctcccg gacccctgag gtcacatgcg tggtggtgga cgtgagccac     660
gaagaccctg aggtcaagtt caactggtac gtggacggcg tggaggtgca taatgccaag     720
acaaagccgc gggaggagca gtacaacagc acgtaccgtg tggtcagcgt cctcaccgtc     780
ctgcaccagg actggctgaa tggcaaggag tacaagtgca aggtctccaa caaagccctc     840
ccagccccca tcgagaaaac catctccaaa gccaagggc agccccgaga accacaggtg     900
tacaccctgc ccccatcccg ggatgagctg accaagaacc aggtcagcct gacctgcctg     960
gtcaaaggct tctatcccag cgacatcgcc gtggagtggg agagcaatgg gcagccggag    1020
aacaactaca agaccacgcc tcccgtgttg gactccgacg gctccttctt cctctacagc    1080
aagctcaccg tggacaagag caggtggcag caggggaacg tcttctcatg ctccgtgatg    1140
catgaggctc tgcacaacca ctacacgcag aagagcctct ccctgtctcc gggaaa        1197
```

<210> SEQ ID NO 2
<211> LENGTH: 399
<212> TYPE: PRT
<213> ORGANISM: Mus sp.

<400> SEQUENCE: 2

```
Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30
```

```
Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn Asp Asp Asp Lys Val Asp Lys Thr His
                165                 170                 175

Thr Cys Pro Pro Cys Pro Ala Pro Glu Leu Leu Gly Gly Pro Ser Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser His Glu Asp Pro Glu
    210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Ala Leu Pro Ala Pro Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Arg Asp Glu Leu Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
        355                 360                 365

Trp Gln Gln Gly Asn Val Phe Ser Cys Ser Val Met His Glu Ala Leu
    370                 375                 380

His Asn His Tyr Thr Gln Lys Ser Leu Ser Leu Ser Pro Gly Lys
385                 390                 395

<210> SEQ ID NO 3
<211> LENGTH: 549
<212> TYPE: DNA
<213> ORGANISM: Mus sp.

<400> SEQUENCE: 3
tccgggggcc atcatcatca tcatcatagc tccggagacg atgatgacaa gatgagctac    60
```

```
aacttgcttg gattcctaca agaagcagc aattttcagt gtcagaagct cctgtggcaa      120
ttgaatggga ggcttgaata ctgcctcaag acaggatga actttgacat ccctgaggag      180
attaagcagc tgcagcagtt ccagaaggag gacgccgcat tgaccatcta tgagatgctc      240
cagaacatct ttgctatttt cagacaagat tcatctagca ctggctggaa tgagactatt      300
gttgagaacc tcctggctaa tgtctatcat cagataaacc atctgaagac agtcctggaa      360
gaaaaactgg agaagaaga tttcaccagg ggaaaactca tgagcagtct gcacctgaaa      420
agatattatg ggaggattct gcattacctg aaggccaagg agtacagtca ctgtgcctgg      480
accatagtca gagtggaaat cctaaggaac ttttacttca ttaacagact tacaggttac      540
ctccgaaac                                                              549
```

`<210>` SEQ ID NO 4
`<211>` LENGTH: 183
`<212>` TYPE: PRT
`<213>` ORGANISM: Mus sp.

`<400>` SEQUENCE: 4

```
Ser Gly Gly His His His His His His Ser Gly Asp Asp Asp
  1               5                  10                  15

Lys Met Ser Tyr Asn Leu Leu Gly Phe Leu Gln Arg Ser Ser Asn Phe
                 20                  25                  30

Gln Cys Gln Lys Leu Leu Trp Gln Leu Asn Gly Arg Leu Glu Tyr Cys
             35                  40                  45

Leu Lys Asp Arg Met Asn Phe Asp Ile Pro Glu Glu Ile Lys Gln Leu
         50                  55                  60

Gln Gln Phe Gln Lys Glu Asp Ala Ala Leu Thr Ile Tyr Glu Met Leu
 65                  70                  75                  80

Gln Asn Ile Phe Ala Ile Phe Arg Gln Asp Ser Ser Ser Thr Gly Trp
                 85                  90                  95

Asn Glu Thr Ile Val Glu Asn Leu Leu Ala Asn Val Tyr His Gln Ile
            100                 105                 110

Asn His Leu Lys Thr Val Leu Glu Glu Lys Leu Glu Lys Glu Asp Phe
        115                 120                 125

Thr Arg Gly Lys Leu Met Ser Ser Leu His Leu Lys Arg Tyr Tyr Gly
    130                 135                 140

Arg Ile Leu His Tyr Leu Lys Ala Lys Glu Tyr Ser His Cys Ala Trp
145                 150                 155                 160

Thr Ile Val Arg Val Glu Ile Leu Arg Asn Phe Tyr Phe Ile Asn Arg
                165                 170                 175

Leu Thr Gly Tyr Leu Arg Asn
            180
```

`<210>` SEQ ID NO 5
`<211>` LENGTH: 60
`<212>` TYPE: DNA
`<213>` ORGANISM: Homo sapiens

`<400>` SEQUENCE: 5

```
gatctagcaa tgctgcctgt gctgccctcc tggctgcctt gaatgggagg cttgaatact      60
```

`<210>` SEQ ID NO 6
`<211>` LENGTH: 51
`<212>` TYPE: DNA
`<213>` ORGANISM: Homo sapiens -continued

```
<400> SEQUENCE: 6
tattatggga ggattctgca ttacctgaag gccaaggagt actcacactg t            51

<210> SEQ ID NO 7
<211> LENGTH: 76
<212> TYPE: DNA
<213> ORGANISM: Homo sapiens

<400> SEQUENCE: 7
aattgaatgg gagggctgca gcttgcgctg cagacaggat gaactttgac atccctgagg   60
agattaagca gctgca                                                   76

<210> SEQ ID NO 8
<211> LENGTH: 51
<212> TYPE: PRT
<213> ORGANISM: Homo sapiens

<400> SEQUENCE: 8

Ala Ala Thr Thr Gly Ala Ala Thr Gly Gly Ala Gly Gly Cys Thr
 1               5                  10                  15

Thr Gly Ala Ala Thr Ala Cys Thr Gly Cys Cys Thr Cys Ala Ala Gly
             20                  25                  30

Gly Ala Cys Ala Gly Gly Ala Thr Gly Ala Ala Cys Thr Thr Thr Gly
         35                  40                  45

Ala Cys Ala
     50

<210> SEQ ID NO 9
<211> LENGTH: 60
<212> TYPE: DNA
<213> ORGANISM: Homo sapiens

<400> SEQUENCE: 9
ttctccggag acgatgatga caagatgagc tacaacttgc ttggattcct acaaagaagc   60

<210> SEQ ID NO 10
<211> LENGTH: 50
<212> TYPE: DNA
<213> ORGANISM: Homo sapiens

<400> SEQUENCE: 10
cgtcagagct gaaatcctag caaactttgc attcattgca agacttacag              50

<210> SEQ ID NO 11
<211> LENGTH: 47
<212> TYPE: DNA
<213> ORGANISM: Homo sapiens

<400> SEQUENCE: 11
ggtggtctca catgagctac aacttgcttg gattcctaca agaagc                  47

<210> SEQ ID NO 12
<211> LENGTH: 50
<212> TYPE: DNA
<213> ORGANISM: Homo sapiens

<400> SEQUENCE: 12
gccctcgagt cgaccttgtc atcatcgtcg tttcggaggt aacctgtaag              50

<210> SEQ ID NO 13
<211> LENGTH: 21
```

```
<212> TYPE: DNA
<213> ORGANISM: Homo sapiens

<400> SEQUENCE: 13
caagcttgct agcggccgcg g                                              21

<210> SEQ ID NO 14
<211> LENGTH: 28
<212> TYPE: DNA
<213> ORGANISM: Homo sapiens

<400> SEQUENCE: 14
ggtggtctca catggcttga gaagctgc                                       28

<210> SEQ ID NO 15
<211> LENGTH: 20
<212> TYPE: DNA
<213> ORGANISM: Homo sapiens

<400> SEQUENCE: 15
aggtsmarct gcagsagtcw                                                20

<210> SEQ ID NO 16
<211> LENGTH: 36
<212> TYPE: DNA
<213> ORGANISM: Homo sapiens

<400> SEQUENCE: 16
ctgagctcat ttacccggag tccgggagaa gctctt                              36

<210> SEQ ID NO 17
<211> LENGTH: 33
<212> TYPE: DNA
<213> ORGANISM: Homo sapiens

<400> SEQUENCE: 17
agcttgctag cggccgcggc ctcactggct tca                                 33

<210> SEQ ID NO 18
<211> LENGTH: 37
<212> TYPE: DNA
<213> ORGANISM: Homo sapiens

<400> SEQUENCE: 18
atacgcgtcg acgtttcgga ggtaacatgt aagtctg                             37

<210> SEQ ID NO 19
<211> LENGTH: 33
<212> TYPE: DNA
<213> ORGANISM: Homo sapiens

<400> SEQUENCE: 19
agcttgctag cggccgcggc ctcactggct tca                                 33

<210> SEQ ID NO 20
<211> LENGTH: 51
<212> TYPE: DNA
<213> ORGANISM: Homo sapiens

<400> SEQUENCE: 20
tacacgtcga cgctgccacc accgccgttt cggaggtaac atgtaagtct g             51

<210> SEQ ID NO 21
```

```
<211> LENGTH: 39
<212> TYPE: DNA
<213> ORGANISM: Homo sapiens

<400> SEQUENCE: 21
gccgctcgag ttatcagttt cggaggtaac ctgtaagtc                              39

<210> SEQ ID NO 22
<211> LENGTH: 72
<212> TYPE: DNA
<213> ORGANISM: Homo sapiens

<400> SEQUENCE: 22
ggaatgcttc aattgttgct gcactcctga gcaatgtcta tcatcagata aaccatctga      60
agacagttct ag                                                          72

<210> SEQ ID NO 23
<211> LENGTH: 72
<212> TYPE: DNA
<213> ORGANISM: Homo sapiens

<400> SEQUENCE: 23
ggaatgagac cattgttgag aacctcctgg ctaatgtcgc tcatcagata gcacatctgg      60
ctgcagttct ag                                                          72

<210> SEQ ID NO 24
<211> LENGTH: 44
<212> TYPE: DNA
<213> ORGANISM: Homo sapiens

<400> SEQUENCE: 24
ctagctgcaa aactggctgc agctgatttc accaggggaa aact                       44

<210> SEQ ID NO 25
<211> LENGTH: 69
<212> TYPE: DNA
<213> ORGANISM: Homo sapiens

<400> SEQUENCE: 25
ctagaagaaa aactggagaa agaagcagct accgctggaa aagcaatgag cgcgctgcac      60
ctgaaaaga                                                              69

<210> SEQ ID NO 26
<211> LENGTH: 51
<212> TYPE: DNA
<213> ORGANISM: Homo sapiens

<400> SEQUENCE: 26
tattatggga ggattctgca ttacctgaag gccaaggagt actcacactg t               51

<210> SEQ ID NO 27
<211> LENGTH: 76
<212> TYPE: DNA
<213> ORGANISM: Homo sapiens

<400> SEQUENCE: 27
catgagcagt ctgcacctga aaagatatta tgggcaatt gctgcatacc tggcagccaa       60
ggagtactca cactgt                                                      76

<210> SEQ ID NO 28
<211> LENGTH: 87
```

```
<212> TYPE: DNA
<213> ORGANISM: Homo sapiens

<400> SEQUENCE: 28
catgagcagt ctgcacctga aaagatatta tgggaggatt ctgcattacc tgaaggccgc      60
tgcatactca cactgtgcct ggacgat                                          87

<210> SEQ ID NO 29
<211> LENGTH: 87
<212> TYPE: DNA
<213> ORGANISM: Homo sapiens

<400> SEQUENCE: 29
catgagcagt ctgcacctga aaagatatta tgggaggatt ctgcattacc tgaaggcaaa      60
ggagtacgct gcatgtgcct ggacgat                                          87

<210> SEQ ID NO 30
<211> LENGTH: 50
<212> TYPE: DNA
<213> ORGANISM: Homo sapiens

<400> SEQUENCE: 30
cgtcagagct gaaatcctag caaactttgc attcattgca agacttacag                 50

<210> SEQ ID NO 31
<211> LENGTH: 47
<212> TYPE: DNA
<213> ORGANISM: Homo sapiens

<400> SEQUENCE: 31
ggtggtctca catgagctac aacttgcttg gattcctaca agaagc                     47

<210> SEQ ID NO 32
<211> LENGTH: 50
<212> TYPE: DNA
<213> ORGANISM: Homo sapiens

<400> SEQUENCE: 32
gccctcgagt cgaccttgtc atcatcgtcg tttcggaggt aacctgtaag                 50

<210> SEQ ID NO 33
<211> LENGTH: 21
<212> TYPE: DNA
<213> ORGANISM: Homo sapiens

<400> SEQUENCE: 33
caagcttgct agcggccgcg g                                                21

<210> SEQ ID NO 34
<211> LENGTH: 28
<212> TYPE: DNA
<213> ORGANISM: Homo sapiens

<400> SEQUENCE: 34
ggtggtctca catggcttga gaagctgc                                         28

<210> SEQ ID NO 35
<211> LENGTH: 20
<212> TYPE: DNA
<213> ORGANISM: Mus sp.

<400> SEQUENCE: 35
```

-continued aggtsmarct gcagsagtcw                                          20

<210> SEQ ID NO 36
<211> LENGTH: 36
<212> TYPE: DNA
<213> ORGANISM: Mus sp.

<400> SEQUENCE: 36
ctgagctcat tacccggag tccgggagaa gctctt                         36

<210> SEQ ID NO 37
<211> LENGTH: 33
<212> TYPE: DNA
<213> ORGANISM: Homo sapiens

<400> SEQUENCE: 37
agcttgctag cggccgcggc ctcactggct tca                           33

<210> SEQ ID NO 38
<211> LENGTH: 37
<212> TYPE: DNA
<213> ORGANISM: Homo sapiens

<400> SEQUENCE: 38
atacgcgtcg acgtttcgga ggtaacatgt aagtctg                       37

<210> SEQ ID NO 39
<211> LENGTH: 33
<212> TYPE: DNA
<213> ORGANISM: Homo sapiens

<400> SEQUENCE: 39
agcttgctag cggccgcggc ctcactggct tca                           33

<210> SEQ ID NO 40
<211> LENGTH: 51
<212> TYPE: DNA
<213> ORGANISM: Homo sapiens

<400> SEQUENCE: 40
tacacgtcga cgctgccacc accgccgttt cggaggtaac atgtaagtct g       51

<210> SEQ ID NO 41
<211> LENGTH: 1257
<212> TYPE: DNA
<213> ORGANISM: Homo sapiens

<400> SEQUENCE: 41
atgcctggga agatggtcgt gatccttgga gcctcaaata tactttggat aatgtttgca    60
gcttctcaag ccatgagcta caacttgctt ggattcctac aaagaagcag caattttcag   120
tgtcagaagc tcctgtggca attgaatggg aggcttgaat actgcctcaa ggacaggatg   180
aactttgaca tccctgagga gattaagcag ctgcagcagt tccagaagga ggacgccgca   240
ttgaccatct atgagatgct ccagaacatc tttgctattt tcagacaaga ttcatctagc   300
actggctgga atgagactat tgttgagaac ctcctggcta atgtctatca tcagataaac   360
catctgaaga cagtcctgga agaaaaactg gagaaagaag atttcaccag ggaaaactc   420 atgagcagtc tgcacctgaa aagatattat gggaggattc tgcattacct gaaggccaag   480
gagtacagtc actgtgcctg gaccatagtc agagtgaaa tcctaaggaa cttttactc   540 attaacagac ttacatgtta cctccgaaac gtcgacaaaa ctcacacatg cccaccgtgc   600

```
ccagcacctg aactcctggg ggaccgtcag tcttcctct tcccccccaaa acccaaggac    660 acctcatga tctcccggac ccctgaggtc acatgcgtgg tggtggacgt gagccacgaa    720
gaccctgagg tcaagttcaa ctggtacgtg gacggcgtgg aggtgcataa tgccaagaca    780
aagccgcggg aggagcagta caacagcacg taccgtgtgg tcagcgtcct caccgtcctg    840
caccaggact ggctgaatgg caaggagtac aagtgcaagg tctccaacaa agccctccca    900
gcccccatcg agaaaaccat ctccaaagcc aagggcagc cccgagaacc acaggtgtac    960
accctgcccc catcccggga tgagctgacc aagaaccagg tcagcctgac ctgcctggtc   1020
aaaggcttct atcccagcga catcgccgtg gagtgggaga gcaatgggca gccggagaac   1080
aactacaaga ccacgcctcc cgtgttggac tccgacggct ccttcttcct ctacagcaag   1140
ctcaccgtgg acaagagcag gtggcagcag gggaacgtct tctcatgctc cgtgatgcat   1200
gaggctctgc acaaccacta cacgcagaag agcctctccc tgtctccggg gaaatga     1257
```

<210> SEQ ID NO 42
<211> LENGTH: 418
<212> TYPE: PRT
<213> ORGANISM: Homo sapiens

<400> SEQUENCE: 42

```
Met Pro Gly Lys Met Val Val Ile Leu Gly Ala Ser Asn Ile Leu Trp
  1               5                  10                  15

Ile Met Phe Ala Ala Ser Gln Ala Met Ser Tyr Asn Leu Leu Gly Phe
                 20                  25                  30

Leu Gln Arg Ser Ser Asn Phe Gln Cys Gln Lys Leu Leu Trp Gln Leu
             35                  40                  45

Asn Gly Arg Leu Glu Tyr Cys Leu Lys Asp Arg Met Asn Phe Asp Ile
         50                  55                  60

Pro Glu Glu Ile Lys Gln Leu Gln Gln Phe Gln Lys Glu Asp Ala Ala
 65                  70                  75                  80

Leu Thr Ile Tyr Glu Met Leu Gln Asn Ile Phe Ala Ile Phe Arg Gln
                 85                  90                  95

Asp Ser Ser Ser Thr Gly Trp Asn Glu Thr Ile Val Glu Asn Leu Leu
            100                 105                 110

Ala Asn Val Tyr His Gln Ile Asn His Leu Lys Thr Val Leu Glu Glu
        115                 120                 125

Lys Leu Glu Lys Glu Asp Phe Thr Arg Gly Lys Leu Met Ser Ser Leu
    130                 135                 140

His Leu Lys Arg Tyr Tyr Gly Arg Ile Leu His Tyr Leu Lys Ala Lys
145                 150                 155                 160

Glu Tyr Ser His Cys Ala Trp Thr Ile Val Arg Val Glu Ile Leu Arg
                165                 170                 175

Asn Phe Tyr Phe Ile Asn Arg Leu Thr Cys Tyr Leu Arg Asn Val Asp
            180                 185                 190

Lys Thr His Thr Cys Pro Pro Cys Pro Ala Pro Glu Leu Leu Gly Gly
        195                 200                 205

Pro Ser Val Phe Leu Phe Pro Pro Lys Pro Lys Asp Thr Leu Met Ile
    210                 215                 220

Ser Arg Thr Pro Glu Val Thr Cys Val Val Val Asp Val Ser His Glu
225                 230                 235                 240

Asp Pro Glu Val Lys Phe Asn Trp Tyr Val Asp Gly Val Glu Val His
                245                 250                 255
```

```
Asn Ala Lys Thr Lys Pro Arg Glu Glu Gln Tyr Asn Ser Thr Tyr Arg
            260                 265                 270
Val Val Ser Val Leu Thr Val Leu His Gln Asp Trp Leu Asn Gly Lys
        275                 280                 285
Glu Tyr Lys Cys Lys Val Ser Asn Lys Ala Leu Pro Ala Pro Ile Glu
    290                 295                 300
Lys Thr Ile Ser Lys Ala Lys Gly Gln Pro Arg Glu Pro Gln Val Tyr
305                 310                 315                 320
Thr Leu Pro Pro Ser Arg Asp Glu Leu Thr Lys Asn Gln Val Ser Leu
                325                 330                 335
Thr Cys Leu Val Lys Gly Phe Tyr Pro Ser Asp Ile Ala Val Glu Trp
            340                 345                 350
Glu Ser Asn Gly Gln Pro Glu Asn Asn Tyr Lys Thr Thr Pro Pro Val
        355                 360                 365
Leu Asp Ser Asp Gly Ser Phe Phe Leu Tyr Ser Lys Leu Thr Val Asp
    370                 375                 380
Lys Ser Arg Trp Gln Gln Gly Asn Val Phe Ser Cys Ser Val Met His
385                 390                 395                 400
Glu Ala Leu His Asn His Tyr Thr Gln Lys Ser Leu Ser Leu Ser Pro
                405                 410                 415

Gly Lys

<210> SEQ ID NO 43
<211> LENGTH: 1272
<212> TYPE: DNA
<213> ORGANISM: Homo sapiens

<400> SEQUENCE: 43
atgcctggga agatggtcgt gatccttgga gcctcaaata tactttggat aatgtttgca      60
gcttctcaag ccatgagcta caacttgctt ggattcctac aaagaagcag caattttcag     120
tgtcagaagc tcctgtggca attgaatggg aggcttgaat actgcctcaa ggacaggatg     180
aactttgaca tccctgagga gattaagcag ctgcagcagt tccagaagga ggacgccgca     240
ttgaccatct atgagatgct ccagaacatc tttgctattt tcagacaaga ttcatctagc     300
actggctgga tgagactat tgttgagaac ctcctggcta atgtctatca tcagataaac     360
catctgaaga cagtcctgga agaaaaactg gagaagaag atttcaccag gggaaaactc     420
atgagcagtc tgcacctgaa agatattat ggaggattc tgcattacct gaaggccaag     480
gagtacagtc actgtgcctg gaccatagtc agagtggaaa tcctaaggaa cttttacttc     540
attaacagac ttcatgttta cctccgaaac ggcggtggtg gcagcgtcga caaaactcac     600
acatgcccac cgtgcccagc acctgaactc ctggggggac cgtcagtctt cctcttcccc     660
ccaaaaccca aggacaccct catgatctcc cggacccctg aggtcacatg cgtggtggtg     720
gacgtgagcc acgaagaccc tgaggtcaag ttcaactggt acgtggacgg cgtggaggtg     780
cataatgcca agacaaagcc gcgggaggag cagtacaaca gcacgtaccg tgtggtcagc     840
gtcctcaccg tcctgcacca ggactggctg aatggcaagg agtacaagtg caaggtctcc     900
aacaaagccc tcccagcccc catcgagaaa accatctcca agccaaaggg cagccccga     960
gaaccacagg tgtacaccct gcccccatcc cgggatgagc tgaccaagaa ccaggtcagc    1020
ctgacctgcc tggtcaaagg cttctatccc agcgacatcg ccgtggagtg ggagagcaat    1080
gggcagccgg agaacaacta caagaccacg cctcccgtgt ggactccga cggctccttc    1140
ttcctctaca gcaagctcac cgtggacaag agcaggtggc agcaggggaa cgtcttctca    1200
```

-continued

```
tgctccgtga tgcatgaggc tctgcacaac cactacacgc agaagagcct ctccctgtct   1260
cccgggaaat ga                                                        1272
```

<210> SEQ ID NO 44
<211> LENGTH: 423
<212> TYPE: PRT
<213> ORGANISM: Homo sapiens

<400> SEQUENCE: 44

```
Met Pro Gly Lys Met Val Val Ile Leu Gly Ala Ser Asn Ile Leu Trp
 1               5                  10                  15

Ile Met Phe Ala Ala Ser Gln Ala Met Ser Tyr Asn Leu Leu Gly Phe
            20                  25                  30

Leu Gln Arg Ser Ser Asn Phe Gln Cys Gln Lys Leu Leu Trp Gln Leu
        35                  40                  45

Asn Gly Arg Leu Glu Tyr Cys Leu Lys Asp Arg Met Asn Phe Asp Ile
    50                  55                  60

Pro Glu Glu Ile Lys Gln Leu Gln Gln Phe Gln Lys Glu Asp Ala Ala
65                  70                  75                  80

Leu Thr Ile Tyr Glu Met Leu Gln Asn Ile Phe Ala Ile Phe Arg Gln
                85                  90                  95

Asp Ser Ser Thr Gly Trp Asn Glu Thr Ile Val Glu Asn Leu Leu
            100                 105                 110

Ala Asn Val Tyr His Gln Ile Asn His Leu Lys Thr Val Leu Glu Glu
        115                 120                 125

Lys Leu Glu Lys Glu Asp Phe Thr Arg Gly Lys Leu Met Ser Ser Leu
    130                 135                 140

His Leu Lys Arg Tyr Tyr Gly Arg Ile Leu His Tyr Leu Lys Ala Lys
145                 150                 155                 160

Glu Tyr Ser His Cys Ala Trp Thr Ile Val Arg Val Glu Ile Leu Arg
                165                 170                 175

Asn Phe Tyr Phe Ile Asn Arg Leu Thr Cys Tyr Leu Arg Asn Gly Gly
            180                 185                 190

Gly Gly Ser Val Asp Lys Thr His Thr Cys Pro Pro Cys Pro Ala Pro
        195                 200                 205

Glu Leu Leu Gly Gly Pro Ser Val Phe Leu Phe Pro Pro Lys Pro Lys
    210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                245                 250                 255

Gly Val Glu Val His Asn Ala Lys Thr Lys Pro Arg Glu Glu Gln Tyr
            260                 265                 270

Asn Ser Thr Tyr Arg Val Val Ser Val Leu Thr Val Leu His Gln Asp
        275                 280                 285

Trp Leu Asn Gly Lys Glu Tyr Lys Cys Lys Val Ser Asn Lys Ala Leu
    290                 295                 300

Pro Ala Pro Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
            340                 345                 350
```

```
Ile Ala Val Glu Trp Glu Ser Asn Gly Gln Pro Glu Asn Asn Tyr Lys
        355                 360                 365

Thr Thr Pro Pro Val Leu Asp Ser Asp Gly Ser Phe Phe Leu Tyr Ser
        370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Pro Gly Lys
                420

<210> SEQ ID NO 45
<211> LENGTH: 166
<212> TYPE: PRT
<213> ORGANISM: Homo sapiens

<400> SEQUENCE: 45

Met Ala Tyr Ala Ala Leu Gly Ala Leu Gln Ala Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 46
<211> LENGTH: 166
<212> TYPE: PRT
<213> ORGANISM: Homo sapiens

<400> SEQUENCE: 46

Met Ser Tyr Asn Leu Leu Gly Phe Leu Gln Arg Ser Ser Asn Ala Ala
1               5                   10                  15

Cys Ala Ala Leu Leu Ala Ala Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80
```

```
Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 47
<211> LENGTH: 166
<212> TYPE: PRT
<213> ORGANISM: Homo sapiens

<400> SEQUENCE: 47

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Ala Ala Ala Cys Ala
            20                  25                  30

Ala Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 48
<211> LENGTH: 166
<212> TYPE: PRT
<213> ORGANISM: Homo sapiens

<400> SEQUENCE: 48

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Ala Ala Phe Ala Ile Pro Ala Glu Ile Lys Gln Leu Gln
        35                  40                  45

Gln Phe Gln Lys Glu Asp Ala Ala Leu Thr Ile Tyr Glu Met Leu Gln
    50                  55                  60
```

```
Asn Ile Phe Ala Ile Phe Arg Gln Asp Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 49
<211> LENGTH: 166
<212> TYPE: PRT
<213> ORGANISM: Homo sapiens

<400> SEQUENCE: 49

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
                 20                  25                  30

Lys Asp Arg Met Asn Phe Asp Ile Pro Glu Glu Ile Ala Ala Ala Ala
             35                  40                  45

Ala Phe Ala Ala Ala Asp Ala Ala Leu Thr Ile Tyr Glu Met Leu Gln
 50                  55                  60

Asn Ile Phe Ala Ile Phe Arg Gln Asp Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 50
<211> LENGTH: 166
<212> TYPE: PRT
<213> ORGANISM: Homo sapiens

<400> SEQUENCE: 50

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
                 20                  25                  30

Lys Asp Arg Met Asn Phe Asp Ile Pro Glu Glu Ile Lys Gln Leu Gln
             35                  40                  45
```

```
Gln Phe Gln Lys Glu Asp Ala Ala Leu Thr Ile Tyr Glu Met Leu Ala
    50                  55                  60

Asn Ile Ala Ser Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Ala Leu Met Ser Ser Leu His Leu Lys Arg Tyr Tyr Gly Arg
                115                 120                 125

Ile Leu His Tyr Leu Lys Ala Lys Glu Tyr Ser His Cys Ala Trp Thr
                130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 51
<211> LENGTH: 166
<212> TYPE: PRT
<213> ORGANISM: Homo sapiens

<400> SEQUENCE: 51

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
                35                  40                  45

Gln Phe Gln Lys Glu Asp Ala Ala Leu Thr Ile Tyr Glu Met Leu Gln
    50                  55                  60

Asn Ile Phe Ala Ile Phe Ala Ala Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Ala Leu Met Ser Ser Leu His Leu Lys Arg Tyr Tyr Gly Arg
                115                 120                 125

Ile Leu His Tyr Leu Lys Ala Lys Glu Tyr Ser His Cys Ala Trp Thr
                130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 52
<211> LENGTH: 166
<212> TYPE: PRT
<213> ORGANISM: Homo sapiens

<400> SEQUENCE: 52

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30
```

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Ala Ser Ile Val Ala Ala Leu Leu Ser Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 53
<211> LENGTH: 166
<212> TYPE: PRT
<213> ORGANISM: Homo sapiens

<400> SEQUENCE: 53

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Ala His Gln Ile Ala
                85                  90                  95

His Leu Ala Ala Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 54
<211> LENGTH: 166
<212> TYPE: PRT
<213> ORGANISM: Homo sapiens

<400> SEQUENCE: 54

Met Ser Tyr Asn Leu Leu Gly Phe Leu Gln Arg Ser Ser Asn Phe Gln
1               5                   10                  15

```
Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
             35                  40                  45

Gln Phe Gln Lys Glu Asp Ala Ala Leu Thr Ile Tyr Glu Met Leu Gln
 50                      55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Ala Ala Lys Leu Ala Ala Ala Asp Phe Thr
            100                 105                 110

Arg Gly Ala Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Arg Ile Asn Arg Leu
145                 150                 155                 160

Thr Gly Tyr Leu Arg Asn
            165

<210> SEQ ID NO 55
<211> LENGTH: 166
<212> TYPE: PRT
<213> ORGANISM: Homo sapiens

<400> SEQUENCE: 55

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
             35                  40                  45

Gln Phe Gln Lys Glu Asp Ala Ala Leu Thr Ile Tyr Glu Met Leu Gln
 50                      55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Ala Ala Thr
            100                 105                 110

Ala Gly Ala Ala Met Ser Ala Leu His Leu Lys Arg Tyr Tyr Gly Arg
            115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Arg Ile Asn Arg Leu
145                 150                 155                 160

Thr Gly Tyr Leu Arg Asn
            165

<210> SEQ ID NO 56
<211> LENGTH: 166
<212> TYPE: PRT
<213> ORGANISM: Homo sapiens

<400> SEQUENCE: 56
```

Met Ser Tyr Asn Leu Leu Gly Phe Leu Gln Arg Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Ala Leu Met Ser Ser Leu His Leu Lys Arg Tyr Tyr Gly Ala
            115                 120                 125

Ile Ala Ala Tyr Leu Ala Ala Lys Glu Tyr Ser His Cys Ala Trp Thr
130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 57
<211> LENGTH: 166
<212> TYPE: PRT
<213> ORGANISM: Homo sapiens

<400> SEQUENCE: 57

Met Ser Tyr Asn Leu Leu Gly Phe Leu Gln Arg Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Ala Leu Met Ser Ser Leu His Leu Lys Arg Tyr Tyr Gly Arg
            115                 120                 125

Ile Leu His Tyr Leu Lys Ala Ala Tyr Ser His Cys Ala Trp Thr
130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 58
<211> LENGTH: 166
<212> TYPE: PRT
<213> ORGANISM: Homo sapiens

<400> SEQUENCE: 58

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ala Ala Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 59
<211> LENGTH: 166
<212> TYPE: PRT
<213> ORGANISM: Homo sapiens

<400> SEQUENCE: 59

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Ala Glu Ile Leu Ala Asn Phe Ala Arg Ile Ala Arg Leu
145                 150                 155                 160

Thr Gly Tyr Leu Arg Asn
                165

<210> SEQ ID NO 60

-continued

```
<211> LENGTH: 166
<212> TYPE: PRT
<213> ORGANISM: Homo sapiens

<400> SEQUENCE: 60

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 61
<211> LENGTH: 8
<212> TYPE: PRT
<213> ORGANISM: Homo sapiens

<400> SEQUENCE: 61

Asp Tyr Lys Asp Asp Asp Asp Lys
1               5
```

What is claimed is:

1. A fusion polypeptide comprising:
   (a) an amino acid sequence selected from the group consisting of SEQ ID Nos:45–59; and
   (b) a hinge, CH2 and CH3 domains of an immunoglobulin.

2. The polypeptide of claim 1, wherein the polypeptide is glycosylated at an amino acid in the amino acid sequence.

3. The polypeptide of claim 1, wherein the immunoglobulin is of the IgG class.

4. The polypeptide of claim 1, wherein the polypeptide is covalently linked to a polyalkylglycol polymer.

5. The polypeptide of claim 4, wherein the polyalkylglycol polymer is coupled to the N-terminus of the amino acid sequence of the polypeptide.

* * * * *

UNITED STATES PATENT AND TRADEMARK OFFICE
CERTIFICATE OF CORRECTION

PATENT NO. : 6,800,735 B2
DATED : October 5, 2004
INVENTOR(S) : Whitty, Adrian et al.

It is certified that error appears in the above-identified patent and that said Letters Patent is hereby corrected as shown below:

<u>Title page,</u>
Item [73], Assignee, "Biogen, Inc." with -- Biogen Idec MA Inc. --.

Signed and Sealed this

Twelfth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,800,735 B2
DATED : October 5, 2004
INVENTOR(S) : Whitty, Adrian et al.

Page 1 of 1

It is certified that error appears in the above-identified patent and that said Letters Patent is hereby corrected as shown below:

<u>Title page, Item [54] and Column 1, line 1,</u>
Title, replace "BETA" with -- BETA-1a - IMMUNOGLOBULIN --.

Signed and Sealed this

Second Day of August, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,800,735 B2 | |
| APPLICATION NO. | : 09/832659 | |
| DATED | : October 5, 2004 | |
| INVENTOR(S) | : Adrian Whitty et al. | |

It is certified that error appears in the above-identified patent and that said Letters Patent is hereby corrected as shown below:

Column 3, line 40: "(SerGlyGly) upstream of the histidine tag ($His_6$, positions" should read --(SerGlyGly) upstream of the histidine tag ($His_6$ (SEQ ID NO:63), positions--

Column 3, line 42: "(AspAspAspAspLys) is separate from the histidine tag by a" should read --(AspAspAspAspLys) (SEQ ID NO: 62) is separate from the histidine tag by a--

Column 15, line 36: "in SEQ ID NO:43; GGGGS in SEQ ID NO:8)." should read --in SEQ ID NO:43; GGGGS (SEQ ID NO:64) in SEQ ID NO:8).--

Column 32, line 61: "linker sequence (DDDDK) and a terminal restriction" should read --linker sequence (DDDDK) (SEQ ID NO:62) and a terminal restriction--

Column 35, line 33: "changed the enterokinase linker sequence (DDDDK) to a" should read --changed the enterokinase linker sequence (DDDDK) (SEQ ID NO:62) to a--

Column 35, line 34: "GGGGS linker sequence in frame and fused 3' to the human" should read --GGGGS (SEQ ID NO:64) linker sequence in frame and fused 3' to the human--

Column 45, lines 39-44:
"<210> SEQ ID NO 5
<211> LENGTH: 60
<212> TYPE: DNA
<213> ORGANISM: Homo sapiens
<400> SEQUENCE: 5
gatctagcaa tgctgcctgt gctgccctcc tggctgcctt gaatgggagg cttgaatact          60"

should read

--<210> 5
<211> LENGTH: 69
<212> TYPE: DNA
<213> Artificial Sequence

<220>
<223> Description of Artificial Sequence: Synthetic Construct

UNITED STATES PATENT AND TRADEMARK OFFICE
CERTIFICATE OF CORRECTION

PATENT NO. : 6,800,735 B2  
APPLICATION NO. : 09/832659  
DATED : October 5, 2004  
INVENTOR(S) : Adrian Whitty et al.

It is certified that error appears in the above-identified patent and that said Letters Patent is hereby corrected as shown below:

<220>  
<221> CDS  
<222> (1)..(69)

<400> SEQUENCE: 5  
ttcattaaca gacttacatg ttacctccga aacgtcgaca aaactcacac atgcccaccg     60 tgc cca gca     69--

Column 45, line 45 to Column 47, line 2:  
"<210> SEQ ID NO 6  
<211> LENGTH: 51  
<212> TYPE: DNA  
<213> ORGANISM: Homo sapiens  
<400> SEQUENCE: 6  
tattatggga ggattctgca ttacctgaag gccaaggagt actcacactg t     51"

should read

--<210> SEQ ID NO 6  
<211> LENGTH: 23  
<212> TYPE: PRT  
<213> Artificial Sequence <220>  
<223> Description of Artificial Sequence: Synthetic Construct
<400> 6  
Phe Ile Asn Arg Leu Thr Cys Tyr Leu Arg Asn Val Asp Lys Thr His  
　1　　　　　　　5　　　　　　　　10　　　　　　　　15

Thr Cys Pro Pro Cys Pro Ala  
　　　　　20--

UNITED STATES PATENT AND TRADEMARK OFFICE
CERTIFICATE OF CORRECTION

PATENT NO. : 6,800,735 B2  
APPLICATION NO. : 09/832659  
DATED : October 5, 2004  
INVENTOR(S) : Adrian Whitty et al.

It is certified that error appears in the above-identified patent and that said Letters Patent is hereby corrected as shown below:

Column 47, lines 3-9:  
"<210> SEQ ID NO 7  
<211> LENGTH: 76  
<212> TYPE: DNA  
<213> ORGANISM: Homo sapiens  
<400> SEQUENCE: 7  
aattgaatgg gagggctgca gcttgcgctg cagacaggat gaactttgac atccctgagg     60
agattaagca gctgca     76"

should read

--<210> SEQ ID NO 7  
<211> LENGTH: 81  
<212> TYPE: DNA  
<213> Artificial Sequence <220>  
<223> Description of Artificial Sequence: Synthetic Construct

<220>  
<221> CDS  
<222> (1)..(81)

<400> 7  
ttcattaaca gacttacatg ttacctccga aacggcggtg gtggcagcgt cgacaaaact     60
cacacatgcc caccgtgccc a     81--

Column 47, lines 10-22:  
"<210> SEQ ID NO 8  
<211> LENGTH: 51  
<212> TYPE: PRT  
<213> ORGANISM: Homo sapiens  
<400> SEQUENCE: 8  
Ala Ala Thr Thr Gly Ala Ala Thr Gly Gly Gly Ala Gly Gly Cys Thr  
  1              5                10              15

UNITED STATES PATENT AND TRADEMARK OFFICE
CERTIFICATE OF CORRECTION

PATENT NO. : 6,800,735 B2
APPLICATION NO. : 09/832659
DATED : October 5, 2004
INVENTOR(S) : Adrian Whitty et al.

It is certified that error appears in the above-identified patent and that said Letters Patent is hereby corrected as shown below:

Thr Gly Ala Ala Thr Ala Cys Thr Gly Cys Cys Thr Cys Ala Ala Gly
        20                      25                  30

Gly Ala Cys Ala Gly Gly Ala Thr Gly Ala Ala Cys Thr Thr Thr Gly
        35                      40                  45

Ala Cys Ala
    50"

should read

--<210> SEQ ID NO 8
<211> LENGTH: 27
<212> TYPE: PRT
<213> Artificial Sequence

<220>
<223> Description of Artificial Sequence: Synthetic Construct

<400> 8
Phe Ile Asn Arg Leu Thr Cys Tyr Leu Arg Asn Gly Gly Gly Gly Ser
 1           5                  10                15

Val Asp Lys Thr His Thr Cys Pro Pro Cys Pro
        20                    25--

Column 47, lines 23-28:
"<210> SEQ ID NO 9
<211> LENGTH: 60
<212> TYPE: DNA
<213> ORGANISM: Homo sapiens
<400> SEQUENCE: 9
ttctccggag acgatgatga caagatgagc tacaacttgc ttggattcct acaaagaagc      60"

UNITED STATES PATENT AND TRADEMARK OFFICE
CERTIFICATE OF CORRECTION

PATENT NO. : 6,800,735 B2
APPLICATION NO. : 09/832659
DATED : October 5, 2004
INVENTOR(S) : Adrian Whitty et al.

It is certified that error appears in the above-identified patent and that said Letters Patent is hereby corrected as shown below:

should read

--<210> SEQ ID NO 9
<211> LENGTH: 60
<212> TYPE: DNA
<213> Artificial Sequence

<220>

<223> Description of Artificial Sequence: Synthetic Primer

<400> 9
ttctccggag acgatgatga caagatgagc tacaacttgc ttggattcct acaaagaagc     60--

Column 47, lines 29-34:
"<210> SEQ ID NO 10
<211> LENGTH: 50
<212> TYPE: DNA
<213> ORGANISM: Homo sapiens
<400> SEQUENCE: 10
cgtcagagct gaaatcctag caaactttgc attcattgca agacttacag     50"

should read

--<210> SEQ ID NO 10
<211> LENGTH: 39
<212> TYPE: DNA
<213> Artificial Sequence

<220>
<223> Description of Artificial Sequence: Synthetic Primer

<400> 10
gccgctcgag ttatcagttt cggaggtaac ctgtaagtc     39--

UNITED STATES PATENT AND TRADEMARK OFFICE
CERTIFICATE OF CORRECTION

PATENT NO. : 6,800,735 B2
APPLICATION NO. : 09/832659
DATED : October 5, 2004
INVENTOR(S) : Adrian Whitty et al.

It is certified that error appears in the above-identified patent and that said Letters Patent is hereby corrected as shown below:

Column 47, lines 35-40:
"<210> SEQ ID NO 11
<211> LENGTH: 47
<212> TYPE: DNA
<213> ORGANISM: Homo sapiens
<400> SEQUENCE: 11
ggtggtctca catgagctac aacttgcttg gattcctaca aagaagc        47"

should read

--<210> SEQ ID NO 11
<211> LENGTH: 35
<212> TYPE: DNA
<213> Artificial Sequence

<220>
<223> Description of Artificial Sequence: Synthetic Primer

<400> 11
agcttccggg ggccatcatc atcatcatca tagct        35--

Column 47, lines 41-46:
"<210> SEQ ID NO 12
<211> LENGTH: 50
<212> TYPE: DNA
<213> ORGANISM: Homo sapiens
<400> SEQUENCE: 12
gccctcgagt cgaccttgtc atcatcgtcg tttcggaggt aacctgtaag        50"

should read

--<210> SEQ ID NO 12
<211> LENGTH: 35
<212> TYPE: DNA
<213> Artificial Sequence

<220>
<223> Description of Artificial Sequence: Synthetic Primer

UNITED STATES PATENT AND TRADEMARK OFFICE
CERTIFICATE OF CORRECTION

PATENT NO. : 6,800,735 B2
APPLICATION NO. : 09/832659
DATED : October 5, 2004
INVENTOR(S) : Adrian Whitty et al.

It is certified that error appears in the above-identified patent and that said Letters Patent is hereby corrected as shown below:

<400> 12
ccggagctat gatgatgatg atgatggccc ccgga                35--

Column 47, line 47 to Column 49, line 4:
"<210> SEQ ID NO 13
<211> LENGTH: 21
<212> TYPE: DNA
<213> ORGANISM: Homo sapiens
<400> SEQUENCE: 13
caagcttgct agcggccgcg g                21"

should read

--<210> SEQ ID NO 13
<211> LENGTH: 87
<212> TYPE: DNA
<213> Artificial Sequence

<220>
<223> Description of Artificial Sequence: Synthetic Oligonucleotide

<400> 13
ccggagacga tgatgacaag atggcttacg ccgctcttgg agccctacaa gcttctagca        60
attttcagtg tcagaagctc ctgtggc                87--

Column 49, lines 5-10:
"<210> SEQ ID NO 14
<211> LENGTH: 28
<212> TYPE: DNA
<213> ORGANISM: Homo sapiens
<400> SEQUENCE: 14
ggtggtctca catggcttga gaagctgc                28"

should read

UNITED STATES PATENT AND TRADEMARK OFFICE
CERTIFICATE OF CORRECTION

| | | |
|---|---|---|
| PATENT NO. | : 6,800,735 B2 | Page 8 of 13 |
| APPLICATION NO. | : 09/832659 | |
| DATED | : October 5, 2004 | |
| INVENTOR(S) | : Adrian Whitty et al. | |

It is certified that error appears in the above-identified patent and that said Letters Patent is hereby corrected as shown below:

--<210> SEQ ID NO 14
<211> LENGTH: 60
<212> TYPE: DNA
<213> Artificial Sequence

<220>
<223> Description of Artificial Sequence: Synthetic Oligonucleotide

<440> 14
gatctagcaa tgctgcctgt gctgccctcc tggctgcctt gaatgggagg cttgaatact          60--

Column 49, lines 11-16:
"<210> SEQ ID NO 15
<211> LENGTH: 20
<212> TYPE: DNA
<213> ORGANISM: Homo sapiens
<400> SEQUENCE: 15
aggtsmarct gcagsagtcw          20"

should read

--<210> SEQ ID NO 15
<211> LENGTH: 52
<212> TYPE: DNA
<213> Artificial Sequence

<220>
<223> Description of Artificial Sequence: Synthetic Oligonucleotide

<400> 15
gcctcaagga caggatgaac tttgacatcc ctgaggagat taagcagctg ca          52--

UNITED STATES PATENT AND TRADEMARK OFFICE
CERTIFICATE OF CORRECTION

PATENT NO. : 6,800,735 B2
APPLICATION NO. : 09/832659
DATED : October 5, 2004
INVENTOR(S) : Adrian Whitty et al.

It is certified that error appears in the above-identified patent and that said Letters Patent is hereby corrected as shown below:

Column 49, lines 17-22:
"<210> SEQ ID NO 16
<211> LENGTH: 36
<212> TYPE: DNA
<213> ORGANISM: Homo sapiens
<400> SEQUENCE: 16
ctgagctcat ttacccggag tccgggagaa gctctt     36"

should read

--<210> SEQ ID NO 16
<211> LENGTH: 76
<212> TYPE: DNA
<213> Artificial Sequence

<220>
<223> Description of Artificial Sequence: Synthetic Oligonucleotide

<400> 16
aattgaatgg gagggctgca gcttgcgctg cagacaggat gaactttgac atccctgagg     60
agattaagca gctgca     76--

Column 49, lines 23-28:
"<210> SEQ ID NO 17
<211> LENGTH: 33
<212> TYPE: DNA
<213> ORGANISM: Homo sapiens
<400> SEQUENCE: 17
agcttgctag cggccgcggc ctcactggct tca     33"

should read

--<210> SEQ ID NO 17
<211> LENGTH: 76
<212> TYPE: DNA
<213 Artificial Sequence

UNITED STATES PATENT AND TRADEMARK OFFICE
CERTIFICATE OF CORRECTION

| | | |
|---|---|---|
| PATENT NO. | : 6,800,735 B2 | Page 10 of 13 |
| APPLICATION NO. | : 09/832659 | |
| DATED | : October 5, 2004 | |
| INVENTOR(S) | : Adrian Whitty et al. | |

It is certified that error appears in the above-identified patent and that said Letters Patent is hereby corrected as shown below:

<220>
<223> Description of Artificial Sequence: Synthetic Oligonucleotide

<400> 17
aatgaatgg gaggcttgaa tactgcctca aggacagggc tgcatttgct atccctgcag     60
agattaagca gctgca     76--

Column 49, lines 29-34:
"<210> SEQ ID NO 18
<211> LENGTH: 37
<212> TYPE: DNA
<213> ORGANISM: Homo sapiens
<400> SEQUENCE: 18
atacgcgtcg acgtttcgga ggtaacatgt aagtctg     37"

should read

--<210> SEQ ID NO 18
<211> LENGTH: 51
<212> TYPE: DNA
<213> Artificial Sequence

<220>
<223> Description of Artificial Sequence: Synthetic Oligonucleotide

<400> 18
aattgaatgg gaggcttgaa tactgcctca aggacaggat gaactttgac a     51--

Column 49, lines 35-40:
"<210> SEQ ID NO 19
<211> LENGTH: 33
<212> TYPE: DNA
<213> ORGANISM: Homo sapiens
<400> SEQUENCE: 19
agcttgctag cggccgcggc ctcactggct tca     33"

UNITED STATES PATENT AND TRADEMARK OFFICE
CERTIFICATE OF CORRECTION

PATENT NO. : 6,800,735 B2 Page 11 of 13
APPLICATION NO. : 09/832659
DATED : October 5, 2004
INVENTOR(S) : Adrian Whitty et al.

It is certified that error appears in the above-identified patent and that said Letters Patent is hereby corrected as shown below:

should read

--<210> 19
<211> 43
<212> DNA
<213> Artificial Sequence

<220>
<223> Description of Artificial Sequence: Synthetic Oligonucleotide

<400> 19
tccctgagga gattgctgca gctgcagctt tcgctgcagc tga                    43--

Column 49, lines 41-46:
"<210> SEQ ID NO 20
<211> LENGTH: 51
<212> TYPE: DNA
<213> ORGANISM: Homo sapiens
<400> SEQUENCE 20
tacacgtcga cgctgccacc accgccgttt cggaggtaac atgtaagtct g            51"

should read

--<210> SEQ ID NO 20
<211> LENGTH: 78
<212> TYPE: DNA
<213> Artificial Sequence

<220>
<223> Description of Artificial Sequence: Synthetic Oligonucleotide

<400> 20
cgccgcgttg accatctatg agatgctcgc taacatcgct agcattttca gacaagattc   60
atctagcact ggctggaa                                                 78--

UNITED STATES PATENT AND TRADEMARK OFFICE
CERTIFICATE OF CORRECTION

PATENT NO. : 6,800,735 B2
APPLICATION NO. : 09/832659
DATED : October 5, 2004
INVENTOR(S) : Adrian Whitty et al.

It is certified that error appears in the above-identified patent and that said Letters Patent is hereby corrected as shown below:

Column 49, line 47 to Column 51, line 5:
"<210> SEQ ID NO 21
<211> LENGTH: 39
<212> TYPE: DNA
<213> ORGANISM: Homo sapiens
<400> SEQUENCE: 21
gccgctcgag ttatcagttt cggaggtaac ctgtaagtc        39"

should read

--<210> SEQ ID NO 21
<211> LENGTH: 78
<212> TYPE: DNA
<213> Artificial Sequence

<220>
<223> Description of Artificial Sequence: Synthetic Oligonucleotide

<400> 21
cgccgcattg accatctatg agatgctcca gaacatcttt gctattttcg ctgcagcttc        60
atctagcact ggctggaa        78--

After Column 49, line 47 to Column 51, line 5 please add:

--<210> SEQ ID NO 62
<211> LENGTH: 5
<212> TYPE: PRT
<213> Artificial Sequence

<220>
<223> Description of Artificial Sequence: Synthetic Peptide

<400> 62
Asp Asp Asp Asp Lys
 1               5

UNITED STATES PATENT AND TRADEMARK OFFICE
CERTIFICATE OF CORRECTION

PATENT NO.       : 6,800,735 B2
APPLICATION NO.  : 09/832659
DATED            : October 5, 2004
INVENTOR(S)      : Adrian Whitty et al.

It is certified that error appears in the above-identified patent and that said Letters Patent is hereby corrected as shown below:

<210> SEQ ID NO 63
<211> LENGTH: 6
<212> TYPE: PRT
<213> Artificial Sequence

<220>
<223> Description of Artificial Sequence: Synthetic 6x His tag

<400> 63
His His His His His His
 1               5

<210> SEQ ID NO 64
<211> LENGTH: 5
<212> TYPE: PRT
<213> Artificial Sequence

<220>
<223> Description of Artificial Sequence: Synthetic Peptide

<400> 64
Gly Gly Gly Gly Ser
 1               5--

Signed and Sealed this

Twenty-eighth Day of October, 2008

JON W. DUDAS
*Director of the United States Patent and Trademark Office*